United States Patent
Bridges et al.

(10) Patent No.: US 6,696,440 B1
(45) Date of Patent: Feb. 24, 2004

(54) TREATMENT OF ASTHMA WITH MEK INHIBITORS

(75) Inventors: Alexander James Bridges, Saline, MI (US); David Thomas Dudley, Ann Arbor, MI (US); James Leslie Mobley, Brighton, MI (US); Alan Robert Saltiel, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/889,091

(22) PCT Filed: Dec. 21, 1999

(86) PCT No.: PCT/US99/30419
§ 371 (c)(1),
(2), (4) Date: Jul. 11, 2001

(87) PCT Pub. No.: WO00/40235
PCT Pub. Date: Jul. 13, 2000

Related U.S. Application Data
(60) Provisional application No. 60/115,086, filed on Jan. 7, 1999.

(51) Int. Cl.[7] ............................................. A61K 31/535
(52) U.S. Cl. .................... 514/231.2; 514/277; 514/315; 514/408; 514/438; 514/532; 514/534; 514/535
(58) Field of Search ................................. 514/532, 534, 535, 231.2, 277, 315, 408, 438

(56) References Cited

U.S. PATENT DOCUMENTS
5,525,625 A  *  6/1996  Bridges et al. .............. 514/456
6,469,004 B1 * 10/2002  Barrett et al. ................ 514/248

FOREIGN PATENT DOCUMENTS
WO     98/20868   *   5/1998
WO     98/37881   *   9/1998

OTHER PUBLICATIONS
Whelchel et al., Am. J. Respir. Cell Mol. Biol. 16:589–596, (1997).*

Tsang et al., British Journal of Pharmacology, (1998), 125, 61–68.*

M. H. Grayson, et al., "New Concepts in the Pathogenesis and Treatment of Allergic Asthma", Mt. Sinai J Med., Sep. 4, 1998, pp 246–256, Vol 65, No 4.

M. B. Hershenson, et al., "Mitogen–activated Signaling in Cultured Airway Smooth Muscle Cells", Can J. Physiol. Pharmacol., 1997, pp 898–910, Vol 75.

T. R. Walker, et al., "Platelet–Derived Growth Factor–BB and Thrombin Activate Phosphoinositide 3–Kinase and Protein Kinase B: Role in Mediating Airway Smooth Muscle Proliferation", Sep. 1998, pp 1007–1015, Vol 54.

P. Vichi, et al., "Endothelin–Stimulated ERK Activation in Airway Smooth–Muscle Cells Requires Calcium Influx and Raf Activation", Am. J. Respir. Cell Mol. Biol., 1999, pp 99–105, Vol 20.

* cited by examiner

Primary Examiner—Phyllis G. Spivack
Assistant Examiner—C. Delacroix-Muirheid
(74) Attorney, Agent, or Firm—Evelyn D. Shen; Suzanne M. Harvey

(57) ABSTRACT

This invention provides a method of preventing or treating asthma by administering to a patient in need of treatment an effective amount of a selective MEK inhibitor, especially a phenyl amine of Formula I and II:

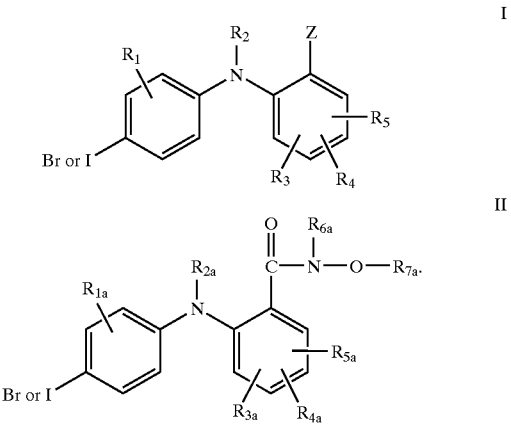

13 Claims, No Drawings

TREATMENT OF ASTHMA WITH MEK INHIBITORS

This application is a 371 application of PCT/US99/30419 filed Dec. 21, 1999, which claims the benefit of priority to U.S. provisional application Ser. No. 60/115,086 filed Jan. 7, 1999.

FIELD OF THE INVENTION

This invention relates to a method for preventing and treating asthma in mammals comprising administering a compound characterized as an inhibitor of a family of enzymes known as MEK kinases, which are groups of MAP (mitogen-associated protein kinase) and Erk (extracellular signal-regulated) Kinases. These are enzymes that regulate phosphorylation of substrates in mammals.

BACKGROUND OF THE INVENTION

Asthma is a heterogeneous disorder of the airways that afflicts millions of people. Airway inflammation, hyperresponsiveness, and obstruction characterize the condition. The disease often causes spasms of the bronchial smooth muscle system, and affects both the upper and lower respiratory tracts. There are several forms of asthma, characterized by varying degrees of severity. Mild asthma, for example, is defined as brief episodes of wheezing, with or without dyspnea or cough. Moderately severe asthma is defined as wheezing and dyspnea, and can be with or without cough and expectoration, but generally interferes with daily activities and/or sleeping. Severe asthma is characterized by incapacitation due to dyspnea, and the afflicted patient typically is unable to eat or sleep normally, is very anxious, and is often exhausted. A condition known as status asthmaticus is the most severe form of asthma, and generally requires intensive hospital care, and may even prove fatal. The disease may occur as a result of both allergic and nonallergic mechanisms.

While there are several treatments available for relieving the symptoms and discomfort associated with asthma, there are no cures. Moreover, the current treatments often cause side effects that exacerbate the discomfort and precipitate other debilitating conditions. Mild asthma generally is treated with beta-adrenergic drugs, as well as antihistamines, especially in the case of children, to prevent or abort sporadic episodes. Moderately severe and severe asthma are generally treated with adrenergic agents and bronchodilators, as well as corticosteroids. Other actions caused by antiasthmatic agents which limit their widespread use include headache, fatigue, dry mouth, nervousness, and in some cases addiction and substance abuse. Recent advances in the understanding of the pathogenesis and treatment of asthma is discussed more fully by Grayson et al., *The Mount Sinai Journal of Medicine*, September 1998;65(4):246–256.

Because asthma is so prevalent in both children and adults, there is an ongoing need for agents that can treat the disease, or at least relieve the symptoms that accompany the disease, without causing undesirable side effects. We have now discovered that MEK inhibitors are particularly useful for treating asthma and relieving the symptoms that accompany the disease. An object of this invention is therefore to provide a new method for preventing and treating asthmatic conditions.

SUMMARY OF THE INVENTION

This invention provides a method of preventing and treating asthma, said method comprising the step of administering to a patient an antiasthmatic-effective amount of a MEK inhibitor. Selective MEK inhibitors are those compounds which inhibit the MEK 1 and MEK 2 enzymes without substantial inhibition of other such enzymes. In a preferred embodiment, the invention provides a method for preventing or treating asthma by administering a MEK inhibitor. In a further embodiment, the invention provides a method for preventing and/or treating asthma comprising administering an effective amount of the selective MEK inhibitor described in U.S. Pat. No. 5,525,625, incorporated herein by reference, which selective MEK inhibitor is 2-(2-amino-3-methoxyphenyl)-4-oxo-4H-[1]benzopyran.

In another preferred embodiment, the MEK inhibitor to be administered is a phenyl amine derivative of Formula I:

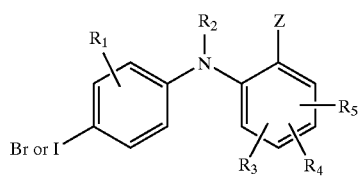

In Formula (I), $R_1$ is hydrogen, hydroxy, $C_1$–$C_8$ alkyl, $C_1$–$C_8$ alkoxy, halo, trifluoromethyl, or CN. $R_2$ is hydrogen. $R_3$, $R_4$, and $R_5$ are independently selected from hydrogen, hydroxy, halo, trifluoromethyl, $C_1$–$C_8$ alkyl, $C_1$–$C_8$ alkoxy, nitro, CN, and —(O or NH)$_m$—(CH$_2$)$_n$—$R_9$. $R_9$ is hydrogen, hydroxy, COOH, or $NR_{10}R_{11}$; n is 0–4; m is 0 or 1. Each of $R_{10}$ and $R_{11}$ is independently selected from hydrogen and $C_1$–$C_8$ alkyl, or taken together with the nitrogen to which they are attached can complete a 3–10 member cyclic ring optionally containing 1, 2, or 3 additional heteroatoms selected from O, S, NH, or N—($C_1$–$C_8$ alkyl). Z is $COOR_7$, tetrazolyl, $CONR_6R_7$, $CONHNR_{10}R_{11}$, or $CH_2OR_7$. $R_6$ and $R_7$ independently are hydrogen, $C_1$–$C_8$ alkyl $C_2$–$C_8$ alkenyl, $C_2$–$C_8$ alkynyl, (CO)—$C_1$–$C_8$ alkyl, aryl, heteroaryl, $C_3$–$C_{10}$ cycloalkyl, or $C_3$–$C_{10}$ (cycloalkyl optionally containing one, two, or three heteroatoms selected from O, S, NH, or N alkyl); or $R_6$ and $R_7$ together with the nitrogen to which they are attached complete a 3–10 member cyclic ring optionally containing 1, 2, or 3 additional heteroatoms selected from O, S, NH, or N alkyl. In formula (I), any of the foregoing alkyl, alkenyl, aryl, heteroaryl, heterocyclic, and alkynyl groups can be unsubstituted or substituted by halo, hydroxy, $C_1$–$C_6$ alkoxy, amino, nitro, $C_1$–$C_4$ alkylamino, di($C_1$–$C_4$)alkylamino, $C_3$–$C_6$ cycloalkyl, phenyl, phenoxy, $C_3$–$C_5$ heteroaryl or heterocyclic radical, or $C_3$–$C_5$ heteroaryloxy or heterocyclic radicaloxy. The invention also provides a pharmaceutically acceptable salt, ester, amide, or prodrug of each of the disclosed MEK inhibitors.

Preferred embodiments of Formula (I) have a structure wherein: (a) $R_1$ is hydrogen, methyl, methoxy, fluoro, chloro, or bromo; (b) $R_2$ is hydrogen; (c) $R_3$, $R_4$, and $R_5$ independently are hydrogen, fluoro, chloro, bromo, iodo, methyl, methoxy, or nitro; (d) $R_{10}$ and $R_{11}$ independently are hydrogen or methyl; (e) Z is $COOR_7$, tetrazolyl, $CONR_6R_7$, $CONHNR_{10}R_{11}$, or $CH_2OR_7$; $R_6$ and $R_7$ independently are hydrogen, $C_{1-4}$ alkyl, heteroaryl, or $C_{3-5}$ cycloalkyl optionally containing one or two heteroatoms selected from O, S, or NH; or $R_6$ and $R_7$ together with the nitrogen to which they are attached complete a 5–6 member cyclic ring optionally containing 1 or 2 additional heteroatoms selected from O, NH or N-alkyl; and wherein any of the foregoing alkyl or aryl groups can be unsubstituted or substituted by halo, hydroxy, methoxy, ethoxy, or heteroaryloxy (such as 2,3,4, 5,6-pentafluorophenyl); (f) Z is COOR$_7$; (g) R$_7$ is H, pentafluorophenyl, or tetrazolyl; (h) R$_3$, R$_4$, and R$_5$ are independently H, fluoro, or chloro; (i) R$_4$ is fluoro; (j) two of R$_3$, R$_4$, and R$_5$ are fluoro; or (k) or combinations of the above. In another preferred embodiment of Formula (I), R$_1$ is methyl, fluoro, chloro, or bromo.

In a more preferred embodiment, the MEK inhibitor is selected from a compound in Formula (I) Compound Table below.

FORMULA (I) COMPOUND TABLE

[4-Chloro-2-(1H-tetrazol-5-yl)-phenyl-(4-iodo-2-methyl-phenyl)-amine
(4-iodo-2-methyl-phenyl)-[2-(1H-tetrazol-5-yl)-phenyl]amine
[4-nitro-2-(1H-tetrazol-5-yl)-phenyl-(4-iodo-2-methyl-phenyl)-amine
4-Fluoro-2-(4-iodo-2-methylphenylamino)benzoic acid
3,4,5-Trifluoro-2-(4-iodo-2-methyl-phenylamino)-benzoic acid
3,4-Difluoro-2-(4-iodo-2-methyl-phenylamino)-benzoic acid
5-Bromo-3,4-difluoro-2-(4-iodo-2-methyl-phenylamino)-benzoic acid
5-Chloro-2-(4-iodo-2-methyl-phenylamino)-benzoic acid
Sodium 5-Chloro-2-(4-iodo-2-methyl-phenylamino)-benzoate
5-Bromo-2-(4-iodo-2-methyl-phenylamino)-benzoic acid
2-(4-Iodo-2-methyl-phenylamino)-5-nitro-benzoic acid
4-Chloro-2-(4-iodo-2-methyl-phenylamino)-benzoic acid
2-(4-Iodo-2-methyl-phenylamino)-benzoic acid
5-Fluoro-2-(4-iodo-2-methyl-phenylamino)-benzoic acid
5-Iodo-2-(4-iodo-2-methyl-phenylamino)-benzoic acid
2,3,5-Trifluoro-4-(4-iodo-2-methyl-phenylamino)-benzoic acid
2-(4-Iodo-phenylamino)-5-methoxy-benzoic acid
5-Methyl-2-(4-iodo-2-methyl-phenylamino)-benzoic acid
2-(4-Iodo-2-methyl-phenylamino)-4-nitro-benzoic acid
2-(4-Bromo-2-methyl-phenylamino)-4-fluoro-benzoic acid
2-(2-Bromo-4-iodo-phenylamino)-5-nitro-benzoic acid
2-(4-Bromo-2-methyl-phenylamino)-3,4-difluoro-benzoic acid
5-Chloro-N-(2-hydroxyethyl)-2-(4-iodo-2-methyl-phenylamino)-benzamide
4-Fluoro-2-(4-iodo-2-methyl-phenylamino)-benzamide
4-Fluoro-2-(4-iodo-2-methyl-phenylamino)-N-methyl-benzamide
N-Ethyl-4-fluoro-2-(4-iodo-2-methyl-phenylamino)-benzamide
4-Fluoro-2-(4-iodo-2-methyl-phenylamino)-N,N-dimethyl-benzamide
4-Fluoro-2-(4-iodo-2-methyl-phenylamino)-N-(1H-tetrazol-5-yl)-benzamide
5-Bromo-2-(4-iodo-2-methyl-phenylamino)-benzamide
5-Chloro-2-(4-iodo-2-methyl-phenylamino)-N,N-dimethyl-benzamide
[5-Chloro-2-(4-iodo-2-methyl-phenylamino)-benzoylamino]-acetic acid
4-Fluoro-2-(4-iodo-2-methyl-phenylamino)-N-propyl-benzamide
5-Bromo-N-(2-hydroxy-ethyl)-2-(4-iodo-2-methyl-phenylamino)-benzamide
N,N-Diethyl-4-fluoro-2-(4-iodo-2-methyl-phenylamino)-benzamide
4-Fluoro-N-{3-[4-(2-hydroxy-ethyl)-piperazin-1-yl]-propyl}-2-(4-iodo-2-methyl-phenylamino)-benzamide
N,N-Diethyl-2-(4-iodo-2-methyl-phenylamino)-5-nitro-benzamide
N-Butyl-4-fluoro-2-(4-iodo-2-methyl-phenylamino)-benzamide
5-Chloro-N,N-diethyl-2-(4-iodo-2-methyl-phenylamino)-benzamide
5-Bromo-2-(4-iodo-2-methyl-phenylamino)-N,N-dimethyl-benzamide
5-Bromo-3,4-difluoro-N-(2-hydroxy-ethyl)-2-(4-iodo-2-methyl-phenylamino)-benzamide
N-(2,3-Dihydroxy-propyl)-3,4-difluoro-2-(4-iodo-2-methyl-phenylamino)-benzamide
5-Bromo-3,4-difluoro-2-(4-iodo-2-methyl-phenylamino)-N-(2-piperidin-1-yl-ethyl)-benzamide
3,4-Difluoro-N-(2-hydroxy-ethyl)-2-(4-iodo-2-methyl-phenylamino)-benzamide
N-(2,3-Dihydroxy-propyl)-4-fluoro-2-(4-iodo-2-methyl-phenylamino)-benzamide
3,4-Difluoro-N-(3-hydroxy-propyl)-2-(4-iodo-2-methyl-phenylamino)-benzamide
5-Bromo-3,4-difluoro-2-(4-iodo-2-methyl-phenylamino)-N-(2-pyrrolidin-1-yl-ethyl)-benzamide
5-Bromo-3,4-difluoro-2-(4-iodo-2-methyl-phenylamino)-N-(2-pyridin-4-yl-ethyl)-benzamide
4-Fluoro-N-(2-hydroxy-ethyl)-2-(4-iodo-2-methyl-phenylamino)-benzamide
5-Bromo-N-(3-dimethylamino-propyl)-3,4-difluoro-2-(4-iodo-2-methylphenylamino)-benzamide
5-Bromo-3,4-difluoro-2-(4-iodo-2-methyl-phenylamino)-N-(2-morpholin-4-yl-ethyl)-benzamide
3,4-Difluoro-2-(4-iodo-2-methyl-phenylamino)-N-(2-morpholin-4-yl-ethyl)-benzamide
3,4-Difluoro-2-(4-iodo-2-methyl-phenylamino)-N-(2-pyrrolidin-1-yl-ethyl)-benzamide
3,4-Difluoro-2-(4-iodo-2-methyl-phenylamino)-N-(2-pyridin-4-yl-ethyl)-benzamide
N-(3-Dimethylamino-propyl)-3,4-difluoro-2-(4-iodo-2-methyl phenylamino)-benzamide
N-Benzyl-4-fluoro-2-(4-iodo-2-methyl-phenylamino)-benzamide
2-(4-Bromo-2-methyl-phenylamino)-3,4-difluoro-N-(2-hydroxy-ethyl)-benzamide
4-Fluoro-2-(4-iodo-2-methyl-phenylamino)-N-(2-morpholin-4-yl-ethyl)-benzamide
4-Fluoro-2-(4-iodo-2-methyl-phenylamino)-N-(3-piperidin-1-yl-propyl)-benzamide
3,4-Difluoro-2-(4-iodo-2-methyl-phenylamino)-N-(3-piperidin-1-yl-propyl)-benzamide
4-Fluoro-2-(4-iodo-2-methyl-phenylamino)-N-(2-thiophen-2-yl-ethyl)-benzamide
4-Fluoro-2-(4-iodo-2-methyl-phenylamino)-N-(2-pyrrolidin-1-yl-ethyl)-benzamide
2-(4-Bromo-2-methyl-phenylamino)-3,4-difluoro-N-(2-morpholin-4-yl-ethyl)-benzamide
5-Bromo-3,4-difluoro-2-(4-iodo-2-methyl-phenylamino)-N-pyridin-4-ylmethyl-benzamide
3,4-Difluoro-2-(4-iodo-2-methyl-phenylamino)-N-pyridin-4-ylmethyl-benzamide
2-(4-Bromo-2-methyl-phenylamino)-N-(3-dimethylamino-propyl)-3,4-difluoro-benzamide
4-Fluoro-2-(4-iodo-2-methyl-phenylamino)-N-pyridin-4-ylmethyl-enzamide
4-Fluoro-2-(4-iodo-2-methyl-phenylamino)-N-(2-pyridin-4-yl-ethyl)-benzamide
2-(4-Bromo-2-methyl-phenylamino)-3,4-difluoro-N-(2-pyridin-4-yl-ethyl)-benzamide
2-(4-Bromo-2-methyl-phenylamino)-3,4-difluoro-N-(3-hydroxy-propyl)-benzamide
2-(4-Bromo-2-methyl-phenylamino)-3,4-difluoro-N-(2-pyrrolidin-1-yl-ethyl)-benzamide
4-Fluoro-2-(4-iodo-2-methyl-phenylamino)-N-phenethyl-benzamide
2-(4-Bromo-2-methyl-phenylamino)-3,4-difluoro-N-(2-thiophen-2-yl-ethyl)-benzamide
2-(4-Bromo-2-methyl-phenylamino)-3,4-difluoro-N-pyridin-4-ylmethyl-benzamide
2-(4-Bromo-2-methyl-phenylamino)-3,4-difluoro-N-phenethyl-benzamide
2-(4-Bromo-2-methyl-phenylamino)-3,4-difluoro-N-(2-piperidin-1-yl-ethyl)-benzamide
5-Chloro-N-{3-[4-(2-hydroxy-ethyl)-piperazin-1-yl]-propyl}-2-(4-iodo-2-methyl-phenylamino)-benzamide
5-Fluoro-N-{3-[4-(2-hydroxy-ethyl)-piperazin-1-yl]-propyl}-2-(4-iodo-2-methyl-phenylamino)-benzamide
2-(4-Iodo-2-methyl-phenylamino)-5-nitro-N-pyridin-4-yl methyl-benzamide
5-Bromo-N-{3-[4-(2-hydroxy-ethyl)-piperazin-1-yl]-propyl}-2-(4-iodo-2-methyl-phenylamino)-benzamide
5-Chloro-N-(2-diethylamino-ethyl)-2-(4-iodo-2-methyl-phenylamino)-benzamide
5-Chloro-2-(4-iodo-2-methyl-phenylamino)-N-(2-piperidin-1-yl-ethyl)-benzamide
(3-Hydroxy-pyrrolidin-1-yl)-[5-nitro-2-(4-iodo-2-methyl-phenylamino)-phenyl]-methanone
5-Chloro-2-(4-iodo-2-methyl-phenylamino)-N-(2-pyrrolidin-1-yl-ethyl)-benzamide
5-Bromo-N-(2-diethylamino-ethyl)-2-(4-iodo-2-methyl-phenylamino)-benzamide
N-{2-[Bis-(2-hydroxy-ethyl)-amino]-ethyl}-5-chloro-2-(4-iodo-2-methyl-phenylamino)-benzamide
N-{2-[Bis-(2-hydroxy-ethyl)-amino]-ethyl}-5-bromo-2-(4-iodo-2-methyl-phenylamino)-benzamide
N-{3-[4-(2-Hydroxy-ethyl)-piperazin-1-yl]-propyl}-2-(4-iodo-2-methyl-phenylamino)-benzamide
5-Fluoro-2-(4-iodo-2-methyl-phenylamino)-N-pyridin-4-ylmethyl-benzamide
5-Bromo-2-(4-iodo-2-ethyl-phenylamino)-N-(2-pyrrolidin-1-yl-ethyl)-benzamide
5-Bromo-2-(4-iodo-2-methyl-phenylamino)-N-(2-piperidin-1-yl-ethyl)-benzamide

FORMULA (I) COMPOUND TABLE

5-Fluoro-2-(4-iodo-2-methyl-phenylamino)-N-(2-pyrrolidin-1-yl-ethyl)-benzamide
5-Chloro-N-(3-dimethylamino-propyl)-2-(4-iodo-2-methyl-phenylamino)-benzamide
N-{2-[Bis-(2-hydroxy-ethyl)-amino]-ethyl}-5-fluoro-2-(4-iodo-2-methyl-phenylamino)-benzamide
5-Chloro-N-(3 hydroxy-propyl)-2-(4-iodo-2-methyl-phenylamino)-benzamide
5-Chloro-N-(3-diethylamino-2-hydroxy-propyl)-2-(4-iodo-2-methyl-phenylamino)-benzamide
5-Fluoro-2-(4-iodo-2-methyl-phenylamino)-N-(3-piperidin-1-yl-ethyl)-benzamide
5-Bromo-N-(3-hydroxy-propyl)-2-(4-iodo-2-methyl-phenylamino)-benzamide
5-Bromo-2-(4-iodo-2-methyl-phenylamino)-N-(3-piperidin-1-yl-propyl)-benzamide
N-{2-[Bis-(2-hydroxy-ethyl)-amino]-ethyl}-2-(4-iodo-2-methyl-phenylamino)-5-nitro-benzamide
5-Chloro-2-(4-iodo-2-methyl-phenylamino)-N-(2-morpholin-4-yl-ethyl)-benzamide
5-Chloro-N-(3-diethylamino-propyl)-2-(4-iodo-2-methyl-phenylamino)-benzamide
5-Chloro-N-(2-diisopropylamino-ethyl)-2-(4-iodo-2-methyl-phenylamino)-benzamide
5-Chloro-2-(4-iodo-2-methyl-phenylamino)-N-(3-piperidin-1-yl-propyl)-benzamide
2-(4-Iodo-2-methyl-phenylamino)-5-nitro-N-(2-piperidin-1-yl-ethyl)-benzamide
5-Bromo-2-(4-iodo-2-methyl-phenylamino)-N-(2-piperazin-1-yl-ethyl)-benzamide
N-(2-Diethylamino-ethyl)-5-fluoro-2-(4-iodo-2-methyl-phenylamino)-benzamide
5-Bromo-N-(3-dimethylamino-propyl)-2-(4-iodo-2-methyl-phenylamino)-benzamide
N-(3-Hydroxy-propyl)-2-(4-iodo-2-methyl-phenylamino)-5-nitro-benzamide
5-Fluoro-N-(3-hydroxy-propyl)-2-(4-iodo-2-methyl-phenylamino)-benzamide
N-(3-Diethylamino-propyl)-5-fluoro-2-(4-iodo-2-methyl-phenylamino)-benzamide
N-(3-Diethylamino-propyl)-2-(4-iodo-2-methyl-phenylamino)-5-nitro-benzamide
5-Bromo-2-(4-iodo-2-methyl-phenylamino)-N-(2-morpholin-4-yl-ethyl)-benzamide
2-(4-Iodo-2-methyl-phenylamino)-5-nitro-N-(3-piperidin-1-yl-propyl)-benzamide
[5-Fluoro-2-(4-iodo-2-methyl-phenylamino)-phenyl]-(2 or 3-hydroxy-pyrrolidin-1-yl)-methanone
5-Bromo-N-(2-diisopropylamino-ethyl)-2-(4-iodo-2-methyl-phenylamino)-benzamide
5-Fluoro-2-(4-iodo-2-methyl-phenylamino)-N-(2-morpholin-4-yl-ethyl)-benzamide
5-Fluoro-2-(4-iodo-2-methyl-phenylamino)-N-(3-piperidin-1-yl-propyl)-benzamide
[5-Fluoro-2-(4-iodo-2-methyl-phenylamino)-phenyl]-4-(2-hydroxy-ethyl)-piperazin-1-yl)-methanone
N-(3-Diethylamino-2-hydroxy-propyl)-5-fluoro-2-(4-iodo-2-methyl-phenylamino)-benzamide
N-Cyclopropyl-5-fluoro-2-(4-iodo-2-methyl-phenylamino)-benzamide
5-Chloro-N-(2-hydroxy-ethyl)-2-(4-iodo-2-methyl-phenylamino)-benzamide
5-Fluoro-N-(2-hydroxy-ethyl)-2-(4-iodo-2-methyl-phenylamino)-benzamide
N-Benzyloxy-5-fluoro-2-(4-iodo-2-methyl-phenylamino)-benzamide
N-Benzyloxy-5-bromo-2-(4-iodo-2-methyl-phenylamino)-benzamide
2-(4-Iodo-2-methyl-phenylamino)-5-nitro-N-(4-sulfamoyl-benzyl)-benzamide
5-Bromo-N-(2-hydroxy-ethyl)-2-(4-iodo-2-methyl-phenylamino)-benzamide
N-(2-Hydroxy-ethyl)-5-iodo-2-(4-iodo-2-methyl-phenylamino)-benzamide
N-(2-Hydroxy-ethyl)-2-(4-iodo-2-ethyl-phenylamino)-5-nitro-benzamide
2-(4-Iodo-2-methyl-phenylamino)-N-methyl-5-nitro-N-phenyl-benzamide
5-Chloro-N-cyclopropyl-2-(4-iodo-2-methyl-phenylamino)-benzamide
5-Fluoro-2-(4-iodo-2-methyl-phenylamino)-N-methyl-N-phenyl-benzamide
N-Allyl-5-fluoro-2-(4-iodo-2-methyl-phenylamino)-benzamide
N-Benzyloxy-5-iodo-2-(4-iodo-2-methyl-phenylamino)-benzamide
5-Fluoro-2-(4-iodo-2-methyl-phenylamino)-N-(4-sulfamoyl-benzyl)-benzamide
N-Allyl-5-chloro-2-(4-iodo-2-methyl-phenylamino)-benzamide
N-Cyclopropyl-2-(4-iodo-2-methyl-phenylamino)-5-nitro-benzamide
5-Bromo-N-cyclopropyl-2-(4-iodo-2-methyl-phenylamino)-benzamide
5-Chloro-2-(4-iodo-2-methyl-phenylamino)-N-methyl-N-phenyl-benzamide
5-Iodo-2-(4-iodo-2-methyl-phenylamino)-N-(4-sulfamoyl-benzyl)-benzamide
5-Bromo-2-(4-iodo-2-methyl-phenylamino)-N-(4-sulfamoyl-benzyl)-benzamide
N-Allyl-2-(4-iodo-2-methyl-phenylamino)-5-nitro-benzamide
2-(4-Iodo-2-methyl-phenylamino)-5-nitro-N-(4-sulfamoyl-benzyl)-benzamide
N-Allyl-5-bromo-2-(4-iodo-2-methyl-phenylamino)-benzamide
5-Fluoro-2-(4-iodo-2-methyl-phenylamino)-N-(3-methyl-benzyl)-benzamide
N-Cyclopropyl-5-iodo-2-(4-iodo-2-methyl-phenylamino)-benzamide
5-Bromo-2-(4-iodo-2-methyl-phenylamino)-N-methyl-N-phenyl-benzamide
N-Benzyloxy-2-(4-iodo-2-methyl-phenylamino)-5-nitro-benzamide
N-Cyclohexyl-5-iodo-2-(4-iodo-2-methyl-phenylamino)-benzamide
N-Allyl-5-iodo-2-(4-iodo-2-methyl-phenylamino)-benzamide
5-Iodo-2-(4-iodo-2-methyl-phenylamino)-N-(3-methyl-benzyl)-benzamide
2-(4-Iodo-2-methyl-phenylamino)-N-(3-methyl-benzyl)-5-nitro-benzamide
5-Iodo-2-(4-iodo-2-methyl-phenylamino)-N-methyl-N-phenyl-benzamide
N-Cyclohexyl-5-fluoro-2-(4-iodo-2-methyl-phenylamino)-benzamide
5-Chloro-N-cyclohexyl-2-(4-iodo-2-methyl-phenylamino)-benzamide
5-Bromo-2-(4-iodo-2-methyl-phenylamino)-N-(3-methyl-benzyl)-benzamide
5-Bromo-N-cyclohexyl-2-(4-iodo-2-methyl-phenylamino)-benzamide
5-Chloro-2-(4-iodo-2-methyl-phenylamino)-N-(3-methyl-benzyl)-benzamide
N-Cyclohexyl-2-(4-iodo-2-methyl-phenylamino)-5-nitro-benzamide
N-Benzyloxy-5-bromo-2-(4-iodo-2-methyl-phenylamino)-benzamide
N-Benzyloxy-5-fluoro-2-(4-iodo-2-methyl-phenylamino)-benzamide
5-Chloro-N-(2-hydroxy-ethyl)-2-(4-iodo-2-methyl-phenylamino)-benzamide
5-Bromo-N-(2-hydroxy-ethyl)-2-(4-iodo-2-methyl-phenylamino)-benzamide
2-(4-Iodo-2-methyl-phenylamino)-N-methyl-5-nitro-N-phenyl-benzamide
5-Chloro-2-(4-iodo-2-methyl-phenylamino)-N-methyl-N-phenyl-benzamide
N-(2-Hydroxy-ethyl)-5-iodo-2-(4-iodo-2-methyl-phenylamino)-benzamide
5-Chloro-N-cyclopropyl-2-(4-iodo-2-methyl-phenylamino)-benzamide
N-Allyl-5-chloro-2-(4-iodo-2-methyl-phenylamino)-benzamide
5-Fluoro-2-(4-iodo-2-methylphenylamino)-N-methyl-N-phenyl-benzamide
N-(2-Hydroxy-ethyl)-2-(4-iodo-2-methyl-phenylamino)-5-nitro-benzamide
5-Fluoro-N-(2-hydroxy-ethyl)-2-(4-iodo-2-methyl-phenylamino)-benzamide
5-Bromo-N-cyclopropyl-2-(4-iodo-2-methyl-phenylamino)-benzamide
N-Cyclopropyl-5-fluoro-2-(4-iodo-2-methyl-phenylamino)-benzamide
5-Fluoro-2-(4-iodo-2-methyl-phenylamino)-N-(4-sulfamoyl-benzyl)-benzamide
N-Cyclopropyl-2-(4-iodo-2-methyl-phenylamino)-5-nitro-benzamide
N-Allyl-5-fluoro-2-(4-iodo-2-methyl-phenylamino)-benzamide
N-Benzyloxy-5-iodo-2-(4-iodo-2-methyl-phenylamino)-benzamide
N-Allyl-5-bromo-2-(4-iodo-2-methyl-phenylamino)-benzamide
5-Bromo-2-(4-iodo-2-methyl-phenylamino)-N-(4-sulfamoyl-benzyl)-benzamide
N-Allyl-2-(4-iodo-2-methyl-phenylamino)-5-nitro-benzamide
4-Fluoro-2-(4-iodo-2-methyl-phenylamino)-benzyl alcohol
[5-Chloro-2-(4-iodo-2-methyl-phenylamino)-phenyl]-methanol
[2-(4-Iodo-2-methyl-phenylamino)-5-nitro-phenyl]-methanol
[5-Bromo-2-(4-iodo-2-methyl-phenylamino)-phenyl]-methanol
N-Allyl-2-(4-iodo-2-methyl-phenylamino)-5-nitro-benzamide.

In another preferred embodiment, the MEK inhibitor is a compound of Formula II

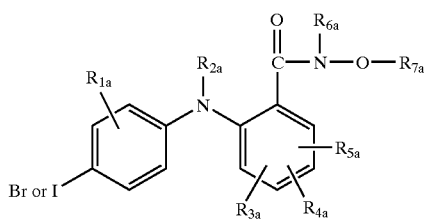

II

In Formula (II), $R_{1a}$ is hydrogen, hydroxy, $C_1$–$C_8$ alkyl, $C_1$–$C_8$ alkoxy, halo, trifluoromethyl, or CN. $R_{2a}$ is hydrogen. Each of $R_{3a}$, $R_{4a}$, and $R_{5a}$ is independently selected from hydrogen, hydroxy, halo, trifluoromethyl, $C_1$–$C_8$ alkyl, $C_1$–$C_8$ alkoxy, nitro, CN, and (O or NH)$_m$—(CH$_2$)$_n$—$R_{9a}$. $R_{9a}$ is hydrogen, hydroxy, CO$_2$H or NR$_{10a}$R$_{11a}$; n is 0–4; and m is 0 or 1. Each of $R_{10a}$ and $R_{11a}$ is independently hydrogen or $C_1$–$C_8$ alkyl, or taken together with the nitrogen to which they are attached can complete a 3- to 10-member cyclic ring optionally containing one, two, or three additional heteroatoms selected from O, S, NH, or N—($C_1$–$C_8$ alkyl). $R_{6a}$ is hydrogen, $C_1$–$C_8$ alkyl, (CO)—($C_1$–$C_8$ alkyl), aryl, aralkyl, or $C_3$–$C_{10}$ cycloalkyl. $R_{7a}$ is hydrogen, $C_1$–$C_8$ alkyl, $C_2$–$C_8$ alkenyl, $C_2$–$C_8$ alkynyl, $C_3$–$C_{10}$ (cycloalkyl or cycloalkyl optionally containing a heteroatom selected from O, S, or NR$_{9a}$). In Formula (II), any of the foregoing any of the foregoing alkyl, alkenyl, aryl, heteroaryl, heterocyclic, and alkynyl groups can be unsubstituted or substituted by halo, hydroxy, $C_1$–$C_6$ alkoxy, amino, nitro, $C_1$–$C_4$ alkylamino, di($C_1$–$C_4$)alkylamino, $C_3$–$C_6$ cycloalkyl, phenyl, phenoxy, $C_3$–$C_5$ heteroaryl or heterocyclic radical, or $C_3$–$C_5$ heteroaryloxy or heterocyclic radical-oxy; or $R_{6a}$ and $R_{7a}$ taken together with the N to which they are attached can complete a 5- to 10-membered cyclic ring, optionally containing one, two, or three additional heteroatoms selected from O, S, or NR$_{10a}$R$_{11a}$. The invention also encompasses pharmaceutically acceptable salts, esters, amides or prodrugs of each of the disclosed compounds.

Preferred embodiments of Formula (II) are those structures wherein: (a) $R_{1a}$ is H, methyl, fluoro, or chloro; (b) $R_{2a}$ is H; $R_{3a}$, $R_{4a}$, and $R_{5a}$ are each H, Cl, nitro, or F; (c) $R_{6a}$ is H; (d) $R_{7a}$ is methyl, ethyl, 2-propenyl, propyl, butyl, pentyl, hexyl, cyclopropylmethyl, cyclobutyl methyl, cyclopropylmethyl, or cyclopropylethyl; (e) the 4' position is I, rather than Br; (f) $R_{4a}$ is F at the 4 position, para to the CO—N—$R_{6a}$—OR$_{7a}$ group and meta to the bridging nitrogen; (f) $R_{3a}$ or $R_{5a}$ is F; (g) at least one of $R_{3a}$, $R_{4a}$, and $R_{5a}$ is F; (h) $R_{1a}$ is methyl or chloro; or (i) or a combination of the above.

In a more preferred embodiment the MEK inhibitor is a compound selected from Formula (II) Compound Table below.

FORMULA (II) COMPOUND TABLE

4-Fluoro-N-hydroxy-2-(4-iodo-2-methyl-phenylamino)-benzamide
4-Fluoro-2-(4-iodo-2-methyl-phenylamino)-N-(methoxy)-benzamide
4-Fluoro-2-(4-iodo-2-methyl-phenylamino)-N-(prop-2-ynyloxy)-benzamide
4-Fluoro-2-(4-iodo-2-methyl-phenylamino)-N-(2-phenoxyethoxy)-benzamide
4-Fluoro-2-(4-iodo-2-methyl-phenylamino)-N-(2-thienylmethoxy)-benzamide
4-Fluoro-2-(4-iodo-2-methyl-phenylamino)-N-(prop-2-enyloxy)-benzamide -continued

FORMULA (II) COMPOUND TABLE

4-Fluoro-2-(4-iodo-2-methyl-phenylamino)-N-(cyclopropylmethoxy)-benzamide
4-Fluoro-2-(4-iodo-2-methyl-phenylamino)-N-(cyclopentoxy)-benzamide
3,4-Difluoro-2-(4-iodo-2-methyl-phenylamino)-N-(3-furylmethoxy)-benzamide
3,4-Difluoro-2-(4-iodo-2-methyl-phenylamino)-N-ethoxy-benzamide
3,4-Difluoro-2-(4-iodo-2-methyl-phenylamino)-N-(but-2-enyloxy)-benzamide
3,4-Difluoro-2-(4-iodo-2-methyl-phenylamino)-N-(cyclopropylmethoxy)-benzamide
3,4-Difluoro-2-(4-iodo-2-methyl-phenylamino)-N-(1-methylprop-2-ynyloxy)-benzamide
3,4-Difluoro-2-(4-iodo-2-methyl-phenylamino)-N-(3-phenylprop-2-ynyloxy)-benzamide
3,4-Difluoro-2-(4-iodo-2-methyl-phenylamino)-N-(3-methyl-5-phenylpent-2-en-4-ynyloxy)-benzamide
3,4-Difluoro-2-(4-iodo-2-methyl-phenylamino)-N-(prop-2-ynyloxy)-benzamide
3,4-Difluoro-2-(4-iodo-2-methyl-phenylamino)-N-(propoxy)-benzamide
3,4-Difluoro-2-(4-iodo-2-methyl-phenylamino)-N-(cyclobutyloxy)-benzamide
3,4-Difluoro-2-(4-iodo-2-methyl-phenylamino)-N-(2-thienylmethoxy)-benzamide
3,4-Difluoro-2-(4-iodo-2-methyl-phenylamino)-N-(2-methyl-prop-2-enyloxy)-benzamide
3,4-Difluoro-2-(4-iodo-2-methyl-phenylamino)-N-(2-phenoxyethoxy)-benzamide
3,4-Difluoro-2-(4-iodo-2-methyl-phenylamino)-N-(but-2-enyloxy)-benzamide
3,4-Difluoro-2-(4-iodo-2-methyl-phenylamino)-N-(but-3-ynyloxy)-benzamide
3,4-Difluoro-2-(4-iodo-2-methyl-phenylamino)-N-(cyclopentyloxy)-benzamide
3,4-Difluoro-2-(4-iodo-2-methyl-phenylamino)-N-(3-(2-fluorophenyl)-prop-2-ynyloxy)-benzamide
5-Bromo-3,4-difluoro-N-hydroxy-2-(4-iodo-2-methyl-phenylamino)-benzamide
5-Bromo-3,4-difluoro-2-(4-iodo-2-methyl-phenylamino)-N-(n-propoxy)-benzamide
5-Bromo-3,4-difluoro-N-(furan-3-ylmethoxy)-2-(4-iodo-2-methyl-phenylamino)-benzamide
5-Bromo-N-(but-2-enyloxy)-3,4-difluoro-2-(4-iodo-2-methyl-phenylamino)-benzamide
5-Bromo-N-butoxy-3,4-difluoro-2-(4-iodo-2-methyl-phenylamino)-benzamide
5-Bromo-3,4-difluoro-2-(4-iodo-2-methyl-phenylamino)-N-(3-methyl-but-2-enyloxy)-benzamide
5-Bromo-3,4-difluoro-2-(4-iodo-2-methyl-phenylamino)-N-(3-methyl-pent-2-en-4-ynyloxy)-benzamide
5-Bromo-3,4-difluoro-2-(4-iodo-2-methyl-benzyl)-N-[5-(3-methoxyphenyl)-3-methyl-pent-2-en-4-ynyloxy]-benzamide
5-Bromo-3,4-difluoro-2-(4-iodo-2-methyl-phenylamino)-N-(prop-2-ynyloxy)-benzamide
5-Bromo-3,4-difluoro-2-(4-iodo-2-methyl-phenylamino)-N-[3-(3-methoxy-phenyl)-prop-2-ynyloxy]-benzamide
5-Bromo-3,4-difluoro-2-(4-iodo-2-methyl-phenylamino)-N-(thiopen-2-ylmethoxy)-benzamide
5-Bromo-3,4-difluoro-2-(4-iodo-2-methyl-phenylamino)-N-(pyridin-3-ylmethoxy)-benzamide
5-Bromo-3,4-difluoro-2-(4-iodo-2-methyl-phenylamino)-N-(3-(2-fluorophenyl)-prop-2-ynyloxy)-benzamide
5-Bromo-3,4-difluoro-2-(4-iodo-2-methyl-phenylamino)-N-(ethoxy)-benzamide
5-Bromo-3,4-difluoro-2-(4-iodo-2-methyl-phenylamino)-N-(cyclopropylmethoxy)-benzamide
5-Bromo-3,4-difluoro-2-(4-iodo-2-methyl-phenylamino)-N-(isopropoxy-benzamide
5-Bromo-3,4-difluoro-2-(4-iodo-2-methyl-phenylamino)-N-but-3-ynyloxy)-benzamide
5-Chloro-N-hydroxy-2-(4-iodo-2-methyl-phenylamino)-benzamide
5-Chloro-2-(4-iodo-2-methyl-phenylamino)-N-(tetrahydro-pyran-2-yloxy)-benzamide
5-Chloro-2-(4-iodo-2-methyl-phenylamino)-N-methoxy-benzamide
4-Bromo-2-(4-iodo-2-methyl-phenylamino)-N-phenylmethoxy-benzamide
4-Fluoro-2-(4-iodo-2-methyl-phenylamino)-N-phenylmethoxy-benzamide
5-Fluoro-N-hydroxy-2-(4-iodo-2-methyl-phenylamino)-benzamide
5-Iodo-2-(4-iodo-2-methyl-phenylamino)-N-phenylmethoxy-benzamide

FORMULA (II) COMPOUND TABLE

5-Fluoro-2-(4-iodo-2-methyl-phenylamino)-N-tetrahydropyran-2-yloxy)-benzamide
3,4-Difluoro-2-(4-bromo-2-methyl-phenylamino)-N-(3-phenylprop-2-ynyloxy)-benzamide
3,4-Difluoro-2-(4-bromo-2-methyl-phenylamino)-N-(3-furylmethoxy)-benzamide
3,4-Difluoro-2-(4-bromo-2-methyl-phenylamino)-N-(2-thienylmethoxy)-benzamide
3,4-Difluoro-2-(4-bromo-2-methyl-phenylamino)-N-(but-3-ynyloxy)-benzamide
3,4-Difluoro-2-(4-bromo-2-methyl-phenylamino)-N-(2-methyl-prop-2-enyloxy)-benzamide
3,4-Difluoro-2-(4-bromo-2-methyl-phenylamino)-N-(but-2-enyloxy)-benzamide
3,4-Difluoro-2-(4-bromo-2-methyl-phenylamino)-N-(methoxy)-benzamide
3,4-Difluoro-2-(4-bromo-2-methyl-phenylamino)-N-(ethoxy)-benzamide
3,4-Difluoro-2-(4-bromo-2-methyl-phenylamino)-N-(cyclobutoxy)-benzamide
3,4-Difluoro-2-(4-bromo-2-methyl-phenylamino)-N-(isopropoxy)-benzamide
3,4-Difluoro-2-(4-bromo-2-methyl-phenylamino)-N-(2-phenoxyethoxy)-benzamide
3,4-Difluoro-2-(4-bromo-2-methyl-phenylamino)-N-(cyclopropylmethoxy)-benzamide
3,4-Difluoro-2-(4-bromo-2-methyl-phenylamino)-N-(n-propoxy)-benzamide
3,4-Difluoro-2-(4-bromo-2-methyl-phenylamino)-N-(1-methyl-prop-2-ynyloxy)-benzamide
3,4-Difluoro-2-(4-bromo-2-methyl-phenylamino)-N-(3-(3-fluorophenyl)-prop-2-ynyloxy)-benzamide
3,4-Difluoro-2-(4-bromo-2-methyl-phenylamino)-N-(4,4-dimethylpent)-2-ynyloxy-benzamide
3,4-Difluoro-2-(4-bromo-2-methyl-phenylamino)-N-(cyclopentoxy)-benzamide
3,4,5-Trifluoro-N-hydroxy-2-(4-iodo-2-methyl-phenylamino)-benzamide
5-Chloro-3,4-difluoro-N-hydroxy-2-(4-iodo-2-methyl-phenylamino)-benzamide
5-Bromo-3,4-difluoro-2-(2-fluoro-4-iodo-phenylamino)-N-hydroxy-benzamide
N-Hydroxy-2-(4-iodo-2-methyl-phenylamino)-4-nitro-benzamide
3,4,5-Trifluoro-2-(2-fluoro-4-iodo-phenylamino)-N-hydroxy-benzamide
5-Chloro-3,4-difluoro-2-(2-fluoro-4-iodo-phenylamino)-N-hydroxy-benzamide
5-Bromo-2-(2-chloro-4-iodo-phenylamino)-3,4-difluoro-N-hydroxy-benzamide
2-(2-Fluoro-4-iodo-phenylamino)-N-hydroxy-4-nitro-benzamide
2-(2-Chloro-4-iodo-phenylamino)-3,4,5-trifluoro-N-hydroxy-benzamide
5-Chloro-2-(2-chloro-4-iodo-phenylamino)-3,4-difluoro-N-hydroxy-benzamide
5-Bromo-2-(2-bromo-4-iodo-phenylamino)-3,4-difluoro-N-hydroxy-benzamide
2-(2-Chloro-4-iodo-phenylamino)-N-hydroxy-4-methyl-benzamide
2-(2-Bromo-4-iodo-phenylamino)-3,4,5-trifluoro-N-hydroxy-benzamide
2-(2-Bromo-4-iodo-phenylamino)-5-chloro-3,4-difluoro-N-hydroxy-benzamide
2-(2-Bromo-4-iodo-phenylamino)-N-hydroxy-4-nitro-benzamide
4-Fluoro-2-(2-fluoro-4-iodo-phenylamino)-N-hydroxy-benzamide
3,4-Difluoro-2-(2-fluoro-4-iodo-phenylamino)-N-hydroxy-benzamide
2-(2-Chloro-4-iodo-phenylamino)-4-fluoro-N-hydroxy-benzamide
2-(2-Chloro-4-iodo-phenylamino)-3,4-difluoro-N-hydroxy-benzamide
2-(2-Bromo-4-iodo-phenylamino)-4-fluoro-N-hydroxy-benzamide
2-(2-Bromo-4-iodo-phenylamino)-3,4-difluoro-N-hydroxy-benzamide
N-Cyclopropylmethoxy-3,4,5-trifluoro-2-(4-iodo-2-methyl-phenylamino)-benzamide
5-Chloro-N-cyclopropylmethoxy-3,4-difluoro-2-(4-iodo-2-methyl-phenylamino)-benzamide
5-Bromo-N-cyclopropylmethoxy-3,4-difluoro-2-(2-fluoro-4-iodo-phenylamino)-benzamide
N-Cyclopropylmethoxy-2-(4-iodo-2-methyl-phenylamino)-4-nitro-benzamide
N-Cyclopropylmethoxy-3,4,5-trifluoro-2-(2-fluoro-4-iodo-phenylamino)-benzamide
5-Chloro-N-cyclopropylmethoxy-3,4-difluoro-2-(2-fluoro-4-iodo-phenylamino)-benzamide
5-Bromo-2-(2-chloro-4-iodo-phenylamino)-N-cyclopropylmethoxy-3,4-difluoro-benzamide
N-Cyclopropylmethoxy-2-(2-fluoro-4-iodo-phenylamino)-4-nitro-benzamide
2-(2-Chloro-4-iodo-phenylamino)-N-cyclopropylmethoxy-3,4,5-trifluoro-benzamide
5-Chloro-2-(2-chloro-4-iodo-phenylamino)-N-cyclopropylmethoxy-3,4-difluoro-benzamide
5-Bromo-2-(2-bromo-4-iodo-phenylamino)-N-ethoxy-3,4-difluoro-benzamide
2-(2-Chloro-4-iodo-phenylamino)-N-ethoxy-4-nitro-benzamide
2-(2-Bromo-4-iodo-phenylamino)-N-cyclopropylmethoxy-3,4,5-trifluoro-benzamide
2-(2-Bromo-4-iodo-phenylamino)-5-chloro-N-cyclopropylmethoxy-3,4,-difluoro-benzamide
2-(2-Bromo-4-iodo-phenylamino)-N-cyclopropylmethoxy-4-nitro-benzamide
N-Cyclopropylmethoxy-4-fluoro-2-(2-fluoro-4-iodo-phenylamino)-benzamide
N-Cyclopropylmethoxy-3,4-difluoro-2-(2-fluoro-4-iodo-phenylamino)-benzamide
2-(2-Chloro-4-iodo-phenylamino)-N-cyclopropylmethoxy-4-fluoro-benzamide
2-(2-Chloro-4-iodo-phenylamino)-N-cyclopropylmethoxy-3,4-difluoro-benzamide
2-(2-Bromo-4-iodo-phenylamino)-N-cyclopropylmethoxy-4-fluoro-benzamide
2-(2-Bromo-4-iodo-phenylamino)-N-cyclopropylmethoxy-3,4-difluoro-benzamide.

In the most preferred embodiment of this invention, a compound selected from the following is administered to a patient (ie, a mammal) in an amount that is effective to prevent or treat rheumatoid arthritis or osteoarthritis:

2-(2-Chloro4-iodophenylamino)-N-cyclopropylmethoxy-3,4-difluorobenzamide (PD184352); 2-(2-Methyl-4-iodophenylamino)-N-hydroxy-4-fluorobenzamide (PD170611); 2-(2-Methyl-4-iodophenylamino)-N-hydroxy-3,4-difluoro-5-bromobenzamide(PD171984); 2-(2-Methyl-4-iodophenylamino)-N-cyclopropylmethoxy-3,4-difluoro-5-bromobenzamide (PD177168); 2-(2-Methyl-4-iodophenylamino)-N-cyclobutylmethoxy-3,4-difluoro-5-bromobenzamide (PD 180841); 2-(2-Chloro-4-iodophenylamino)-N-cyclopropylmethoxy-3,4-difluoro-5-bromobenzamide (PD 184161); 2-(2-Chloro-4-iodophenylamino)-N-hydroxy-3,4-difluoro-5-bromobenzamide (PD184386); 2-(2-Chloro4-iodophenylamino)-N-cyclobutylmethoxy-3,4-difluorobenzamide (PD185625); 2-(2-Chloro-4-iodophenylamino)-N-hydroxy-4-fluorobenzamide(PD 185848); 2-(2-Methyl-4-iodophenylamino)-N-hydroxy-3,4-difluorobenzamide (PD 188563); 2-(2-Methyl-4-iodophenylamino)-N-cyclopropylmethoxy-3,4,5-trifluorobenzamide (PD 198306); and 2-(2-Chloro-4-iodophenylamino)-N-cyclopropylmethoxy-4-fluorobenzamide (PD 203311); and the benzoic acid derivatives thereof. For example, the benzoic acid derivative of PD 198306 is 2-(2-Methyl-4-iodophenylamino)-3,4,5-trifluorobenzoic acid.

Additional preferred compounds include 2-(2-chloro4-iodophenylamino)-5-chloro-N-cyclopropylmethoxy-3,4-difluorobenzamide (PD 297189), 2-(4-iodophenylamino)-N-cyclopropylmethoxy-5-chloro-3,4-difluorobenzamide (PD 297190), 2-(4-iodophenylamino)-5-chloro-3,4-difluorobenzoic acid (PD 296771), 2-(2-chloro4-iodophenylamino)-5-chloro-3,4-difluorobenzoic acid (PD 296770), 5-chloro-3,4-difluoro-2-(4-iodo-2-methylphenylamino)-benzoic acid (PD 296767); and 5-chloro-N-cyclopropylmethoxy-3,4-difluoro-2-(4-iodo-2-methylphenylamino)-benzamide (PD 298127).

The invention further provides methods of synthesis and synthetic intermediates.

Other features and advantages of the invention are apparent from the detailed description, examples, and claims set forth.

In a further preferred embodiment of this invention, a mitotic inhibitor is administered to a patient suffering from cancer and in need of treatment in combination with a selective MEK inhibitor selected from: 2-(2-Chloro-4-iodophenylamino)-N-cyclopropylmethoxy-3,4-difluorobenzamide (PD184352); 2-(2-Methyl-4-iodophenylamino)-N-hydroxy-4-fluorobenzamide (PD 170611); 2-(2-Methyl-4-iodophenylamino)-N-hydroxy-3,4-difluoro-5-bromobenzamide (PD 171984), a more preferred compound; 2-(2-Methyl-4-iodophenylamino)-N-cyclopropylmethoxy-3,4-difluoro-5-bromobenzamide (PD 177168); 2-(2-Methyl-4-iodophenylamino)-N-cyclobutylmethoxy-3,4-difluoro-5-bromobenzamide (PD 180841); 2-(2-Chloro4-iodophenylamino)-N-cyclopropylmethoxy-3,4-difluoro-5-bromobenzamide (PD 184161); 2-(2-Chloro-4-iodophenylamino)-N-hydroxy-3,4-difluoro-5-bromobenzamide (PD 184386); 2-(2-Chloro-4-iodophenylamino)-N-cyclobutylmethoxy-3,4-difluorobenzamide (PD 185625); 2-(2-Chloro4-iodophenylamino)-N-hydroxy4-fluorobenzamide (PD 185848); 2-(2-Methyl4-iodophenylamino)-N-hydroxy-3,4-difluorobenzamide (PD 188563); 2-(2-Methyl4-iodophenylamino)-N-cyclopropylmethoxy-3,4,5-trifluorobenzamide (PD 198306); and 2-(2-Chloro-4-iodophenylamino)-N-cyclopropylmethoxy-4-fluorobenzamide (PD 203311); and the benzoic acid derivatives thereof. For example, the benzoic acid derivative of PD 198306 is 2-(2-Methyl-4-iodophenylamino)-3,4,5-trifluorobenzoic acid.

DETAILED DESCRIPTION OF THE INVENTION

This invention provides a method of preventing or treating asthma in a patient which comprises administering to a patient suffering from asthma and in need of treatment, or to a patient at risk for developing an asthmatic attack, an anti-asthmatic effective amount of a MEK inhibitor. The invention provides a method of preventing and treating all forms of asthma and relieving the symptoms that accompany the disease. The invention is preferably practiced by administering a phenyl amine MEK inhibitor of Formula I or Formula II. Such MEK phenyl amine compounds are specific MEK 1 and MEK 2 inhibitors, meaning that they inhibit these enzymes without inhibiting other enzymes to a great extent.

The compounds of the present invention, which can be used to treat septic shock, are MEK inhibitors. A MEK inhibitor is a compound that shows MEK inhibition when tested in the assays titled "Enzyme Assays" in U.S. Pat. No. 5,525,625, column 6, beginning at line 35. The complete disclosure of U.S. Pat. No. 5,525,625 is hereby incorporated by reference. An example of a MEK inhibitor is 2-(2-amino-3-methoxyphenyl)-4-oxo-4H-[1]benzopyran. Specifically, a compound is a MEK inhibitor if a compound shows activity in the assay titled "Cascade Assay for Inhibitors of the MAP Kinase Pathway," column 6, line 36 to column 7, line 4 of the U.S. Pat. No. 5,525,625 and/or shows activity in the assay titled "In Vitro MEK Assay" at column 7, lines 4 to 27 of the above-referenced patent.

A. Terms

Some of the terms used herein are defined below and by their usage throughout this disclosure.

The term "patient" means all animals including humans. Examples of patients include humans, cows, dogs, cats, goats, sheep, horses, and pigs. The mammals to be treated according to this invention are patients who have developed asthma and are suffering from the symptoms associated with disease, or who are at risk for developing the disease, for example having a family history of asthma. Those skilled in the medical art are readily able to identify individual patients, particularly children, who are afflicted with asthma, as well as those who are susceptible to developing the disease.

As used herein, the term "aryl" means a cyclic, bicyclic, or tricyclic aromatic ring moiety having from five to twelve carbon atoms. Examples of typical aryl groups include phenyl, naphthyl, and fluorenyl. The aryl may be substituted by one, two, or three groups selected from fluoro, chloro, bromo, iodo, alkyl, hydroxy, alkoxy, nitro, amino, alkylamino, or dialkylamino. Typical substituted aryl groups include 3-fluorophenyl, 3,5-dimethoxyphenyl, 4-nitronaphthyl, 2-methyl-4-chloro-7-aminofluorenyl, and the like.

The term "aryloxy" means an aryl group bonded through an oxygen atom, for example phenoxy, 3-bromophenoxy, naphthyloxy, and 4-methyl-1-fluorenyloxy.

"Heteroaryl" means a cyclic, bicyclic, or tricyclic aromatic ring moiety having from four to eleven carbon atoms and one, two, or three heteroatoms selected from O, S, or N. Examples include furyl, thienyl, pyrrolyl, pyrazolyl, imidazolyl, triazolyl, thiazolyl, oxazolyl, xanthenyl, pyronyl, indolyl, pyrimidyl, naphthyridyl, pyridyl, benzinnidazolyl, and triazinyl. The heteroaryl groups can be unsubstituted or substituted by one, two, or three groups selected from fluoro, chloro, bromo, iodo, alkyl, hydroxy, alkoxy, nitro, amino, alkylamino, or dialkylamino. Examples of substituted heteroaryl groups include chloropyranyl, methylthienyl, fluoropyridyl, amino-1,4-benzisoxazinyl, nitroisoquinolinyl, and hydroxyindolyl.

The heteroaryl groups can be bonded through oxygen to make heteroaryloxy groups, for example thienyloxy, isothiazolyloxy, benzofuranyloxy, pyridyloxy, and 4-methylisoquinolinyloxy.

The term "alkyl" means straight and branched chain aliphatic groups. Typical alkyl groups include methyl, ethyl, isopropyl, tert.-butyl, 2,3-dimethylhexyl, and 11-dimethylpentyl. The alkyl groups can be unsubstituted or substituted by halo, hydroxy, alkoxy, amino, alkylamino, dialkylamino, cycloalkyl, aryl, aryloxy, heteroaryl, or heteroaryloxy, as those terms are defined herein. Typical substituted alkyl groups include chloromethyl, 3-hydroxypropyl, 2-dimethylaminobutyl, and 2-(hydroxymethylamino)ethyl. Examples of aryl and aryloxy substituted alkyl groups include phenylmethyl, 2-phenylethyl, 3-chlorophenylmethyl, 1,1-dimethyl-3-(2-nitrophenoxy)butyl, and 3,4,5-trifluoronaphthylmethyl. Examples of alkyl groups substituted by a heteroaryl or heteroaryloxy group include thienylmethyl, 2-furylethyl, 6-furyloxyoctyl, 4-methylquinolyloxymethyl, and 6-isothiazolylhexyl. Cycloalkyl substituted alkyl groups include cyclopropylmethyl, 2-cyclohexyethyl, piperidyl-2-methyl, 2-(piperidin-1-yl)-ethyl, 3-(morpholin-4-yl)propyl.

"Alkenyl" means a straight or branched carbon chain having one or more double bonds. Examples include but-2-enyl, 2-methyl-prop-2-enyl, 1,1-dimethyl-hex-4-enyl, 3-ethyl-4-methyl-pent-2-enyl, and 3-isopropyl-pent-4-enyl. The alkenyl groups can be substituted with halo, hydroxy, alkoxy, amino, alkylamino, dialkylamino, aryl, aryloxy, heteroaryl, or heteroyloxy, for example 2-bromoethenyl, 3-hydroxy-2-butenyl, 1-aminoethenyl, 3-phenylprop-2- enyl, 6-thienyl-hex-2-enyl, 2-furyloxy-but-2-enyl, and 4-naphthyloxy-hex-2-enyl. "Alkynyl" means a straight or branched carbon chain having at least one triple bond. Typical alkynyl groups include prop-2-ynyl, 2-methyl-hex-5-ynyl, 3,4-dimethyl-hex-5-ynyl, and 2-ethyl-but-3-ynyl. The alkynyl groups can be substituted as the alkyl and alkenyl groups, for example, by aryl, aryloxy, heteroaryl, or heteroaryloxy, for example 4-(2-fluorophenyl)-but-3-ynyl, 3-methyl-5-thienylpent-4-ynyl, 3-phenoxy-hex-4-ynyl, and 2-furyloxy-3-methyl-hex-4-ynyl.

The alkenyl and alkynyl groups can have one or more double bonds or triple bonds, respectively, or a combination of double and triple bonds. For example, typical groups having both double and triple bonds include hex-2-en-4-ynyl, 3-methyl-5-phenylpent-2-en-4-ynyl, and 3-thienyloxy-hex-3-en-5-ynyl.

The term "cycloalkyl" means a nonaromatic ring or fused rings. Examples include cyclopropyl, cyclobutyl, cyclopenyl, cyclooctyl, bicycloheptyl, adamantyl, and cyclohexyl. The ring can optionally contain one, two, or three heteroatoms selected from O, S, or N. Such groups include tetrahydrofuryl, tetrahydropyrrolyl, octahydrobenzofuranyl, morpholinyl, piperazinyl, pyrrolidinyl, piperidinyl, octahydroindolyl, and octahydrobenzothiofuranyl. The cycloalkyl groups can be substituted with the same substituents as an alkyl and alkenyl groups, for example, halo, hydroxy, aryl, and heteroaryloxy. Examples include 3-hydroxycyclohexyl, 2-aminocyclopropyl, 2-phenylpyrrolidinyl, and 3-thienylmorpholine-1-yl.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth ($1/50$) that of its $IC_{50}$ for one of the above-named other enzymes. Preferably, a selective inhibitor has an $IC_{50}$ that is at least $1/100$, more preferably $1/500$, and even more preferably $1/1000$, $1/5000$, or less than that of its $IC_{50}$ or one or more of the above-named enzymes.

B. Administration and Formulation

The MEK inhibitors of the present method can be administered to a patient as part of a pharmaceutically acceptable composition. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar—agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalamic formulations, eye ointments, powders, and solutions are also contemplated as being within the scope of this invention.

The compounds of the present method can be administered to a patient at dosage levels in the range of about 0.1 to about 1000 mg per day. For a normal human adult having a body weight of about 70 kg, a dosage in the range of about 0.01 to about 100 mg per kg of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

The compounds of the present method can be administered as pharmaceutically acceptable salts, esters, amides, or prodrugs. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Druz Design*, ed. Edward B. Roche, American Pharmaceutical Association and Pergamon Press, 1987, both of which are incorporated herein by reference.

In addition, the compounds of the present method can exist in unsolvated as well as solvated forms with pharmaceutically acceptable solvents such as water, ethanol, and the like. In general, the solvated forms are considered equivalent to the unsolvated forms for the purposes of the present invention.

Some of the compounds of the present method can exist in different stereoisometric forms by virtue of the presence of chiral centers. It is contemplated that all stereoisometric forms of the compounds as well as mixtures thereof, including racemic mixtures, form part of this invention.

C. Synthesis

The examples presented below are intended to illustrate particular embodiments of the invention and are not intended to limit the scope of the specification, including the claims, in any way. After the priority date of the present disclosure, related syntheses and MEK inhibition data were also published in WO 99/01421 and WO 99/01426, hereby incorporated by reference.

The 2-(4-bromo and 4-iodo phenylamino)-benzoic acid derivatives of Formula I can be prepared from commercially available starting materials utilizing synthetic methodologies well-known to those skilled in organic chemistry. A typical synthesis is carried out by reacting a 4-bromo or 4-iodo aniline with a benzoic acid having a leaving group at the 2-position to give a 2-(phenylamino)-benzoic acid. This process is depicted in Scheme 1.

Scheme 1

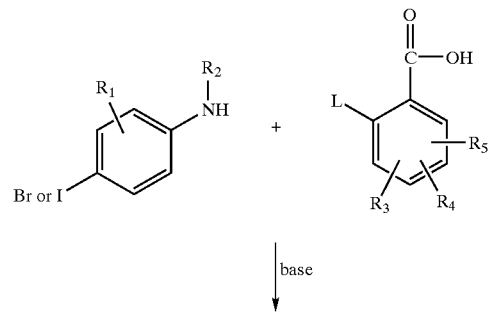

17

-continued

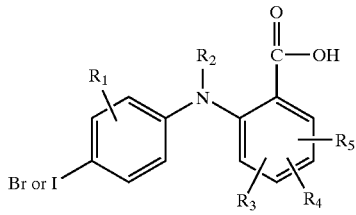

where L is a leaving group, for example halo such as fluoro.

The reaction of aniline and the benzoic acid derivative generally is accomplished by mixing the benzoic acid with an equimolar quantity or excess of the aniline in an unreactive organic solvent such as tetrahydrofuran or toluene, in the presence of a base such as lithium diisopropylamide, n-butyl lithium, sodium hydride, triethylamine, and Hunig's base. The reaction generally is carried out at a temperature of about −78° C. to about 100° C., and normally is complete within about 2 hours to about 4 days. The product can be isolated by removing the solvent, for example by evaporation under reduced pressure, and further purified, if desired, by standard methods such as chromatography, crystallization, or distillation.

The 2-(phenylamino)-benzoic acid (e.g., Formula I, where $R_7$ is hydrogen) can be reacted with an organic or inorganic base such as pyridine, triethylamine, calcium carbonate, or sodium hydroxide to produce a pharmaceutically acceptable salt. The free acids can also be reacted with an alcohol of the formula $HOR_7$ (where $R_7$ is other than hydrogen, for example methyl) to produce the corresponding ester. Reaction of the benzoic acid with an alcohol can be carried out in the presence of a coupling agent. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)- phosphonium hexafluorophosphate (PyBrOP), and (benzotriazolyloxy) tripyrrolidino phosphonium hexafluorophosphate (PyBOP). The phenylamino benzoic acid and alcohol derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

The benzamides of the invention, Formula I where Z is $CONR_6R_7$, are readily prepared by reacting the foregoing benzoic acids with an amine of the formula $HNR_6R_7$. The reaction is carried out by reacting approximately equimolar quantities of the benzoic acid and amine in an unreactive organic solvent in the presence of a coupling reagent. Typical solvents are chloroform, dichloromethane, tetrahydrofuran, benzene, toluene, and xylene. Typical coupling reagents include DCC, EEDQ, PyBrOP, and PyBOP. The reaction is generally complete after about 10 minutes to about 2 hours when carried out at a temperature of about 0° C. to about 60° C. The product amide is readily isolated by removing the reaction solvent, for instance by evaporation, and further purification can be accomplished by normal methods such as chromatography, crystallization, or distillation. The hydrazides ($z=CONHNR_{10}R_{11}$) are similarly

18 prepared by coupling a benzoic acid with a hydrazine of the formula $H_2HNR_{10}R_{11}$.

The benzyl alcohols of the invention, compounds of Formula I where Z is $CH_2OR_6$ and $R_6$ is hydrogen, are readily prepared by reduction of the corresponding benzoic acid according to the following Scheme 2.

Scheme 2

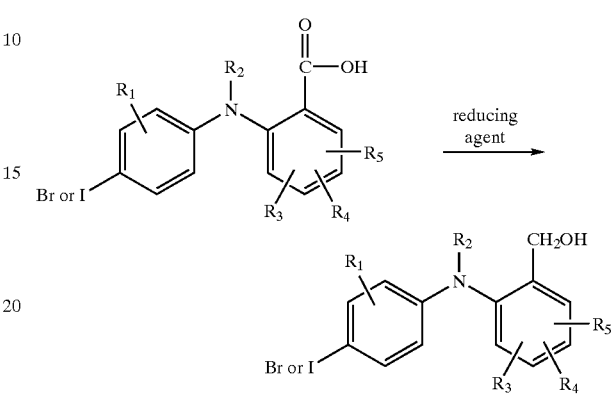

Typical reducing agents commonly employed include borane in tetrahydrofuran. The reduction normally is carried out in an unreactive organic solvent such as tetrahydrofuran, and generally is complete within about 2 hours to about 24 hours when conducted at a temperature of about 0° C. to about 40° C.

The following detailed examples illustrate specific compounds provided by this invention.

EXAMPLE 1

4-Fluoro-2-(4-iodo-2-methylphenylamino)benzoic Acid

To a stirring solution comprised of 3.16 g (0.0133 mol) of 2-amino-5-iodotoluene in 5 mL of tetrahydrofuran at −78° C. was added 10 mL (0.020 mol) of a 2.0 M lithium diisopropylamide in tetrahydrofuran/heptane/ethenylbenzene (Aldrich) solution. The resulting green suspension was stirred vigorously for 15 minutes, after which time a solution of 1.00 g (0.00632 mol) of 2,4-difluorobenzoic acid in 10 mL of tetrahydrofuran was added. The reaction temperature was allowed to increase slowly to room temperature, at which temperature it was stirred for 2 days. The reaction mixture was concentrated. Aqueous HCl (10%) was added to the concentrate, and the solution was extracted with dichloromethane. The organic phase was dried ($MgSO_4$) and then boiled over a steambath to low volume and cooled to room temperature. The off-white fibers were collected by vacuum filtration, rinsed with hexanes, and vacuum-oven dried. (76° C.; ca. 10 mm of Hg) to afford 1.10 g (47%) of the desired material;

mp 224–229.5° C.; $^1$H NMR (400 MHz; DMSO): δ 9.72 (s, 1H), 7.97 (dd, 1H, J=7.0, 8.7 Hz), 7.70 (d, 1H, J=1.5 Hz), 7.57 (dd, 1H, J=8.4, 1.9 Hz), 7.17 (d, 1H, J=8.2 Hz), 6.61–6.53 (m, 2H), 2.18 (s, 3H); $^{13}$C NMR (100 MHz; DMSO): δ 69.87, 167.60, 165.12, 150.17, 150.05, 139.83, 138.49, 136.07, 135.31, 135.20, 135.07, 125.60, 109.32, 105.09, 104.87, 99.72, 99.46, 89.43, 17.52; $^{19}$F NMR (376 MHz; DMSO): δ −104.00 to −104.07 (m); IR (KBr) 1670 (C=O stretch) $cm^{-1}$; MS (CI) M+1=372. Analysis calculated for $C_{14}H_{11}FINO_2$: C, 45.31; H, 2.99; N, 3.77. Found: C, 45.21; H, 2.77; N, 3.64.

EXAMPLES 2–30

By following the general procedure of Example 1, the following benzoic acids and salts of Formula (I) were prepared.

| Example No. | Compound | MP ° C. |
|---|---|---|
| 2 | 3,4,5-Trifluoro-2-(4-iodo-2-methyl-phenylamino)-benzoic acid | 206–210 |
| 3 | 3,4-Difluoro-2-(4-iodo-2-methyl-phenylamino)-benzoic acid | 240.5–244.5 |
| 4 | 5-Bromo-3,4-difluoro-2-(4-iodo-2-methyl-phenylamino)-benzoic acid | 259.5–262 |
| 5 | 5-Chloro-2-(2-chloro-4-iodo-phenylamino)-benzoic acid | 255–260 |
| 6 | 5-Chloro-2-(4-iodo-2-methyl-phenylamino-benzoic acid | 234–238 |
| 7 | Sodium 5-Chloro-2-(4-iodo-2-methyl-phenylamino)-benzoate | 310–320 DEC |
| 8 | 5-Bromo-2-(4-iodo-2-methyl-phenylamino)-benzoic acid | 239.5–240 |
| 9 | 2-(2-Chloro-4-iodo-phenylamino)-5-nitro-benzoic acid | 289–293 |
| 10 | 4-Fluoro-2-(3-fluoro-4-iodo-2-methyl-phenylamino)-benzoic acid | 233–235 |
| 11 | 2-(4-Iodo-2-methyl-phenylamino)-5-nitro-benzoic acid | 264–267 |
| 12 | 2-(2-Fluoro-4-iodo-phenylamino)-5-nitro-benzoic acid | 256–258 |
| 13 | 2-(4-Bromo-2-methyl-phenylamino)-4-fluoro-benzoic acid | 218.5–220 |
| 14 | 2-(2-Bromo-4-iodo-phenylamino)-5-nitro-benzoic acid | 285–288 DEC |
| 15 | 2-(4-Bromo-2-methyl-phenylamino)-3,4-difluoro-benzoic acid | 230–234 |
| 16 | 3-Fluoro-2-(4-iodo-2-methyl-phenylamino)-benzoic acid | 218–221 |
| 17 | 3,4-Difluoro-2-(4-iodo-2-methoxy-phenylamino)-benzoic acid | 230–233 |
| 18 | 4-Chloro-2-(4-iodo-2-methyl-phenylamino)-benzoic acid | 245–255 DEC |
| 19 | 2-(4-Iodo-2-methyl-phenylamino)-benzoic acid | 218–223 |
| 20 | 5-Fluoro-2-(4-iodo-2-methyl-phenylamino)-benzoic acid | 243–46 |
| 21 | 5-Iodo-2-(4-iodo-2-methyl-phenylamino)-benzoic acid | 241–245 |
| 22 | 2,3,5-Trifluoro-4-(4-iodo-2-methyl-phenylamino)-benzoic acid | 218–222 |
| 23 | 4-Fluoro-2-(3-chloro-4-iodo-2-methyl-phenylamino)-benzoic acid | 248–252.5 |
| 24 | 2-(4-Iodo-phenylamino)-5-methoxy-benzoic acid | 208–211 |
| 25 | 3-Chloro-2-(2-chloro-iodo-phenylamino)-benzoic acid | 232–233 |
| 26 | 2-Fluoro-6-(4-iodo-2-methyl-phenylamino)-benzoic acid | 179–182 |
| 27 | 4-Fluoro-2-(2,3-dimethyl-4-iodo-2-methyl-phenylamino)benzoic acid | 258–261 |
| 28 | 5-Methyl-2-(4-iodo-2-methyl-phenylamino)-benzoic acid | 209.5–211 |
| 29 | 2-Chloro-6-(4-iodo-2-methyl-phenylamino)-benzoic acid | 171–175 |
| 30 | 2-(4-Iodo-2-methyl-phenylamino)-4-nitro-benzoic acid | 251–263 |

EXAMPLE 31

N-(2-hydroxyethyl)-2-(4-iodo-2-methyl-phenylamino)-benzamide

To a stirring solution comprised of 0.1020 g (0.2632 mmol) of 5-chloro-2-(4-iodo-2-methyl-phenylamino) benzoic acid, 0.1 mL (1.7 mmol) of ethanolamine, and 0.05 mL (0.29 mmol) of diisopropylethylamine in 5 mL of a 1:1 (v/v) tetrahydrofuran-dichloromethane solution was added 0.15 g (0.29 mmol) of solid BOP powder directly. The reaction mixture was stirred at room temperature overnight. The solvent was removed in vacuo. The crude residue was partioned between ether (50 mL) and 10% aqueous hydrochloric acid (50 mL). The organic phase was washed with 10% aqueous sodium hydroxide (50 mL), dried (MgSO$_4$) and concentrated in vacuo to afford a yellow-brown oil which was crystallized from hexanes-ether to afford 0.0831 g (73%) of a green-yellow powder; mp 120–121° C.;

$^1$H NMR (400 MHz; CDCl$_3$): δ 9.11 (s, 1H), 7.56 (d, 1H, J=1.4 Hz), 7.46–7.41 (m, 2H), 7.20 (dd, 1H, J=8.9, 2.4 Hz), 7.00 (t, 2H, J=9.6 Hz), 6.55 (broad t, 1H), 2H, J=5.0 Hz), 3.61 (dd, 2H, J=10.1, 5.5 Hz), 2.23 (s, 3H), 1.56 (broad s, 1H); IR (KBr) 3297 (O—H stretch), 1627 (C=O stretch) cm$^{-1}$; MS (CI) M+1=431. Analysis calculated for C$_{16}$H$_{16}$ClIN$_2$$_{O2}$: C, 44.62; H, 3.74; N, 6.50. Found: 44.63; H, 3.67; N, 6.30.

EXAMPLES 32–48

By following the general procedure of Example 31, the following benzamides were prepared by reacting the corresponding benzoic acid with the corresponding amine.

| Example No. | Compound | MP ° C. |
|---|---|---|
| 32 | 4-Methoxy-N-(4-methoxy-phenyl)-3-nitro-benzamide | 153.5–156 |
| 33 | 4-Fluoro-2-(4-iodo-2-methyl-phenylamino)-benzamide | 158 |
| 34 | 4-Fluoro-2-(4-iodo-2-methyl-phenylamino)-N-methyl-benzamide | 102.5–104.5 |
| 35 | N-Ethyl-4-fluoro-2-(4-iodo-2-methyl-phenylamino)-benzamide | 90–91 |
| 36 | 4-Fluoro-2-(4-iodo-2-methyl-phenylamino)-N,N-dimethyl-benzamide | oil |
| 37 | 4-Fluoro-2-(4-iodo-2-methyl-phenylamino)-N-(1H-tetrazol-5-yl)-benzamide | 285–288 DEC |
| 38 | 5-Bromo-2-(4-iodo-2-methyl-phenylamino)-benzamide | 180–182 |
| 39 | 5-Chloro-2-(4-iodo-2-methyl-phenylamino)-N,N dimethyl-benzamide | 137–138 |
| 40 | [5-Chloro-2-(4-iodo-2-methyl-phenylamino)-benzoylamino]-acetic acid | 170–173 |
| 41 | 4-Fluoro-2-(4-iodo-2-methyl-phenylamino)-N-propyl-benzamide | 69–71 |
| 42 | 5-Bromo-N-(2-hydroxy-ethyl)-2-(4-iodo-2-methyl-phenylamino)-benzamide | 132–133.4 |
| 43 | N,N-Diethyl-4-fluoro-2-(4-iodo-2-methyl-phenylamino)-benzamide | oil |
| 44 | 4-Fluoro-N-{3-[4-(2-hydroxy-ethyl)-piperazin-1-yl]-propyl}-2-(4-iodo-2-methyl-phenylamino)-benzamide | 122–124 |
| 45 | N,N-Diethyl-2-(4-iodo-2-methyl-phenylamino)-5-nitro-benzamide | 91–93 |
| 46 | N-Butyl-4-fluoro-2-(4-iodo-2-methyl-phenylamino)-benzamide | 97–99 |
| 47 | 5-Chloro-N,N-diethyl-2-(4-iodo-2-methyl-phenylamino)-benzamide | 118–120 |
| 48 | 5-Bromo-2-(4-iodo-2-methyl-phenylamino)-N,N-dimethyl-benzamide | 142.5–144 |

EXAMPLE 49

4-Flouro-2-(4-iodo-2-methyl-phenylamino)-benzyl Alcohol

4-Fluoro-2-(4-iodo-2-methyl-phenylamino)-benzoic acid (0.50 g, 1.35 mmol) was dissolved in 6 mL (6 mmol) of cold 1.0 M boranetetrahydrofuran complex in tetrahydrofuran solution. The reaction mixture was stirred under nitrogen atmosphere at room temperature overnight. The reaction was quenched with 80 mL of methanol. Concentration in vacuo produced a clear tan oil which was purified by MPLC. Elution with dichloromethane afforded 0.4285 (89%) of a white solid; mp 99–100.5° C.;

$^1$H NMR (400 MHz; DMSO): δ 7.57 (d, 1H, J=1.7 Hz), 7.45 (dd, 1H, J=8.4, 1.9 Hz), 7.39 (s, 1H), 7.29 (t, 1H, J=7.5 Hz), 6.89 (d, 1H, J=8.4 Hz), 6.67–6.60 (m, 1H), 5.47 (t, 1H, J=5.5 Hz), 4.49 (d, 2H, 5.1 Hz), 2.14 (s, 3H); IR (KBr) 3372 (O—H stretch) cm$^{-1}$; MS (CI) M+1=358. Analysis calculated for $C_{14}H_{13}FINO$: C, 47.08; H, 3.67; N, 3.92. Found: C, 47.17; H, 3.75; N, 3.72.

EXAMPLE 50–52

The following benzyl alcohols were prepared by the general procedure of Example 49.

| Example No. | Compound | MP ° C. |
|---|---|---|
| 50 | [5-Chloro-2-(4-iodo-2-methyl-phenylamino)-phenyl]-methanol | 82–85 |
| 51 | [2-(4-Iodo-2-methyl-phenylamino)-5-nitro-phenyl]-methanol | 126.5–128.5 |
| 52 | [5-Bromo-2-(4-iodo-2-methyl-phenylamino)-phenyl]-methanol | 60.5–63.5 |

Several invention compounds of Formula I were prepared utilizing combinatorial synthetic techniques. The general procedure is as follows:

To a 0.8-mL autosampler vial in a metal block was added 40 μL of a 0.5 M solution of the acid in DMF and 40 μL of the reagent amine (2 M solution in Hunig's base and 1 M in amine in DMF). A 0.5 M solution of PyBrop was freshly prepared and 50 μL were added to the autosampler vial. The reaction was allowed to stand for 24 hours.

The reaction mixture was transferred to a 2-dram vial and diluted with 2 mL of ethyl acetate. The organic layer was washed with 3 mL of distilled water and the water layer washed again with 2 mL of ethyl acetate. The combined organic layers were allowed to evaporate to dryness in an open fuime hood.

The residue was taken up in 2 mL of 50% acetonitrile in water and injected on a semi-prep reversed phase column (10 mm×25 cm, 5 μM spherical silica, pore size 115 A derivatized with C-18, the sample was eluted at 4.7 mL/min with a linear amp to 100% acetonitrile over 8.5 minutes. Elution with 100% acetonitrile continued for 8 minutes). Fractions were collected by monitoring at 214 nM. The residue was dissolved in chloroform and transferred to a preweighed vial, evaporated, and weighed again to determine the yield.

EXAMPLES 53–206

The following compounds of Formula I were prepared by combinatorial methology:

| Example No. | Compound | MS M − H |
|---|---|---|
| 53 | 5-Bromo-3,4-difluoro-N-(2-hydroxy-ethyl)-2-(4-iodo-2-methyl-phenylamino)-benzamide | 510 |
| 54 | N-2,3-Dihydroxy-propyl)-3,4-difluoro-2-(4-iodo-2-methyl-phenylamino)-benzamide | 462 |
| 55 | 5-Bromo-3,4-difluoro-2-(4-iodo-2-methyl-phenylamino)-N-(2-piperidin-1-yl-ethyl)-benzamide | 577 |
| 56 | 3,4-Difluoro-N-(2-hydroxy-ethyl)-2-(4-iodo-2-methyl-phenylamino)-benzamide | 432 |
| 57 | N-(2,3-Dihydroxy-propyl)-4-fluoro-2-(4-iodo-2-methyl-phenylamino)-benzamide | 444 |
| 58 | 3,4-Difluoro-N-(3-hydroxy-propyl)-2-(4-iodo-2-methyl-phenylamino)-benzamide | 446 |
| 59 | 5-Bromo-3,4-difluoro-2-(4-iodo-2-methyl-phenylamino)-N-(2-pyrrolidin-1-yl-ethyl)-benzamide | 564 |
| 60 | 5-Bromo-3,4-difluoro-2-(4-iodo-2-methyl-phenylamino)-N-(2-pyridin-4-yl-ethyl)-benzamide | 571 |
| 61 | 4-Fluoro-N-(2-hydroxy-ethyl)-2-(4-iodo-2-methyl-phenylamino)-benzamide | 414 |
| 62 | 5-Bromo-N-(3-dimethylamino-propyl)-3,4-difluoro-2-(4-iodo-2-methyl-phenylamino)-benzamide | 551 |
| 63 | 5-Bromo-3,4-difluoro-2-(4-iodo-2-methyl-phenylamino)-N-(2-morpholin-4-yl-ethyl)-benzamide | 580 |
| 64 | 3,4-Difluoro-2-(4-iodo-2-methyl-phenylamino)-N-(2-morpholin-4-yl-ethyl)-benzamide | 501 |
| 65 | 3,4-Difluoro-2-(4-iodo-2-methyl-phenylamino)-N-(2-pyrrolidin-1-yl-ethyl)-benzamide | 485 |
| 66 | 3,4-Difluoro-2-(4-iodo-2-methyl-phenylamino)-N-(2-pyridin-4-yl-ethyl)-benzamide | 493 |
| 67 | N-(3-Dimethylamino-propyl)-3,4-difluoro-2-(4-iodo-2-methyl-phenylamino)-benzamide | 473 |
| 68 | N-Benzyl-4-fluoro-2-(4-iodo-2-methyl-phenylamino)-benzamide | 460 |
| 69 | 2-(4-Bromo-2-methyl-phenylamino)-3,4-difluoro-N-(2-hydroxy-ethyl)-benzamide | 384 |
| 70 | 4-Fluoro-2-(4-iodo-2-methyl-phenylamino)-N-(2-morpholin-4-yl-ethyl)-benzamide | 483 |
| 71 | 4-Fluoro-2-(4-iodo-2-methyl-phenylamino)-N-(3-piperidin-1-yl-propyl)-benzamide | 495 |
| 72 | 3,4-Difluoro-2-(4-iodo-2-methyl-phenylamino)-N-(3-piperidin-1-yl-propyl)-benzamide | 513 |
| 73 | 4-Fluoro-2-(4-iodo-2-methyl-phenylamino)-N-(2-thiophen-2-yl-ethyl)-benzamide | 480 |
| 74 | 4-Fluoro-2-(4-iodo-2-methyl-phenylamino)-N-(2-pyrrolidin-1-yl-ethyl)-benzamide | 467 |
| 75 | 2-(4-Bromo-2-methyl-phenylamino)-3,4-difluoro-N-2-morpholin-4-yl-ethyl)-benzamide | 453 |
| 76 | 5-Bromo-3,4-difluoro-2-(4-iodo-2-methyl-phenylamino)-N-pyridin-4-ylmethyl-benzamide | 557 |
| 77 | 3,4-Difluoro-2-(4-iodo-2-methyl-phenylamino)-N-pyridin-4-ylmethyl-benzamide | 479 |
| 78 | 2-(4-Bromo-2-methyl-phenylamino)-N-(3-dimethylamino-propyl)-3,4-difluoro-benzamide | 425 |
| 79 | 4-Fluoro-2-(4-iodo-2-methyl-phenylamino)-N-pyridin-4-ylmethyl-benzamide | 461 |
| 80 | 4-Fluoro-2-(4-iodo-2-methyl-phenylamino)-N-(2-pyridin-4-yl-ethyl)-benzamide | 475 |
| 81 | 2-(4-Bromo-2-methyl-phenylamino)-3,4-difluoro-N-(2-pyridin-4-yl-ethyl)-benzamide | 445 |
| 82 | 2-(4-Bromo-2-methyl-phenylamino)-3,4-difluoro-N-(3-hydroxy-propyl)-benzamide | 400 |
| 83 | 2-(4-Bromo-2-methyl-phenylamino)-3,4-difluoro-N-(2-pyrrolidin-1-yl-ethyl)-benzamide | 437 |
| 84 | 4-Fluoro-2-(4-iodo-2-methyl-phenylamino)-N-phenethyl-benzamide | 474 |
| 85 | 2-(4-Bromo-2-methyl-phenylamino)-3,4-difluoro-N-(2-thiophen-2-yl-ethyl)-benzamide | 450 |
| 86 | 2-(4-Bromo-2-methyl-phenylamino)-3,4-difluoro-N-pyridin-4-ylmethyl-benzamide | 431 |
| 87 | 2-(4-Bromo-2-methyl-phenylamino)-3,4-difluoro-N-phenethyl-benzamide | 444 |
| 88 | 2-(4-Bromo-2-methyl-phenylamino)-3,4-difluoro-N-(2-piperidin-1-yl-ethyl)-benzamide | 451 |
| 89 | 5-Chloro-N-{3-[4-(2-hydroxy-ethyl)-piperazin-1-yl]-propyl}-2-(4-iodo-2-methyl-phenylamino)-benzamide | 557* |
| 90 | 5-Fluoro-N-{3-[4-(2-hydroxy-ethyl)-piperazin-1-yl]-propyl}-2-(4-iodo-2-methyl-phenylamino)-benzamide | 541* |

| Example No. | Compound | MS M−H |
|---|---|---|
| 91 | 2-(4-Iodo-2-methyl-phenylamino)-5-nitro-N-pyridin-4-yl methyl-benzamide | 487 |
| 92 | 5-Bromo-N-{3-[4-(2-hydroxy-ethyl)-piperazin-1-yl]-propyl}-2-(4-iodo-2-methyl-phenylamino)-benzamide | 601* |
| 93 | 5-Chloro-N-(2-diethylamino-ethyl)-2-(4-iodo-2-methyl-phenylamino)-benzamide | 486* |
| 94 | 5-Chloro-2-(4-iodo-2-methyl-phenylamino)-N-(2-piperidin-1-yl-ethyl)-benzamide | 497* |
| 95 | (3-Hydroxy-pyrrolidin-1-yl)-[2-(4-iodo-2-methyl-phenylamino)-5-nitro-phenyl]-methanone | 466 |
| 96 | 5-Chloro-2-(4-iodo-2-methyl-phenylamino)-N-(2-pyrrolidin-1-yl-ethyl)-benzamide | 484* |
| 97 | 5-Bromo-N-(2-diethylamino-ethyl)-2-(4-iodo-2-methyl-phenylamino)-benzamide | 530* |
| 98 | N-{2-[Bis-(2-hydroxy-ethyl)-amino]-ethyl}-5-chloro-2-(4-iodo-2-methyl-phenylamino)-benzamide | 518* |
| 99 | N-{2-[Bis-(2-hydroxy-ethyl)-amino]-ethyl}-5-bromo-2-(4-iodo-2-methyl-phenylamino)-benzamide | 562* |
| 100 | [5-Bromo-2-(4-iodo-2-methyl-phenylamino)-phenyl]-(3-hydroxy-pyrrolidin-1-yl)-methanone | 499 |
| 101 | 2-4-(Iodo-2-methyl-phenylamino)-5-nitro-benzoic acid phenethyl ester | 501 |
| 102 | N-{3-[4-(2-Hydroxy-ethyl)-piperazin-1-yl]-propyl}-2-(4-iodo-2-methyl-phenylamino)-benzamide | 568* |
| 103 | [5-Chloro-2-(4-iodo-2-methyl-phenylamino)-phenyl]-(3-hydroxy-pyrrolidin-1-yl)-methanone | 455 |
| 104 | 5-Fluoro-2-(4-iodo-2-methyl-phenylamino)-N-pyridin-4-ylmethyl-benzamide | 460 |
| 105 | 5-Bromo-2-(4-iodo-2-methyl-phenylamino)-N-(2-pyrrolidin-1-yl-ethyl)-benzamide | 528* |
| 106 | 5-Bromo-2-(4-iodo-2-methyl-phenylamino)-N-(2-piperidin-1-yl-ethyl)-benzamide | 542* |
| 107 | 5-Fluoro-2-(4-iodo-2-methyl-phenylamino)-N-(2-pyrrolidin-1-yl-ethyl)-benzamide | 468* |
| 108 | 5-Chloro-N-(3-dimethylamino-propyl)-2-(4-iodo-2-methyl-phenylamino)-benzamide | 472* |
| 109 | N-{2-[Bis-(52-hydroxy-ethyl)-amino]-ethyl}-5-fluoro-2-(4-iodo-2-methyl-phenylamino)-benzamide | 502* |
| 110 | 5-Chloro-N-(3-hydroxy-propyl)-2-(4-iodo-2-methyl-phenylamino)-benzamide | 445* |
| 111 | 5-Chloro-N-(3-diethylamino-2-hydroxy-propyl)-2-(4-iodo-2-methyl-phenylamino)-benzamide | 516* |
| 112 | 5-Fluoro-2-(4-iodo-2-methyl-phenylamino)-N-(2-piperidin-1-yl-ethyl)-benzamide | 482* |
| 113 | 5-Bromo-N-(3-hydroxy-propyl)-2-(4-iodo-2-methyl-phenylamino)-benzamide | 489* |
| 114 | 5-Bromo-2-(4-iodo-2-methyl-phenylamino)-N-(3-piperidin-1-yl-propyl)-benzamide | 556* |
| 115 | N-{2-[Bis-(2-hydroxy-ethyl)-amino]-ethyl}-2-(4-iodo-2-methyl-phenylamino)-5-nitro-benzamide | 529* |
| 116 | 5-Chloro-2-(4-iodo-2-methyl-phenylamino)-N-(2-morpholin-4-yl-ethyl)-benzamide | 500* |
| 117 | 5-Chloro-N-(3-diethylamino-propyl)-2-(4-iodo-2-methyl-phenylamino)-benzamide | 500* |
| 118 | 5-Chloro-N-(2-diisopropylamino-ethyl)-2-(4-iodo-2-methyl-phenylamino)-benzamide | 514* |
| 119 | 5-Chloro-2-(4-iodo-2-methyl-phenylamino)-N-(3-piperidin-1-yl-propyl)-benzamide | 512* |
| 120 | 2-(4-Iodo-2-methyl-phenylamino)-5-nitro-N-(2-piperidin-1-yl-ethyl)-benzamide | 509* |
| 121 | 5-Bromo-2-(4-iodo-2-methyl-phenylamino)-N-(2-piperazin-1-yl-ethyl)-benzamide | 544* |
| 122 | N-(2-diethylamino-ethyl)-5-fluoro-2-(4-iodo-2-methyl-phenylamino)-benzamide | 470* |
| 123 | 5-Bromo-N-(3-dimethylamino-propyl)-2-(4-iodo-2-methyl-phenylamino)-benzamide | 516* |
| 124 | N-(3-Hydroxy-propyl)-2-(4-iodo-2-methyl-phenylamino)-5-nitro-benzamide | 456* |
| 125 | 5-Fluoro-N-(3-hydroxy-propyl)-2-(4-iodo-2-methyl-phenylamino)-benzamide | 429* |
| 126 | N-(3-Diethylamino-propyl)-5-fluoro-2-(4-iodo-2-methyl-phenylamino)-benzamide | 484* |
| 127 | N-(3-Diethylamino-propyl)-2-(4-iodo-2-methyl-phenylamino)-5-nitro-benzamide | 511* |
| 128 | 5-Bromo-2-(4-iodo-2-methyl-phenylamino)-N-(2-morpholin-4-yl-ethyl)-benzamide | 544* |
| 129 | 2-(4-Iodo-2-methyl-phenylamino)-5-nitro-N-(3-piperdin-1-yl-propyl)-benzamide | 523* |
| 130 | [5-Fluoro-2-(4-iodo-2-methyl-phenylamino)-phenyl]-(3-hydroxy-pyrrolidin-1-yl)-methanone | 439 |
| 131 | 5-Bromo-N-(2-diisopropylamino-ethyl)-2-(4-iodo-2-methyl-phenylamino)-benzamide | 558* |
| 132 | 5-Fluoro-2-(4-iodo-2-methyl-phenylamino)-N-(2-morpholin-4-yl-ethyl)-benzamide | 484* |
| 133 | 5-Fluoro-2-(4-iodo-2-methyl-phenylamino)-N-(3-piperidin-1-yl-propyl)-benzamide | 496* |
| 134 | [5-Fluoro-2-(4-iodo-2-methyl-phenylamino)-phenyl]-[4-(2-hydroxy-ethyl)-piperazin-1-yl]-methanone | 482 |
| 135 | N-(3-Diethylamino-2-hydroxy-propyl)-5-fluoro-2-(4-iodo-2-methyl-phenylamino)-benzamide | 500* |
| 136 | [5-Chloro-2-(4-iodo-2-methyl-phenylamino)-benzoylamino]-acetic acid | 443 |
| 137 | 2-(4-Iodo-2-methyl-phenylamino)-5-nitro-N-(2-pyrrolidin-1-yl-ethyl)-benzamide | 495* |
| 138 | N-(3-Diethylamino-propyl)-2-(4-iodo-2-methyl-phenylamino)-5-nitro-benzamide | 483* |
| 139 | N-(2-Diisopropylamino-ethyl)-5-fluoro-2-(4-iodo-2-methyl-phenylamino)-benzamide | 498* |
| 140 | 5-Fluoro-2-(4-iodo-2-methyl-phenylamino)-thiobenzoic acid S-phenethyl ester | 490 |
| 141 | 5-Chloro-2-(4-iodo-2-methyl-phenylamino)-thiobenzoic acid S-phenethyl ester | 506 |
| 142 | 5-Bromo-2-(4-iodo-2-methyl-phenylamino)-thiobenzoic acid S-benzyl ester | 536 |
| 143 | 2-(4-Iodo-2-methyl-phenylamino)-5-nitro-thiobenzoic acid S-benzyl ester | 503 |
| 144 | 5-Fluoro-2-(4-iodo-2-methyl-phenylamino)-thiobenzoic acid S-benzyl ester | 476 |
| 145 | 5-Chloro-2-(4-iodo-2-methyl-phenylamino)-thiobenzoic acid S-benzyl ester | 492 |
| 146 | N-Cyclopropyl-5-fluoro-2-(4-iodo-2-methyl-phenylamino)-benzamide | 409 |
| 147 | 5-Chloro-N-(2-hydroxy-ethyl)-2-(4-iodo-2-methyl-phenylamino)-benzamide | 429 |
| 148 | 5-Fluoro-N-(2-hydroxy-ethyl)-2-(4-iodo-2-methyl-phenylamino)-benzamide | 413 |
| 149 | N-Benzyloxy-5-fluoro-2-(4-iodo-2-methyl-phenylamino)-benzamide | 475 |
| 150 | N-Benzyloxy-5-bromo-2-(4-iodo-2-methyl-phenylamino)-benzamide | 593* |
| 151 | 2-(4-Iodo-2-methyl-phenylamino)-5-nitro-N-(4-sulfamoyl-benzyl)-benzamide | 567 |
| 152 | 5-Bromo-N-(2-hydroxy-ethyl)-2-(4-iodo-2-methyl-phenylamino)-benzamide | 473 |
| 153 | N-(2-Hydroxy-ethyl)-5-iodo-2-(4-iodo-2-methyl-phenylamino)-benzamide | 521 |
| 154 | N-(2-Hydroxy-ethyl)-2-(4-iodo-2-methyl-phenylamino)-5-nitro-benzamide | 440 |
| 155 | 2-(4-Iodo-2-methyl-phenylamino)-N-methyl-5-nitro-N-phenyl-benzamide | 486 |
| 156 | 5-Chloro-N-cyclopropyl-2-(4-iodo-2-methyl-phenylamino)-benzamide | 425 |
| 157 | 5-Fluoro-2-(4-iodo-2-methyl-phenylamino)-N-methyl-N-phenyl-benzamide | 459 |
| 158 | N-Allyl-5-fluoro-2-(4-iodo-2-methyl-phenylamino)-benzamide | 409 |
| 159 | N-Benzyloxy-5-iodo-2-(4-iodo-2-methyl-phenylamino)-benzamide | 583 |
| 160 | 5-Fluoro-2-(4-iodo-2-methyl-phenylamino)-N-(4-sulfamoyl-benzyl)-benzamide | 538 |
| 161 | N-Allyl-5-chloro-2-(4-iodo-2-methyl-phenylamino)-benzamide | 425 |
| 162 | N-Cyclopropyl-2-(4-iodo-2-methyl-phenylamino)-5-nitro-benzamide | 436 |
| 163 | 5-Bromo-N-cyclopropyl-2-(4-iodo-2-methyl-phenylamino)-benzamide | 469 |
| 164 | 5-Chloro-2-(4-iodo-2-methyl-phenylamino)-N-methyl-N-phenyl-benzamide | 475 |

-continued

| Example No. | Compound | MS M − H |
|---|---|---|
| 165 | 5-Iodo-2-(4-iodo-2-methyl-phenylamino)-N-(4-sulfamoyl-benzyl)-benzamide | 646 |
| 166 | 5-Bromo-2-(4-iodo-2-methyl-phenylamino)-N-(4-sulfamoyl-benzyl)-benzamide | 598 |
| 167 | N-Allyl-2-(4-iodo-2-methyl-phenylamino)-5-nitro-benzamide | 436 |
| 168 | 2-(4-Iodo-2-methyl-phenylamino)-5-nitro-N-(4-sulfamoyl-benzyl)-benzamide | 565 |
| 169 | N-Allyl-5-bromo-2-(4-iodo-2-methyl-phenylamino)-benzamide | 469 |
| 170 | 5-Fluoro-2-(4-iodo-2-methyl-phenylamino)-N-(3-methyl-benzyl)-benzamide | 473 |
| 171 | N-Cyclopropyl-5-iodo-2-(4-iodo-2-methyl-phenylamino)-benzamide | 517 |
| 172 | 5-Bromo-2-(4-iodo-2-methyl-phenylamino)-N-methyl-N-phenyl-benzamide | 519 |
| 173 | N-Benzyloxy-2-(4-iodo-2-methyl-phenylamino)-5-nitro-benzamide | 502 |
| 174 | N-Cyclohexyl-5-iodo-2-(4-iodo-2-methyl-phenylamino)-benzamide | 559 |
| 175 | N-Allyl-5-iodo-2-(4-iodo-2-methyl-phenylamino)-benzamide | 517 |
| 176 | 5-Iodo-2-(4-iodo-2-methyl-phenylamino)-N-(3-methyl-benzyl)-benzamide | 581 |
| 177 | 2-(4-Iodo-2-methyl-phenylamino)-N-(3-methyl-benzyl)-5-nitro-benzamide | 500 |
| 178 | 5-Iodo-2-(4-iodo-2-methyl-phenylamino)-N-methyl-N-phenyl-benzamide | 567 |
| 179 | N-Cyclohexyl-5-fluoro-2-(4-iodo-2-methyl-phenylamino)-benzamide | 451 |
| 180 | 5-Chloro-N-cyclohexyl-2-(4-iodo-2-methyl-phenylamino)-benzamide | 467 |
| 181 | 5-Bromo-2-(4-iodo-2-methyl-phenylamino)-N-(3-methyl-benzyl)-benzamide | 533 |
| 182 | 5-Bromo-N-cyclohexyl-2-(4-iodo-2-methyl-phenylamino)-benzamide | 511 |
| 183 | 5-Chloro-2-(4-iodo-2-methyl-phenylamino)-N-(3-methyl-benzyl)-benzamide | 489 |
| 184 | N-Cyclohexyl-2-(4-iodo-2-methyl-phenylamino)-5-nitro-benzamide | 478 |
| 185 | N-Benzyloxy-5-bromo-2-(4-iodo-2-methyl-phenylamino)-benzamine | 538 |
| 186 | N-Benzyloxy-5-fluoro-2-(4-iodo-2-methyl-phenylamino)-benzamide | 477 |
| 187 | 5-Chloro-N-(2-hydroxy-ethyl)-2-(4-iodo-2-methyl-phenylamino)-benzamide | 431 |
| 188 | 5-Bromo-N-(2-hydroxy-ethyl-2-(4-iodo-2-methyl-phenylamino)-benzamide | 475 |
| 189 | 2-(4-Iodo-2-methyl-phenylamino)-N-methyl-5-nitro-N-phenyl-benzamide | 488 |
| 190 | 5-Chloro-2-(4-iodo-2-methyl-phenylamino)-N-methyl-N-phenyl-benzamide | 477 |
| 191 | N-(2-Hydroxy-ethyl)-5-iodo-2-(4-iodo-2-methyl-phenylamino)-benzamide | 523 |
| 192 | 5-Chloro-N-cyclopropyl-2-(4-iodo-2-methyl-phenylamino)-benzamide | 425 |
| 193 | N-Allyl-5-chloro-2-(4-iodo-2-methyl-phenylamino)-benzamide | 427 |
| 194 | 5-Fluoro-2-(4-iodo-2-methyl-phenylamino)-N-methyl-N-phenyl-benzamide | 461 |
| 195 | N-(2-Hydroxy-ethyl)-2-(4-iodo-2-methyl-phenylamino)-5-nitro-benzamide | 442 |
| 196 | 5-Fluoro-N-(2-hydroxy-ethyl)-2-(4-iodo-2-methyl-phenylamino)-benzamide | 415 |
| 197 | 5-Bromo-N-cyclopropyl-2-(4-iodo-2-methyl-phenylamino)-benzamide | 472 |
| 198 | N-Cyclopropyl-5-fluoro-2-(4-iodo-2-methyl-phenylamino)-benzamide | 411 |
| 199 | 5-Fluoro-2-(4-iodo-2-methyl-phenylamino)-N-(4-sulfamoyl-benzyl)-benzamide | 540 |
| 200 | N-Cyclopropyl-2-(4-iodo-2-methyl-phenylamino)-5-nitro-benzamide | 438 |
| 201 | N-Allyl-5-fluoro-2-(4-iodo-2-methyl-phenylamino)-benzamide | 411 |
| 202 | N-Benzyloxy-5-iodo-2-(4-iodo-2-methyl-phenylamino)-benzamide | 585 |
| 203 | N-Allyl-5-bromo-2-(4-iodo-2-methyl-phenylamino)-benzamide | 472 |
| 204 | 5-Bromo-2-(4-iodo-2-methyl-phenylamino)-N-(4-sulfamoyl-benzyl)-benzamide | 601 |
| 205 | 5-Bromo-2-(4-iodo-2-methyl-phenylamino)-N-methyl-N-phenyl-benzamide | 522 |
| 206 | N-Allyl-2-(4-iodo-2-methyl-phenylamino)-5-nitro-benzamide | 438 |

*M + H

EXAMPLE 207

Preparation of [4-Chloro-2-(1H-tetrazol-5-yl)-(4-iodo-2-methyl-phenyl)-amine

Step a: Preparation of 5-chloro-2-fluoro-benzaldehyde

To a solution of 1-chloro-4-fluorobenzne (13.06 g, 0.1 mol) in THF (180 mL), at −78° C., LDA (2M solution in THF, 50 mL, 0.1 mol) was added drop wise. After stirring at −78° C. for 1.5 hours, DMF (8 mL) was added to the reaction mixture and allowed to warm up to room temperature overnight. The reaction mixture was partitioned between water and $Et_2O$. The $Et_2O$ layer was dried ($MgSO_4$) and the solvent removed in vacuum to give 14.95 g (94%) yield of crude aldehyde: $^1H$ NMR ($CDCl_3$): δ, 10.3 (s, —C(=O)H).

Step b: Preparation of 5-chloro-2-fluoro-benzaldehyde Oxime

A solution of 5-chloro-2-fluoro-benzaldehyde (10 g, 0.0631 mol), hydroxylamine hydrochloride (6.57 g, 0.0946 mol) and pyridine (8.3 mL, 0.1010 mol) in EtOH (100 mL) was heated at 75° C. (oil bath temperature) for 1 hour and the solvent removed under vacuum to give an oil. The oil was partitioned between water and $CH_2Cl_2$. The $CH_2Cl_2$ layer was dried ($MgSO_4$) and the solvent removed under vacuum to give crude aldoxime as a solid. The solid was purified by medium pressure liquid chromatography on silica. Elution with $CH_2Cl_2$ gave 4.87 g (28%) of the aldoxime as white solid: mp 95–97° C.;

Analysis calculated for $C_7H_5NOFCl$: C, 48.44; H, 2.90; N, 8.07. Found: C, 48.55; H, 2.69, N, 7.90.

Step c: Preparation of 5-chloro-2-fluoro-benzonirile

A solution of the 5-chloro-2-fluoro-benzaldehyde oxime (3.15 g, 0.0182 mol) in acetic anhydride (150 mL) was refluxed for 16 hours. The reaction mixture was cooled to room temperature and poured into saturated aqueous $NaHCO_3$ (200 mL) solution. The mixture was extracted with $Et_2O$. The $Et_2O$ layer was dried ($K_2CO_3$) and the solvent removed to give the product as an oily solid. The product was used without further purification in the next step.

Step d: Preparation of 5-(5-chloro-2-fluoro-phenyl)-1H-tetrazole

A mixture of 5-chloro-2-fluoro-benzonitrile (2.84 g, 0.01823 mol), butanol (15 mL), sodium azide (1.543 g, 0.0237 mol), acetic acid (1.36 niL, 0.0237 mol) was refluxed for 24 hours. The reaction mixture was cooled to room temperature, additional 1.543 g sodium azide added, and the reaction mixture refluxed for additional 24 hours. After cooling to room temperature, $Et_2O$ (100 mL) and 10% aqueous NaOH (200 mL) were added sequentially. The mixture was vigorously stirred. The aqueous layer was separated, cooled with ice-methanol bath (−15° C.) and acidified to pH 1 with conc. HCl. A gray solid precipitated. The solid was dried in vacuum at 50° C. to give 1.76 g (49%) of 5-(5-chloro-2-fluoro-phenyl)-1H-tetrazole: mp partial melt at 110° C., complete melting at 124° C.);

$^1$H (400 Mz, CDCl$_3$): δ 8.19–8.08 (m, 1H), 7.77–7.71 (m, 1H), 7.61–7.52 (m, 1H); $^{13}$C (100 Mz, CDCl$_3$): δ 159.00, 156.49, 140.88, 133.02, 132.93, 130.73, 129.23, 129.21, 129.08, 126.05, 118.96,118.73, 114.50; MS (CI) M+1=199 (100), M=198 (6).

Step e: Preparation of [4-Chloro-2-(1H-tetrazol-5-yl)-(4-iodo-2-methyl-phenyl)-amine To a solution of 2-methyl-4-iodoaniline (3.52 g, 0.0151 mol) in THF (25 mL) at −78° C., LDA (2 molar solution in THF, 11.33 mL, 0.02267 mol) was added dropwise. After stirring for 0.5 hours, a solution of 1-(tetrazol-5-yl)-2-fluoro-5-chlorobenzene (1.5 g, 0.00756 mol) in THF (15 mL) was added dropwise. The reaction was stirred for 16 hours as it warmed up to room temperature. The reaction mixture was quenched with aqueous conc. NH$_4$Cl solution and extracted with CH$_2$Cl$_2$. The organic layer was dried (MgSO$_4$) and the solvent removed giving a crude product as an oil. The oil with CH$_2$Cl$_2$→CH$_2$Cl$_2$:MeOH (9.7:0.3) gave 1.5 g (48%) of the desired product:

mp 205–208° C.; $^1$H (400 Mz, DMSO): δ 9.13 (s, 1H), 8.00–7.99 (s, 1H), 7.69 (s, 1H), 7.55–7.52 (m, 1H), 7.43–7.40 (m, 1H), 7.12–7.05 (m, 1H), 2.24 (s, 3H); $^{13}$C (100 Mz, CDCl$_3$): δ 141.87, 139.28, 138.88, 135.47, 133.71, 131.65, 128.15, 123.69, 121.94, 116.68, 87.79, 17.22; MS (CI) M+2=413 (44), M+1=412 (85), M=411 (100). Analysis calculated for C$_{14}$H$_{11}$N$_5$ClI.0.5H$_2$O: C, 39.97; H, 2.87; N, 16.65. Found: C, 38.87, H, 2.77; N, 16.47.

The following tetrazole substituted phenylamines were prepared by following the general procedure of Example 207.

EXAMPLE 208

(4-iodo-2-methyl-phenyl)-[2-(1H-tetrazol-5-yl)-phenyl]amine mp 231 ° C. (dec)

EXAMPLE 209

[4-nitro-2-(1H-tetrazol-5-yl)-(4-iodo-2-methyl-phenyl)-amine mp 205–208° C.

The 4-bromo and 4-iodo phenylamino benzhydroxamic acid derivatives of Formula II can be prepared from commercially available starting materials utilizing synthetic methodologies well-known to those skilled in organic chemistry. A typical synthesis is carried out by reacting a 4-bromo or 4-iodo aniline with a benzoic acid having a leaving group at the 2-position to give a phenylamino benzoic acid, and then reacting the benzoic acid phenylamino derivative with a hydroxylamine derivative (Scheme 3), where L is a leaving group, for example halo such as fluoro, chloro, bromo or iodo, or an activated hydroxy group such as a diethylphosphate, trimethylsilyloxy, p-nitrophenoxy, or phenylsulfonoxy.

The reaction of aniline and the benzoic acid derivative generally is accomplished by mixing the benzoic acid with an equimolar quantity or excess of the aniline in an unreactive organic solvent such as tetrahydrofuran, or toluene, in the presence of a base such as lithium diisopropylamide, n-butyl lithium, sodium hydride, and sodium amide. The reaction generally is carried out at a temperature of about −78° C. to about 25° C., and normally is complete within about 2 hours to about 4 days. The product can be isolated by removing the solvent, for example by evaporation under reduced pressure, and further purified, if desired, by standard methods such as chromatography, crystallization, or distillation.

Scheme 3

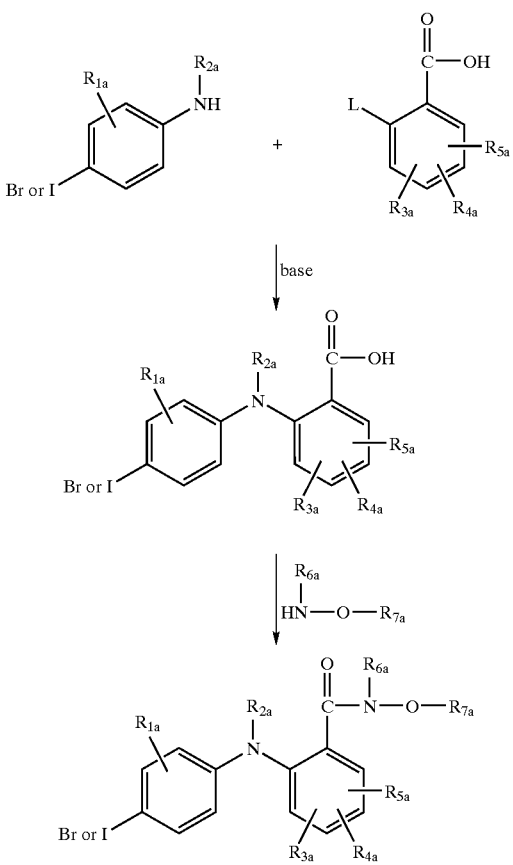

The phenylamino benzoic acid next is reacted with a hydroxylamine derivative HNR$_{6a}$OR$_{7a}$ in the presence of a peptide coupling reagent. Hydroxylamine derivatives that can be employed include methoxylamine, N-ethyl-isopropoxy amine, and tetrahydro-oxazine. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)-phosphonium hexafluorophosphate (PyBrOP) and (benzotriazolyloxy)tripyrrolidino phosphonium hexafluorophosphate (PyBOP). The phenylamino benzoic acid and hydroxylamino derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can.be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol. An alternative method for making the invention compounds involves first converting a benzoic acid to a hydroxamic acid derivative, and then reacting the hydroxamic acid derivative with an aniline. This synthetic sequence is depicted in Scheme 4, where L is a leaving group. The general reaction conditions for both of the steps in Scheme 4 are the same as those described above for Scheme 3.

Scheme 4

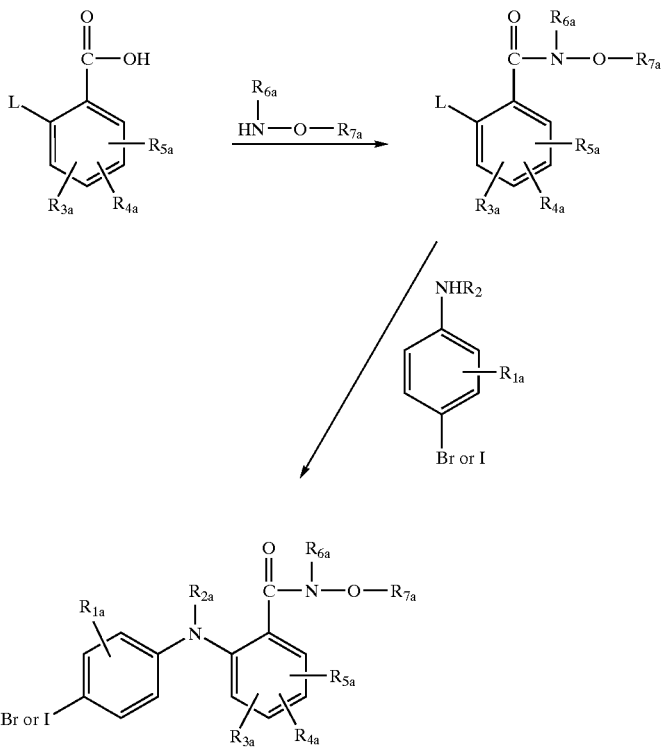

Yet another method for making invention compounds comprises reacting a phenylamino benzhydroxamic acid with an ester forming group as depicted in Scheme 5, where L is a leaving group such as halo, and a base is triethylamine or diisopropylamine.

Scheme 5

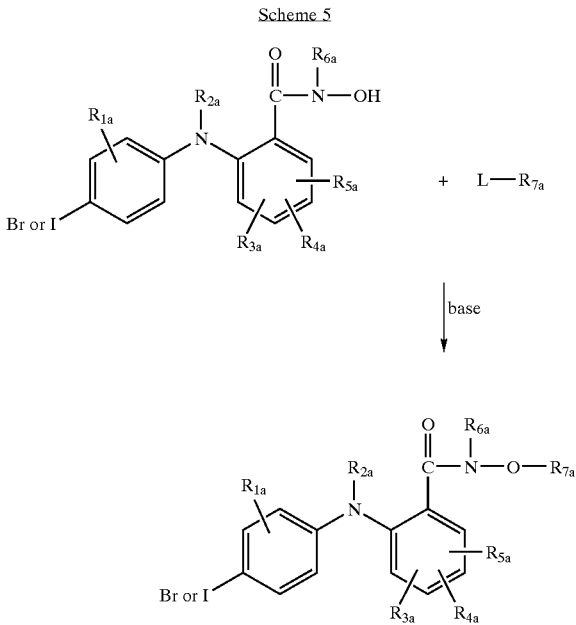

The synthesis of compounds of Formula (II) is further illustrated by the following detailed examples.

EXAMPLE 1a

4-Fluoro-N-hydroxy-2-(4-iodo-2-methyl-phenylamino)-benzamide (a) Preparation of 4-Fluoro-2-(4-iodo-2-methyl-phenylamino)-benzoic Acid To a stirred solution containing 3.16 g (0.0133 mol) of 2-amino-5-iodotoluene in 5 mL of tetrahydrofuran at −78° C. was added 10 mL (0.020 mol) of a 2.0 M lithium diisopropylamide in tetrahydrofuran/heptane/ethylbenzene (Aldrich) solution. The resulting green suspension was stirred vigorously for 15 minutes, after which time a solution of 1.00 g (0.00632 mol) of 2,4-difluorobenzoic acid in 10 mL of tetrahydrofuran was added. The reaction temperature was allowed to increase slowly to room temperature, at which temperature the mixture was stirred for 2 days. The reaction mixture was concentrated by evaporation of the solvent under reduced pressure. Aqueous HCl (10%) was added to the concentrate, and the solution was extracted with dichloromethane. The organic phase was dried ($MgSO_4$) and then concentrated over a steambath to low volume (10 mL) and cooled to room temperature. The off-white fibers which formed were collected by vacuum filtration, rinsed with hexane, and dried in a vacuum-oven (76° C.; ca. 10 mm of Hg) to afford 1.10 g (47%) of the desired material; mp 224–229.5° C.;

$^1$H NMR (400 MHz, DMSO): δ 9.72 (s, 1H), 7.97 (dd, 1H, J=7.0, 8.7 Hz), 7.70 (d, 1H, J=1.5 Hz), 7.57 (dd, 1H, J=8.4, 1.9 Hz), 7.17 (d, 1H, J=8.2 Hz), 6.61–6.53 (m, 2H), 2.18 (s, 3H); $^{13}$C NMR (100 MHz, DMSO): δ 169.87, 166.36 (d, $J_{C-F}$=249.4 Hz), 150.11 (d, $J_{C-F}$=11.4 Hz), 139.83, 138.49, 136.07, 135.26 (d, $J_{C-F}$=1.5 Hz), 135.07, 125.60, 109.32, 104.98 (d, $J_{C-F}$=21.1 Hz), 99.54 (d, $J_{C-F}$=26.0 Hz), 89.43, 17.52; $^{19}$F NMR (376 MHz, DMSO): δ −104.00 to −104.07 (m); IR (KBr) 1670 (C=O stretch)

cm$^{-1}$; MS (CI) M+1 372. Analysis calculated for C$_{14}$H$_{11}$FINO$_2$: C, 45.31; H, 2.99; N, 3.77. Found: C, 45.21; H, 2.77; N, 3.64.

(b) Preparation of 4-Fluoro-N-hydroxy-2-(4-iodo-2-methyl-phenylamino)-benzamide

To a stirred solution of 4-fluoro-2-(4-iodo-2-methyl-phenylamino)-benzoic acid (0.6495 g, 0.001750 mol), O-(tetrahydro-2H-pyran-2-yl)-hydroxylamine (0.2590 g, 0.002211 mol), and diisopropylethylamine (0.40 mL, 0.0023 mol) in 31 mL of an equivolume tetrahydrofuran-dichloromethane solution was added 1.18 g (0.00227 mol) of solid PyBOP ([benzotriazolyloxy]tripyrrolidino phosphonium hexafluorophosphate, Advanced ChemTech) directly. The reaction mixture was stirred for 30 minutes after which time it was concentrated in vacuo. The brown oil was treated with 10% aqueous hydrochloric acid. The suspension was extracted with ether. The organic extraction was washed with 10% sodium hydroxide followed by another 10% hydrochloric acid wash, was dried (MgSO$_4$) and concentrated in vacuo to afford 1.0 g of a light-brown foam. This intermediate was dissolved in 25 mL of ethanolic hydrogen chloride, and the solution was allowed to stand at room temperature for 15 minutes. The reaction mixture was concentrated in vacuo to a brown oil that was purified by flash silica chromatography. Elution with a gradient (100 % dichloromethane to 0.6 % methanol in dichloromethane) afforded 0.2284 g of a light-brown viscous oil. Scratching with pentane-hexanes and drying under high vacuum afforded 0.1541 g (23%) of an off-white foam; mp 61–75° C.;

$^1$H NMR (400 MHz, DMSO): δ 11.34 (s, 1H), 9.68 (s, 1H), 9.18 (s, 1H), 7.65 (d, 1H, J=1.5 Hz), 7.58 (dd, 1H, J=8.7, 6.8 Hz), 7.52 (dd, 1H, J=8.4, 1.9 Hz), 7.15 (d, 1H, J=8.4 Hz), 6.74 (dd, 1H, J=11.8, 2.4 Hz), 6.62 (ddd, 1H, J=8.4, 8.4, 2.7 Hz), 2.18 (s, 3H); $^{13}$C NMR (100 MHz, DMSO): δ 165.91, 164.36 (d, J$_{C-F}$=247.1 Hz), 146.78, 139.18, 138.77, 135.43, 132.64, 130.60 (d, J$_{C-F}$=11.5 Hz), 122.23, 112.52, 104.72 (d, J=22.1 Hz), 100.45 (d, J$_{C-F}$=25.2 Hz), 86.77, 17.03; $^{19}$F NMR (376 MHz, DMSO): δ −107.20 to −107.27 (m); IR (KBr) 3307 (broad, O—H stretch), 1636 (C=O stretch) cm$^{-1}$; MS (CI) M+1 387. Analysis calculated for C$_{14}$H$_{12}$FIN$_{2O2}$: C, 43.54; H, 3.13; N, 7.25. Found: C, 43.62; H, 3.24; N, 6.98.

EXAMPLE 2a

5-Bromo-3,4-difluoro-N-hydroxy-2-(4-iodo-2-methyl-phenylamino)-benzamide (a) Preparation of 5-Bromo-2,3,4-trifluorobenzoic Acid To a stirred solution comprised of 1-bromo-2,3,4-trifluorobenzene (Aldrich, 99%; 5.30 g, 0.0249 mol) in 95 mL of anhydrous tetrahydrofuran cooled to −78° C. was slowly added 12.5 mL of 2.0 M lithium diisopropylamide in heptane/tetrahydrofuran/ethylbenzene solution (Aldrich). The mixture was stirred for 1 hour and transferred by canula into 700 mL of a stirred saturated ethereal carbon dioxide solution cooled to −78° C. The cold bath was removed, and the reaction mixture was stirred for 18 hours at ambient temperature. Dilute (10%) aqueous hydrochloric acid (ca. 500 mL) was poured into the reaction mixture, and the mixture was subsequently concentrated on a rotary evaporator to a crude solid. The solid product was partitioned between diethyl ether (150 mL) and aq. HCl (330 mL, pH 0). The aqueous phase was extracted with a second portion (100 mL) of diethyl ether, and the combined ethereal extracts were washed with 5% aqueous sodium hydroxide (200 mL) and water (100 mL, pH 12). These combined alkaline aqueous extractions were acidified to pH 0 with concentrated aqueous hydrochloric acid. The resulting suspension was extracted with ether (2×200 mL). The combined organic extracts were dried (MgSO$_4$), concentrated in vacuo, and subjected to high vacuum until constant mass was achieved to afford 5.60 g (88% yield) of an off-white powder; mp 139–142.5° C.;

$^1$H NMR (400 MHz, DMSO): δ 13.97 (broad s, 1H), 8.00–7.96 (m, 1H); $^{13}$C NMR (100 MHz, DMSO): δ 162.96, 129.34, 118.47, 104.54 (d, J$_{C-F}$=22.9 Hz); $^{19}$F NMR (376 MHz, DMSO): δ −120.20 to −120.31 (m), −131.75 to −131.86 (m), −154.95 to −155.07 (m); IR (KBr) 1696 (C=O stretch)cm$^{-1}$; MS (CI) M+1=255. Analysis calculated for C$_{74}$H$_{21}$BrF$_3$O$_2$: C, 32.97; H, 0.79; N, 0.00; Br, 31.34; F, 22.35. Found: C, 33.18; H, 0.64; N, 0.01; Br, 30.14; F, 22.75.

(b) Preparation of 5-Bromo-3,4-difluoro-2-(4-iodo-2-methyl-phenylamino)-benzoic Acid To a stirred solution comprised of 1.88 g (0.00791 mol) of 2-amino-5-iodotoluene in 10 mL of tetrahydrofuran at −78° C. was added 6 MnL (0.012 mol) of a 2.0 M lithium diisopropylamide in tetrahydrofuran/heptane/ethylbenzene (Aldrich) solution. The resulting green suspension was stirred vigorously for 10 minutes, after which time a solution of 1.00 g (0.00392 mol) of 5-bromo-2,3,4-trifluorobenzoic acid in 15 mL of tetrahydrofuran was added. The cold bath was subsequently removed, and the reaction mixture stirred for 18 hours. The mixture was concentrated, and the concentrate was treated with 100 mL of dilute (10%) aqueous hydrochloric acid. The resulting suspension was extracted with ether (2×150 mL), and the combined organic extractions were dried (MgSO$_4$) and concentrated in vacuo to give an orange solid. The solid was triturated with boiling dichloromethane, cooled to ambient temperature, and collected by filtration. The solid was rinsed with dichloromethane, and dried in the vacuum-oven (80° C.) to afford 1.39 g (76%) of a yellow-green powder; mp 259.5–262° C.;

$^1$H NMR (400 MHz, DMSO): δ 9.03 (s, 1H), 7.99 (dd, 1H, J=7.5, 1.9 Hz), 7.57 (dd, 1H, J=1.5 Hz), 7.42 (dd, 1H, J=8.4, 1.9 Hz), 6.70 (dd, 1H, J=8.4, 6.0 Hz), 2.24 (s, 3H); $^{19}$F NMR (376 MHz, DMSO): δ −123.40 to −123.47 (m); −139.00 to −139.14 (m); IR (KBr) 1667 (C=O stretch)cm$^-$1; MS (CI) M+1=469. Analysis calculated for C$_{14}$H$_9$BrF$_2$INO$_2$: C, 35.93; H, 1.94; N, 2.99; Br, 17.07; F, 8.12; I, 27.11. Found: C, 36.15; H, 1.91; N, 2.70; Br, 16.40; F, 8.46; I, 26.05.

(c) Preparation of 5-Bromo-3,4-difluoro-N-hydroxy-2-(4-iodo-2-methyl-phenylamino)-benzamide To a stirred solution comprised of 5-bromo-3,4-difluoro-2-(4-iodo-2-methyl-phenylamino)-benzoic acid (0.51 g, 0.0011 mol), O-(tetrahydro-2H-pyran-2-yl)-hydroxylamine (0.15 g, 0.0013 mol), and diisopropylethylamine (0.25 mL, 0.0014 mol) in 20 mL of an equivolume tetrahydrofuran-dichloromethane solution was added 0.6794 g (0.001306 mol) of solid PyBOP (Advanced ChemTech) directly. The reaction mixture was stirred at 24° C. for 10 minutes, and then was concentrated to dryness in vacuo. The concentrate was suspended in 100 mL of 10% aqueous hydrochloric acid. The suspension was extracted with 125 mL of diethyl ether. The ether layer was separated, washed with 75 mL of 10% aqueous sodium hydroxide, and then with 100 mL of dilute acid. The ether solution was dried (MgSO$_4$) and concentrated in vacuo to afford 0.62 g (100%) of an off-white foam. The foam was dissolved in ca. 15 mL of methanolic hydrogen chloride. After 5 minutes, the solution was concentrated in vacuo to an oil, and the oil was purified by flash silica chromatography. Elution with dichloromethane: dichloromethane-methanol (99:1) afforded 0.2233 g (42%) of a yellow powder. The powder was dissolved in diethyl ether and washed with dilute hydrochloric acid. The organic phase was dried (MgSO$_4$) and concentrated in vacuo to afford 0.200 g of a foam. This product was triturated with pentane to afford 0.1525 g of a powder that was repurified by flash silica chromatography. Elution with dichloromethane afforded 0.0783 g (15%) of an analytically pure title compound, mp 80–90° C.;

$^1$H NMR (400 MHz, DMSO): δ 11.53 (s, 1H), 9.38 (s, 1H), 8.82 (s, 1H), 7.70 (dd, 1H, J=7.0, 1.9 Hz), 7.53 (s, 1H), 7.37 (dd, 1H, J=8.4, 1.9 Hz), 6.55 (dd, 1H, J=8.2, 6.5 Hz), 2.22 (s, 3H); $^{19}$F NMR (376 MHz, DMSO): δ −126.24 to −126.29 (m), −137.71 to −137.77 (m); IR (KBr) 3346 (broad, O—H stretch), 1651 (C=O stretch)cm$^{-1}$; MS (CI) M+1=484. Analysis calculated for $C_{14}H_{10}BrF_2IN_2O_2$: C, 34.81; H, 2.09; N, 5.80. Found: C, 34.53; H, 1.73; N, 5.52.

Examples 3a to 12a in the table below were prepared by the general procedure of Examples 1 a and 2a.

EXAMPLES 13a–77a

Examples 13a to 77a were prepared utilizing combinatorial synthetic methodology by reacting appropriately substituted phenylamino benzoic acids (e.g., as shown in Scheme 1) and hydroxylamines (e.g., (NHR$_{6a}$)—O—R$_{7a}$). A general method is given below:

To a 0.8-mL autosampler vial in a metal block was added 40 μL of a 0.5 M solution of the acid in DMF and 40 μL of the hydroxylamine (2 M solution in Hunig's base and 1 M in amine in DMF). A 0.5 M solution of PyBrOP was freshly prepared, and 50 μL were added to the autosampler vial. The reaction was allowed to stand for 24 hours.

The reaction mixture was transferred to a 2-dram vial and diluted with 2 mL of ethyl acetate. The organic layer was washed with 3 mL of distilled water and the water layer washed again with 2 mL of ethyl acetate. The combined organic layers were allowed to evaporate to dryness in an open fume hood.

The residue was taken up in 2 mL of 50% acetonitrile in water and injected on a semi-prep reversed phase column (10 mm×25 cm, 5 gM spherical silica, pore Size 115 A derivatized with C-18, the sample was eluted at 4.7 mL/min with a linear ramp to 100% acetonitrile over 8.5 minutes. Elution with 100% acetonitrile continued for 8 minutes.) Fractions were collected by monitoring at 214 nM. The desired fractions were evaporated using a Zymark Turbovap. The product was dissolved in chloroform and transferred to a preweighed vial, evaporated, and weighed again to determine the yield. The structure was confirmed by mass spectroscopy.

EXAMPLES 3a–77a

| Example No. | Compound | Melting Point (° C.) | MS (M − H$^+$) |
|---|---|---|---|
| 3a | 2-(4-bromo-2-methyl-phenylamino)-4-fluoro-N-hydroxy-benzamide | 56–75 dec | 523 |
| 4a | 5-Chloro-N-hydroxy-2-(4-iodo-2-methyl-phenylamino)-benzamide | 65 dec | |
| 5a | 5-Chloro-N-hydroxy-2-(4-iodo-2-methyl-phenylamino)-N-methyl-benzamide | 62–67 | |
| 6a | 5-Chloro-2-(4-iodo-2-methyl-phenylamino)-N-(terahydropyran-2-yloxy)benzamide | 105–108 | |
| 7a | 5-Chloro-2-(4-iodo-2-methyl-phenylamino)-N-methoxybenzamide | 64–68 | |
| 8a | 4-Fluoro-N-hydroxy-2-(4-fluoro-2-methyl-phenylamino)-benzamide | 119–135 | |
| 9a | 4-Fluoro-N-hydroxy-2-(2-methyl phenylamino)-benzamide | 101–103 | |
| 10a | 4-Fluoro-2-(4-fluor-2-methyl-phenylamino)-N-(terahydropyran-2-yloxy)benzamide | 142–146 | |
| 11a | 4-Fluoro-N-hydroxy-2-(4-cluoro-2-methyl-phenylamino)-benzamide | 133.5–135 | |
| 12a | 4-Fluoro-2-(4-iodo-2-methyl-phenylamino)-N-phenylmethoxy-benzamide | 107–109.5 | |
| 13a | 4-Fluoro-2-(4-iodo-2-methyl-phenylamino)-N-methoxy-benzamide | | 399 |
| 14a | 3,4-Difluoro-2-(4-iodo-2-methyl-phenylamino)-N-methoxy-benzamide | | 417 |
| 15a | 2-(4-Bromo-2-methyl-phenylamino)-3,4-difluoro-N-methoxy-benzamide | | 369 |
| 16a | 2-(4-Bromo-2-methyl-phenylamino)-N-ethoxy-3,4-difluoro-benzamide | | 342* (M-EtO) |
| 17a | 5-Bromo-N-ethoxy-3,4-difluoro-2-(4-iodo-2-methyl-phenylamino)-benzamide | | 509 |
| 18a | 3,4-Difluoro-2-(4-iodo-2-methyl-phenylamino)-N-isopropoxy-benzamide | | 445 |
| 19a | 2-(4-Bromo-2-methyl-phenylamino)-3,4-difluoro-N-isopropoxy-benzamide | | 397 |
| 20a | 4-Fluoro-N-(furan-3-ylmethoxy)-2-(4-iodo-2-methyl-phenylamino)-benzamide | | 465 |
| 21a | 3,4-Difluoro-N-(furan-3-ylmethoxy)-2-(4-iodo-2-methyl-phenylamino)-benzamide | | 483 |
| 22a | 2-(4-Bromo-2-methyl-phenylamino)-3,4-difluoro-N-(furan-3-ylmethoxy)-benzamide | | 435 |
| 23a | 5-Bromo-3,4-difluoro-N-(furan-3-ylmethoxy)-2-(4-iodo-2-methyl-phenylamino)-benzamide | | 561 |
| 24a | 5-Bromo-N-(but-2-enyloxy)-3,4-difluoro-2-(4-iodo-2-methyl-phenylamino)-benzamide | | 536 |
| 25a | 4-Fluoro-2-(4-iodo-2-methyl-phenylamino)-N-(prop-2-ynyloxy)-benzamide | | 423 |
| 26a | 3,4-Difluoro-2-(4-iodo-2-methyl-phenylamino)-N-prop-2-ynyloxy)-benzamide | | 441 |
| 27a | 3,4-Difluoro-2-(4-iodo-2-methyl-phenylamino)-N-(1-methyl-prop-2-ynyloxy)-benzamide | | 455 |
| 28a | 2-(4-Bromo-2-methyl-phenylamino)-3,4-difluoro-N-(1-methyl-prop-2-ynyloxy)-benzamide | | 407 |
| 29a | N-(But-3-ynyloxy)-3,4-difluoro-2-(4-iodo-2-methyl-phenylamino)-benzamide | | 455 |
| 30a | 2-(4-Bromo-2-methyl-phenylamino)-N-(but-3-ynyloxy)-3,4-difluoro-benzamide | | 407 |
| 31a | 5-Bromo-N-(but-3-ynyloxy)-3,4-difluoro-2-(4-iodo-2-methyl-phenylamino)-benzamide | | 533 |
| 32a | 3,4-Difluoro-2-(4-iodo-2-methyl-phenylamino)-N-(3-phenyl-prop-2-ynyloxy)-benzamide | | 517 |
| 33a | 3,4-Difluoro-2-(4-bromo-2-methyl-phenylamino)-N-(3-phenyl-prop-2-ynyloxy)-benzamide | | 469 |
| 34a | 3,4-Difluoro-N-[3-(3-fluoro-phenyl)-prop-2-ynyloxy]-2-(4-iodo-2-methyl-phenylamino)-benzamide | | 535 |

| Example No. | Compound | Melting Point (° C.) | MS (M − H⁺) |
|---|---|---|---|
| 35a | 2-(4-Bromo-2-methyl-phenylamino)-3,4-difluoro-N-[3-(3-fluoro-phenyl)-prop-2-ynyloxy]-benzamide | | 487 |
| 36a | 3,4-Difluoro-N-[3-(2-fluoro-phenyl)-prop-2-ynyloxy]-2-(4-iodo-2-methyl-phenylamino)-benzamide | | 535 |
| 37a | 5-Bromo-3,4-difluoro-N-[3-(2-fluoro-phenyl)-prop-2-ynyloxy]-2-(4-iodo-2-methyl-phenylamino)-benzamide | | 613 |
| 38a | 3,4-Difluoro-2-(4-iodo-2-methyl-phenylamino)-N-(3-methyl-5-phenyl-pent-2-en-4-ynyloxy)-benzamide | | 557**(M + H) |
| 39a | 2-(4-Bromo-2-methyl-phenylamino)-3,4-difluoro-N-(3-methyl-5-phenyl-pent-2-en-4-ynyloxy)-benzamide | | 510 |
| 40a | N-Ethoxy-3,4-difluoro-2-(4-iodo-2-methyl-phenylamino)-benzamide | | 431 |
| 41a | 2-(4-Bromo-2-methyl-phenylamino)-N-ethoxy-3,4-difluoro-benzamide | | 383 |
| 42a | 4-Fluoro-2-(4-iodo-2-methyl-phenylamino)-N-propoxy-benzamide | | 427 |
| 43a | 3,4-Difluoro-2-(4-iodo-2-methyl-phenylamino)-N-propoxy-benzamide | | 445 |
| 44a | 2-(4-Bromo-2-methyl-phenylamino)-3,4-difluoro-N-propoxy-benzamide | | 397 |
| 45a | 5-Bromo-3,4-difluoro-2-(4-iodo-2-methyl-phenylamino)-N-propoxy-benzamide | | 523 |
| 46a | 4-Fluoro-2-(4-iodo-2-methyl-phenylamino)-N-isopropoxy-benzamide | | 427 |
| 47a | 3,4-Difluoro-2-(4-iodo-2-methyl-phenylamino)-N-isopropoxy-benzamide | | 445 |
| 48a | 2-(4-Bromo-2-methyl-phenylamino)-3,4-difluoro-N-isopropoxy-benzamide | | 397 |
| 49a | 5-Bromo-3,4-difluoro-2-(4-iodo-2-methyl-phenylamino)-N-isopropoxy-benzamide | | 523 |
| 50a | N-Cyclobutyloxy-3,4-difluoro-2-(4-iodo-2-methyl-phenylamino)-benzamide | | 457 |
| 51a | 2-(4-Bromo-2-methyl-phenylamino)-N-cyclobutyloxy-3,4-difluoro-benzamide | | 409 |
| 52a | N-Cyclopentyloxy-4-fluoro-2-(4-iodo-2-methyl-phenylamino)-benzamide | | 453 |
| 53a | N-Cyclopentyloxy-3,4-difluoro-2-(4-iodo-2-methyl-phenylamino)-benzamide | | 471 |
| 54a | 2-(4-Bromo-2-methyl-phenylamino)-N-cyclopentyloxy-3,4-difluoro-benzamide | | 423 |
| 55a | N-Cyclopropylmethoxy-4-fluoro-2-(4-iodo-2-methyl-phenylamino)-benzamide | | 439 |
| 56a | N-Cyclopropylmethoxy-3,4-difluoro-2-(4-iodo-2-methyl-phenylamino)-benzamide | | 457 |
| 57a | 2-(4-Bromo-2-methyl-phenylamino)-N-cyclopropylmethoxy-3,4-difluoro-benzamide | | 409 |
| 58a | 5-Bromo-N-cyclopropylmethoxy-3,4-difluoro-2-(4-iodo-2-methyl-phenylamino) | | 435 |
| 59a | 4-Fluoro-2-(4-iodo-2-methyl-phenylamino)-N-(2-phenoxy-ethoxy)-benzamide | | 505 |
| 60a | 3,4-Difluoro-2-(4-iodo-2-methyl-phenylamino)-N-(2-phenoxy-ethoxy)-benzamide | | 523 |
| 61a | 2-(4-Bromo-2-methyl-phenylamino)-3,4-difluoro-N-(2-phenoxy-ethoxy)-benzamide | | 475 |
| 62a | 4-Fluoro-2-(4-iodo-2-methyl-phenylamino)-N-(thiophen-2-ylmethoxy)-benzamide | | 481 |
| 63a | 3,4-Difluoro-2-(4-iodo-2-methyl-phenylamino)-N-(thiophen-2-ylmethoxy)-benzamide | | 499 |
| 64a | 2-(4-Bromo-2-methyl-phenylamino)-3,4-difluoro-N-(thiophen-2-ylmethoxy)-benzamide | | 451 |
| 65a | 4-Fluoro-2-(4-iodo-2-methyl-phenylamino)-N-(2-methyl-allyloxy)-benzamide | | 439 |
| 66a | 3,4-Difluoro-2-(4-iodo-2-methyl-phenylamino)-N-(2-methyl-allyloxy)-benzamide | | 457 |
| 67a | 2-(4-Bromo-2-methyl-phenylamino)-3,4-difluoro-N-(2-methyl-allyloxy)-benzamide | | 410 |
| 68a | N-(But-2-enyloxy)-4-fluoro-2-(4-iodo-2-methyl-phenylamino)-benzamide | | 439 |
| 69a | N-(But-2-enyloxy)-3,4-difluoro-2-(4-iodo-2-methyl-phenylamino)-benzamide | | 457 |
| 70a | 2-(4-Bromo-2-methyl-phenylamino)-N-(but-2-enyloxy)-3,4-difluoro-benzamide | | 410 |
| 71a | 3,4-Difluoro-2-(4-iodo-2-methyl-phenylamino)-N-(prop-2-ynyloxy)-benzamide | | 441 |
| 72a | N-(But-3-ynyloxy)-3,4-difluoro-2-(4-iodo-2-methyl-phenylamino)-benzamide | | 455 |
| 73a | 2-(4-Bromo-2-methyl-phenylamino)-N-(4,4-dimethyl-pent-2-ynyloxy)-3,4-difluoro-benzamide | | 449 |
| 74a | N-(But-2-enyloxy)-3,4-difluoro-2-(4-iodo-2-methyl-phenylamino)-benzamide | | 457 |
| 75a | 2-(4-Bromo-2-methyl-phenylamino)-N-(but-2-enyloxy)-3,4-difluoro-benzamide | | 410 |
| 76a | N-(3-tert-butyl-propyn-2-yl)oxy-4-fluoro-2-(4-iodo-2-methyl-phenylamino)-benzamide | | 479 |
| 77a | 4-Fluoro-2-(4-iodo-2-methyl-phenylamino)-N-phenylmethoxy-benzamide | | 577 |

PHYSICAL DATA FOR SELECTED COMPOUNDS

PD 0171984 mp 80–90° C.

PD 0184161 mp 174–175° C.

PD 0203311 mp 141–144° C.

PD 0297189 mp 167–169° C.

¹H-NMR (400MHz; DMSO) δ 11.70 (s, 1H), 8.59 (s, 1H), 7.55 (s, 1H), 7.43 (d, 1H, J=6.5Hz), 7.27 (d, 1H, J=8.7Hz), 6.46 (m, 1H), 3.42 (d, 2H, J=7.0Hz), 0.84 (m, 1H), 0.27 (m, 2H), 0.00 (m, 2H)

PD 0297190 mp 125.5–133° C.

¹H-NMR (400MHz; DMSO) δ 11.48 (s, 1H), 8.32 (s, 1H), 7.34 (d, 1H, J=7.5Hz), 7.28 (d, 2H, J=8.2Hz), 6.48 (d, 2H, J=7.7Hz), 3.32 (d, 2H, J=6.8Hz), 0.81 (m, 1H), 0.28 (m, 2H), 0.00 (m, 2H)

-continued

PHYSICAL DATA FOR SELECTED COMPOUNDS

PD 0296771 mp 266.7–268.9° C.
$^1$H-NMR (400MHz; DMSO) δ 13.85 (broad s, 1H), 8.99 (s, 1H), 7.87 (dd, 1H, J=7.9, 2.1Hz), 7.55 (d, 2H, J=8.6Hz), 6.82 (dd, 2H, J=8.7, 2.8Hz)

PD 0296770 mp 293.2–296.3° C.
$^1$H-NMR (400MHz; DMSO) δ 14.05 (broad s, 1H), 9.21 (s, 1H), 7.93 (dd, 1H, J=7.8, 2.2Hz), 7.82 (d, 1H, J=1.9Hz), 7.54 (dd, 1H, J=8.6, 1.9Hz), 6.82 (dd, 1H, J=8.6, 6.7Hz)

PD 0296767 mp 249–251° C.
$^1$H-NMR (400MHz; DMSO) δ 13.99 (broad s, 1H), 9.01 (s, 1H), 7.90 (dd, 1H, J=7.9, 2.3Hz), 7.58 (d, 1H, J=1.6Hz), 7.42 (dd, 1H, J=8.4, 1.9Hz), 6.69 (dd, 1H, J=8.4, 6.0Hz), 2.24 (s, 3H)

PD298127 mp 127–135° C.
5-chloro-N-cyclopropyl methoxy-3,4-difluoro-2-[4-iodo-2-methyl phenylamino]benzamide
Proton NMR (440MHz; DMSO) δ 11.64 (s, 1H), 8.28 (s, 1H), 7.38 (dd, 1H, J=7.6, 1.7Hz), 7.31 (d, 1H, J=1.2Hz), 7.15 (dd, 1H, J=8.5, 1.7Hz), 3.35 (d, 2H, J=7.3Hz), 2.01 (s, 3H), 0.83 (m, 1H), 0.28 (m, 2H), 0.01 (m, 2H)

BIOLOGICAL ASSAYS

The ability of MEK inhibitors described above to prevent and treat asthma has been demonstrated in three different assays: (1) inhibition of antigen-induced interleukin-5 (IL-5) production in vitro, (2) inhibition of the passive-transfer of eosinophilic lung inflammation in vivo, and (3) inhibition of active eosinophilic lung inflammation in vivo. For each of these assays, female C57BL/6 mice obtained from the Jackson Laboratory (Bar Harbor, Me.) were given an intraperitoneal (i.p.) injection of ovalbumin (OVA, Grade V, Sigma Chemical Company, St. Louis, Mo.) adsorbed to aluminum hydroxide (10 μg OVA+9 mg aluminum hydroxide in 200 μL saline). This sensitizes OVA-specific lymphocytes for subsequent restimulation either in vivo or in vitro.

The first set of experiments was designed to determine whether the MEK inhibitors could prevent antigen-induced production of IL-5 by the OVA-primed splenocytes in vitro. IL-5 is required for the differentiation, migration, and survival of pulmonary eosinophils, which are thought to be responsible for much of the pathology associated with human asthma. In order to examine the effects of MEK inhibitors on IL-5 production, OVA-sensitized mice were sacrificed by cervical dislocation 14 days after sensitization (Day 14), the spleens were excised and disaggregated, and the erythrocytes were lysed. The splenocytes were washed and resuspended at 5×1016 cells/mL in complete medium consisting of RPMI 1640 (Gibco BRL, Gaithersburg, Md.) with 10% heat-inactivated fetal calf serum (Hyclone, Logan, Utah), 55 μM 2-mercaptoethanol, 50 U/mL penicillin G, 50 μg/mL streptomycin sulfate, and 2 mM L-glutamine (Gibco BRL). The splenocytes were then cultured at 37° C. in the presence of 200 μg/mL OVA. MEK inhibitors were also added to the cultures from sterile 10 mM stock solutions (in DMSO). After 3 days, the culture medium was recovered and assayed for IL-5 by specific ELISA. The results of the analysis of IL-5 inhibition are presented in Table 1. All MEK inhibitors tested were found to potently inhibit antigen-induced IL-5 production.

TABLE 1

The Effects of MEK Inhibitors on Antigen-Induced IL-5 Production

| MEK Inhibitor | $IC_{50}$ (nM) |
| --- | --- |
| PD 184386 | 23 |
| PD 171984 | 117 |
| PD 170611 | 1,121 |
| PD 184161 | 1,147 |
| PD 177168 | 1,205 |
| PD 184352 | 1,622 |
| PD 098059 | 17,440 |

When OVA-sensitized spleen cells are restimulated with OVA in vitro for 3 days, as described above, the spleen cells not only produce IL-5, but also acquire the ability to induce eosinophilic lung inflammation when transferred into naive recipient mice. The critical cell type responsible for this adoptively-transferred activity is thought to be IL-5-producing T lymphocytes. Because the results of the first set of experiments indicated that the MEK inhibitors inhibited IL-5 production by cultured splenocytes, a second set of experiments was initiated to determine whether the MEK inhibitor-treated cells were capable of transferring eosinophilic lung inflammation to naive mice. Splenocytes from OVA restimulation cultures, with or without the addition of MEK inhibitors were harvested after 3 days of culture, washed three times, and resuspended at 1×10$^8$ cells/mL in sterile saline. Groups of five naive (unsensitized) C57BL/c mice were injected i.p. with 200 μL of the cell suspension (2×10$^7$ cells). Three days after transfer of cells, the recipient mice were challenged with a 12-minute inhalation of an aerosol formulation of 1.5% OVA in saline (weight/volume), the mist being produced by a nebulizer (small particle generator model SPAG-2, ICN Pharmaceuticals, Costa Mesa, Calif.). Three days after aerosol challenge, the mice were anesthetized with an i.p. injection of an anesthetic mixture comprising Ketamine, acepromazine, and xylazine. The trachea of each mouse was exposed and cannulated. The lungs and upper airways were lavaged with 0.5 mL of cold (5° C.) phosphate buffered saline (PBS). The cells within a 200 μL portion of the bronchoalveolar lavage (BAL) fluid were enumerated using a Coulter counter (Model ZB 1, Coulter Electronics, Hialeah, Fla.). The remaining BAL fluid was then centrifuged at 300×g for 5 minutes, and the cells resuspended in 1 mL of Hank's balanced salt solution (HBSS, Gibco BRL), containing 0.5% fetal calf serum, and 10 mM of N-2-hydroxyethylpiperazine-N-2-ethanesulfonic acid (HEPES, Gibco BRL). The cell suspension (100 μL) was centrifuged in a cytospin (Shandon Southern Instruments, Sewickley, Pa.) and stained with Diff Quick to distinguish neutrophil, eosinophil, monocyte, and lymphocyte subsets. The number of eosinophils in the BAL fluid was determined by multiplying the percentage of eosinophils by the total cell count.

As shown in Table 2, OVA-sensitized splenocytes cultured in the absence of MEK inhibitor, when transferred to naive recipient mice, were able to promote eosinophilic lung inflammation in response to an aerosol challenge with OVA. In contrast, splenocytes cultured in the presence of the MEK inhibitors PD 171984, PD 184352, and PD 184386 (10 μM each) did not promote eosinophilic lung inflammation (>99% inhibition). For each of the MEK inhibitors used, a 10 μM concentration was previously found to inhibit IL-5 production by over 75% (Table 1). These results suggest that the MEK inhibitors inhibit the IL-5-producing T lymphocytes that are required to support asthma-like eosinophilic lung inflammation in mice.

TABLE 2

The Effects of MEK Inhibitors on the Adoptive-Transfer of Eosinophilic Lung Inflammation Treatment of Spleen Cell Culture

| Compound | Dose ($\mu$M) | % Inhibition of BAL Eosinophils |
|---|---|---|
| None |  | 0 |
| PD 171984 | 10 | 99.82 |
| PD 184386 | 10 | 99.78 |
| PD 184352 | 10 | 99.46 |

The final set of experiments was designed to test whether MEK inhibitors could inhibit active OVA-induced eosinophilic lung inflammation in mice. Mice were sensitized with OVA/aluminum hydroxide on Day 0 as described above. On Day 14, the mice were challenged by aerosol with 1.5% OVA, as described above for the adoptive-transfer recipients. One group of eight sensitized mice was dosed orally with vehicle (0.5% hydroxypropylmethylcellulose/0.25% TWEEN-80). Other groups of sensitized mice (8 mice per group) were given oral doses of a MEK inhibitor. The test compound was dissolved in the vehicle, and the volume for each dosage was adjusted to 200 $\mu$L, so that each test animal received the same oral volume. In experiments reported in Table 3 and Table 4, the MEK inhibitor was administered starting on Day 13 (ie, 13 days after initial sensitization and 1 day prior to aerosol challenge), and continued daily through Day 16 (4 days total). In experiments reported in Table 5, the MEK inhibitor was administered starting on Day 7 (ie, 7 days after initial sensitization and 7 days prior to aerosol challenge), and continued daily through Day 16 (9 days total). On Day 17 of each experiment (17 days following the initial OVA challenge, and 3 days after the OVA aerosol challenge), all animals including controls were anesthetized, cannulated, and lavaged as previously described. The number of BAL eosinophils was determined as described above.

In the initial analysis of active OVA-induced lung inflammation, multiple MEK inhibitors (PD 171984, PD 177168, PD 184161, PD 184386, and PD 184352) were dosed orally for 4 days. Only one compound, PD 171984, demonstrated any inhibition of pulmonary eosinophilia (Table 3). PD 171984, along with PD 184352, were tested again at multiple doses, again dosing for only 4 days. The results in Table 4 essentially parallel those in Table 3 for these compounds; PD 171984 appears active, whereas PD 184352 does not. As reported in Table 5, increasing the oral dosing schedule from 4 days to 9 days (7 days prior to aerosol challenge, 2 days after) resulted in a degree of inhibitory activity for PD 184352 at 100 mg/kg (59.85% inhibition, p=0.11). PD 171984 continued to demonstrate statistically significant inhibitory activity under this dosing regimen.

In total, these results indicate that MEK inhibitors, when used in vitro, are potent inhibitors of IL-5 production, and completely inhibit the ability of antigen-stimulated cells to adoptively transfer asthma-like symptoms to naive recipient mice. When used in vivo, some MEK inhibitors are more active than others.

However, a less potent compound (PD 184352) was shown to inhibit the asthma-like response in mice under a more rigorous dosing regimen. Thus, the foregoing data establish that the selective MEK inhibitors are active in inhibiting a model of asthma in mice. The compounds have little or no toxic effects, and accordingly are particularly well-suited for treating and controlling asthma in children, as well as adults. The compounds will be formulated for convenient oral or parenteral administration, including by aerosol delivery, transdermal delivery, or even suppositories, and will be administered in an antiasthlnatic effective dose, which is that amount that is effective to treat the particular asthma severity for which treatment is needed or otherwise desired.

TABLE 3

The Effect of MEK Inhibitors on Eosinophilic Lung Inflammation in Mice

| MEK Inhibitor | Dose ($\mu$M) | % Inhibition of BAL Eosinophilia |
|---|---|---|
| PD 171984 | 100 | 55.26* |
| PD 177168 | 100 | −23.38 |
| PD 184161 | 100 | −32.53 |
| PD 184386 | 100 | −33.24 |
| PD 184352 | 150 | −5.41 |

*p = 0.08

TABLE 4

Inhibition of BAL Eosinophils With 4-Day Compound Dosing

| | % Inhibition of BAL Eosinophils by: | |
|---|---|---|
| Dose (mg/kg) | PD 184352 | PD 171984 |
| 0 | 0 | 0 |
| 10 | −22.7 | 38.4* |
| 30 | −153.8 | 46.6* |
| 100 | −8.2 | 58.4* |

*Significantly different from control (p < 0.05)

TABLE 5

Inhibition of BAL Eosinophils With 9-Day Compound Dosing

| | % Inhibition of BAL Eosinophils by: | | |
|---|---|---|---|
| | | PD 171984 | |
| Dose (mg/kg) | PD 184352 | Experiment 1 | Experiment 2 |
| 0 | 0 | 0 | 0 |
| 10 | −42.99 | −13.74 | 50.15* |
| 30 | 1.83 | 80.64* | 37.23* |
| 100 | 59.85 | 88.40* | 54.77* |

*Significantly different from control (p < 0.05)

The foregoing data establish that the selective MEK inhibitors are active in both inhibiting and controlling the asthmatic disease, for example, prior to actual challenge and following challenge. The compounds are therefore useful in the prophylaxis of asthma, and also in treating and alleviating the symptoms that accompany the disease during its active stage. The compounds have little or no toxic effects, and accordingly are particularly well-suited for treating and controlling asthma in children, as well as adults. The compounds will be formulated for convenient oral or parenteral administration, including by aerosol delivery, transdermal delivery, or even suppositories, and will be administered in an antiasthmatic effective dose, which is that amount that is effective to treat the particular asthma severity for which treatment is needed or otherwise desired.

D. Other Embodiments

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:

1. A method for preventing or treating asthma in patients, said method comprising the step of administering to a patient in need of treatment, or to a patient suspected of developing asthma and in need of prophylactic treatment, an antiasthmatic effective amount of a phenyl amine compound of Formula I:

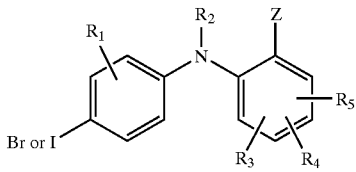

wherein:

$R_1$ is hydrogen, hydroxy, $C_1$–$C_8$ alkyl, $C_1$–$C_8$ alkoxy, halo, trifluoromethyl, or CN;

$R_2$ is hydrogen;

$R_3$, $R_4$, and $R_5$ independently are hydrogen, hydroxy, halo, trifluoromethyl, $C_1$–$C_8$ alkyl, $C_1$–$C_8$ alkoxy, nitro, CN, or —(O or NH)$_m$—(CH$_2$)$_n$—$R_9$, where $R_9$ is hydrogen, hydroxy, COOH, or $NR_{10}R_{11}$;

n is 0–4;

m is 0 or 1;

$R_{10}$ and $R_{11}$ independently are hydrogen or $C_1$–$C_8$ alkyl, or taken together with the nitrogen to which they are attached can complete a 3–10 member cyclic ring optionally containing 1, 2, or 3 additional heteroatoms selected from O, S, NH, or N—$C_1$–$C_8$ alkyl;

Z is COOR$_7$, tetrazolyl, CONR$_6$R$_7$, CONHNR$_{10}$R$_{11}$, or CH$_2$OR$_7$;

$R_6$ and $R_7$ independently are hydrogen, $C_1$–$C_8$ alkyl, $C_2$–$C_8$ alkenyl, $C_2$–$C_8$ alkynyl, (CO)—$C_1$–$C_8$ alkyl, aryl, heteroaryl, $C_3$–$C_{10}$ cycloalkyl, or $C_3$–$C_{10}$ cycloalkyl op tionally containing 1, 2, or 3 heteroatoms selected from O, S, NH, or N alkyl; or $R_6$ and $R_7$ together with the nitrogen to which they are attached complete a 3–10 member cyclic ring optionally containing 1, 2, or 3 additional heteroatoms selected from O, S, NH, or N alkyl;

and wherein any of the foregoing alkyl, alkenyl, aryl, heteroaryl, heterocyclic, and alkynyl groups can be unsubstituted or substituted by halo, hydroxy, $C_1$–$C_6$ alkoxy, amino, nitro, $C_1$–$C_4$ alkylamino, di($C_1$–$C_4$) alkylamino, $C_3$–$C_6$ cycloalkyl, phenyl, phenoxy, $C_3$–$C_5$ heteroaryl or heterocyclic radical, or $C_3$–$C_5$ heteroaryloxy or heterocyclic radical-oxy;

or a pharmaceutically acceptable salt, ester, amide, or pro-drug thereof.

2. The method of claim 1, wherein the phenyl anine compound is a compound of Formula (I) wherein (a) $R_1$ is hydrogen, methyl, methoxy, fluoro, chloro, or bromo; (b) $R_2$ is hydrogen; (c) $R_3$, $R_4$, and $R_5$ independently are hydrogen, fluoro, chloro, bromo, iodo, methyl, methoxy, or nitro; (d) $R_{10}$ and $R_{11}$ independently are hydrogen or methyl; (e) Z is COOR$_7$, tetrazolyl, CONR$_6$R$_7$, CONHNR$_{10}$R$_{11}$, or CH$_2$OR$_7$; $R_6$ and $R_7$ independently are hydrogen, $C_{1-4}$ alkyl, heteroaryl, or $C_{3-5}$ cycloalkyl optionally containing one or two heteroatoms selected from O, S, or NH; or $R_6$ and $R_7$ together with the nitrogen to which they are attached complete a 5–6 member cyclic ring optionally containing 1 or 2 additional heteroatoms selected from O, NH or N-alkyl; and wherein any of the foregoing alkyl or aryl groups can be unsubstituted or substituted by halo, hydroxy, methoxy, ethoxy, or heteroaryloxy; (f) Z is COOR$_7$; (g) R7 is H, pentafluorophenyl, or tetrazolyl; (h) $R_3$, $R_4$, and $R_5$ are independently H, fluoro, or chloro; (i) $R_4$ is fluoro; (j) two of $R_3$, $R_4$, and $R_5$ are fluoro; or (k) or combinations of the above.

3. The method of claim 2, wherein the the phenyl anine compound is a compound of Formula (I) wherein: Z is COOR$_7$; $R_7$ is H, pentafluorophenyl, or tetrazolyl; $R_3$ and $R_5$ are independently H, fluoro, or chloro; and $R_4$ is fluoro.

4. The method of claim 1 wherein the phenyl amine is selected from:

[4-Chloro-2-(1H-tetrazol-5-yl)-phenyl-(4-iodo-2-methyl-phenyl)-amine;

(4-Iodo-2-methyl-phenyl)-[2-(1H-tetrazol-5-yl)-phenyl] amine;

[4-Nitro-2-(1H-tetrazol-5-yl)-phenyl-(4-iodo-2-methyl-phenyl)-amine;

4-Fluoro-2-(4-iodo-2-methylphenylamino)benzoic acid;

3,4,5-Trifluoro-2-(4-iodo-2-methyl-phenylamino)-benzoic acid;

3,4-Difluoro-2-(4-iodo-2-methyl-phenylamino)-benzoic acid;

5-Bromo-3,4-difluoro-2-(4-iodo-2-methyl-phenylamino)-benzoic acid;

5-Chloro-2-(4-iodo-2-methyl-phenylamino)-benzoic acid;

Sodium 5-Chloro-2-(4-iodo-2-methyl-phenylamino)-benzoate;

5-Bromo-2-(4-iodo-2-methyl-phenylamino)-benzoic acid;

2-(4-Iodo-2-methyl-phenylamino)-5-nitro-benzoic acid;

4-Chloro-2-(4-iodo-2-methyl-phenylamino)-benzoic acid;

2-(4-Iodo-2-methyl-phenylamino)-benzoic acid;

5-Fluoro-2-(4-iodo-2-methyl-phenylamino)-benzoic acid;

5-Iodo-2-(4-iodo-2-methyl-phenylamino)-benzoic acid;

2-(4-Iodo-phenylamino)-5-methoxy-benzoic acid;

5-Methyl-2-(4-iodo-2-methyl-phenylamino)-benzoic acid;

2-(4-Iodo-2-methyl-phenylamino)-4-nitro-benzoic acid;

2-(4-Bromo-2-methyl-phenylamino)-4-fluoro-benzoic acid;

2-(2-Bromo-4-iodo-phenylamino)-5-nitro-benzoic acid;

2-(4-Bromo-2-methyl-phenylamino)-3,4-difluoro-benzoic acid;

5-Chloro-N-(2-hydroxyethyl)-2-(4-iodo-2-methyl-phenylamino)-benzamide;

4-Fluoro-2-(4-iodo-2-methyl-phenylamino)-benzamide;

4-Fluoro-2-(4-iodo-2-methyl-phenylamino)-N-methyl-benzamide;

N-Ethyl-4-fluoro-2-(4-iodo-2-methyl-phenylamino)-benzamide;
4-Fluoro-2-(4-iodo-2-methyl-phenylamino)-N,N-dimethyl-benzamide;
4-Fluoro-2-(4-iodo-2-methyl-phenylamino)-N-(1H-tetrazol-5-yl)-benzamide;
5-Bromo-2-(4-iodo-2-methyl-phenylamino)-benzamide;
5-Chloro-2-(4-iodo-2-methyl-phenylamino)-N,N-dimethyl-benzamnide;
5-Chloro-2-(4-iodo-2-methyl-phenylamino)-N-hydroxycarbonylmethyl-benzamide;
4-Fluoro-2-(4-iodo-2-methyl-phenylamino)-N-propyl-benzamide;
5-Bromo-N-(2-hydroxy-ethyl)-2-(4-iodo-2-methyl-phenylamino)-benzamide;
N,N-Diethyl-4-fluoro-2-(4-iodo-2-methyl-phenylamino)-benzamide;
4-Fluoro-N-{3-[4-(2-hydroxy-ethyl)-piperazin-1-yl]-propyl)}-2-(4-iodo-2-methyl-phenylamino)-benzamnide;
N,N-Diethyl-2-(4-iodo-2-methyl-phenylamino)-5-nitro-benzamide;
N-Butyl-4-fluoro-2-(4-iodo-2-methyl-phenylamino)-benzamide;
5-Chloro-N,N-diethyl-2-(4-iodo-2-methyl-phenylamino)-benzamide;
5-Bromo-2-(4-iodo-2-methyl-phenylamino)-N,N-dimethyl-benzamide;
5-Bromo-3,4-difluoro-N-(2-hydroxy-ethyl)-2-(4-iodo-2-methyl-phenylamino)-benzamide;
N-(2,3-Dihydroxy-propyl)-3,4-difluoro-2-(4-iodo-2-methyl-phenylamino)-benzamide;
5-Bromo-3,4-difluoro-2-(4-iodo-2-methyl-phenylamino)-N-(2-piperidin-1-yl-ethyl)-benzamide;
3,4-Difluoro-N-(2-hydroxy-ethyl)-2-(4-iodo-2-methyl-phenylamino)-benzamide;
N-(2,3-Dihydroxy-propyl)-4-fluoro-2-(4-iodo-2-methyl-phenylamino)-benzamide;
3,4-Difluoro-N-(3-hydroxy-propyl)-2-(4-iodo-2-methyl-phenylamino)-benzamnide;
5-Bromo-3,4-difluoro-2-(4-iodo-2-methyl-phenylamino)-N-(2-pyrrolidin-1-yl-ethyl)-benzamide;
5-Bromo-3,4-difluoro-2-(4-iodo-2-methyl-phenylamino)-N-(2-pyridin-4-yl-ethyl)-benzamide;
4-Fluoro-N-(2-hydroxy-ethyl)-2-(4-iodo-2-methyl-phenylamino)-benzamide;
5-Bromo-N-(3-dimethylamino-propyl)-3,4-difluoro-2-(4-iodo-2-methyl-phenylamino)-benzamide;
5-Bromo-3,4-difluoro-2-(4-iodo-2-methyl-phenylamino)-N-(2-morpholin-4-yl-ethyl)-benzamide;
3,4-Difluoro-2-(4-iodo-2-methyl-phenylamino)-N-(2-morpholin-4-yl-ethyl)-benzamide;
3,4-Difluoro-2-(4-iodo-2-methyl-phenylamino)-N-(2-pyrrolidin-1-yl-ethyl)-benzamide;
3,4-Difluoro-2-(4-iodo-2-methyl-phenylamino)-N-(2-pyridin-4-yl-ethyl)-benzamide;
N-(3-Dimethylamino-propyl)-3,4-difluoro-2-(4-iodo-2-methyl-phenylamino)-benzamide;
N-Benzyl-4-fluoro-2-(4-iodo-2-methyl-phenylamino)-benzamide;
2-(4-Bromo-2-methyl-phenylamino)-3,4-difluoro-N-(2-hydroxy-ethyl)-benzamide;
4-Fluoro-2-(4-iodo-2-methyl-phenylamino)-N-(2-morpholin-4-yl-ethyl)-benzamide;
4-Fluoro-2-(4-iodo-2-methyl-phenylamino)-N-(3-piperidin-1-yl-propyl)-benzamide;
3,4-Difluoro-2-(4-iodo-2-methyl-phenylamino)-N-(3-piperidin-1-yl-propyl)-benzamide;
4-Fluoro-2-(4-iodo-2-methyl-phenylamino)-N-(2-thiophen-2-yl-ethyl)-benzamide;
4-Fluoro-2-(4-iodo-2-methyl-phenylamino)-N-(2-pyrrolidin-1-yl-ethyl)-benzamide;
2-(4-Bromo-2-methyl-phenylamino)-3,4-difluoro-N-(2-morpholin-4-yl-ethyl)-benzamide;
5-Bromo-3,4-difluoro-2-(4-iodo-2-methyl-phenylamino)-N-pyridin-4-ylmethyl-benzamide;
3,4-Difluoro-2-(4-iodo-2-methyl-phenylamino)-N-pyridin-4-ylmethyl-benzamide;
2-(4-Bromo-2-methyl-phenylamno)-N-(3-dimethylamino-propyl)-3,4-difluoro-benzamide;
4-Fluoro-2-(4-iodo-2-methyl-phenylamino)-N-pyridin-4-ylmethyl-benzamide;
4-Fluoro-2-(4-iodo-2-methyl-phenylamino)-N-(2-pyridin-4-yl-ethyl)-benzamide;
2-(4-Bromo-2-methyl-phenylamino)-3,4-difluoro-N-(2-pyridin-4-yl-ethyl)-benzamide;
2-(4-Bromo-2-methyl-phenylamino)-3,4-difluoro-N-(3-hydroxy-propyl)-benzamide;
2-(4-Bromo-2-methyl-phenylamino)-3,4-difluoro-N-(2-pyrrolidin-1-yl-ethyl)-benzamide;
4-Fluoro-2-(4-iodo-2-methyl-phenylamino)-N-phenethyl-benzamide;
2-(4-Bromo-2-methyl-phenylamino)-3,4-difluoro-N-(2-thiophen-2-yl-ethyl)-benzamide;
2-(4-Bromo-2-methyl-phenylamino)-3,4-difluoro-N-pyridin-4-ylmethyl-benzamide;
2-(4-Bromo-2-methyl-phenylamino)-3,4-difluoro-N-phenethyl-benzamide;
2-(4-Bromo-2-methyl-phenylamino)-3,4-difluoro-N-(2-piperidin-1-yl-ethyl)-benzamide;
5-Chloro-N-{3-[4-(2-hydroxy-ethyl)-piperazin-1-yl]-propyl}-2-(4-iodo-2-methyl-phenylamino)-benzamide;
5-Fluoro-N-{3-[4-(2-hydroxy-ethyl)-piperazin-1-yl]-propyl}-2-(4-iodo-2-methyl-phenylamino)-benzamide;
2-(4-Iodo-2-methyl-phenylamino)-5-nitro-N-pyridin-4-yl methyl-benzamide;
5-Bromo-N-{3-[4-(2-hydroxy-ethyl)-piperazin-1-yl]-propyl}-2-(4-iodo-2-methyl-phenylamino)-benzamide;
5-Chloro-N-(2-diethylamino-ethyl)-2-(4-iodo-2-methyl-phenylamino)-benzamnide;
5-Chloro-2-(4-iodo-2-methyl-phenylamino)-N-(2-piperidin-1-yl-ethyl)-benzamide;
(3-Hydroxy-pyrrolidin-1-yl)-[2-(4-iodo-2-methyl-phenylamino)-5-nitro-phenyl]-methanone;
5-Chloro-2-(4-iodo-2-methyl-phenylamino)-N-(2-pyrrolidin-1-yl-ethyl)-benzamide;
5-Bromo-N-(2-diethylamino-ethyl)-2-(4-iodo-2-methyl-phenylamino)-benzamide;
N-{2-[Bis-(2-hydroxy-ethyl)-amino]-ethyl}-5-chloro-2-(4-iodo-2-methyl-phenylamino)-benzamide;
N-{2-[Bis-(2-hydroxy-ethyl)-amino]-ethyl}-5-bromo-2-(4-iodo-2-methyl-phenylamino)-benzamide;
N-{3-[4-(2-Hydroxy-ethyl)-piperazin-1-yl]-propyl}-2-(4-iodo-2-methyl-phenylamino)-benzamide;

5-Fluoro-2-(4-iodo-2-methyl-phenylamino)-N-pyridin-4-ylmethyl-benzamide;
5-Bromo-2-(4-iodo-2-ethyl-phenylamino)-N-(2-pyrrolidin-1-yl-ethyl)-benzamide;
5-Bromo-2-(4-iodo-2-methyl-phenylamino)-N-(2-piperidin-1-yl-ethyl)-benzamide;
5-Fluoro-2-(4-iodo-2-methyl-phenylamino)-N-(2-pyrrolidin-1-yl-ethyl)-benzamide;
5-Chloro-N-(3-dimethylamino-propyl)-2-(4-iodo-2-methyl-phenylamino)-benzamide;
N-{2-[Bis-(2-hydroxy-ethyl)-amino]-ethyl}-5-fluoro-2-(4-iodo-2-methyl-phenylamino)-benzamide;
5-Chloro-N-(3-hydroxy-propyl)-2-(4-iodo-2-methyl-phenylamino)-benzamide;
5-Chloro-N-(3-diethylamino-2-hydroxy-propyl)-2-(4-iodo-2-methyl-phenylamino)-benzamide;
5-Fluoro-2-(4-iodo-2-methyl-phenylamino)-N-(2-piperidin-1-yl-ethyl)-benzamide;
5-Bromo-N-(3-hydroxy-propyl)-2-(4-iodo-2-methyl-phenylamino)-benzamide;
5-Bromo-2-(4-iodo-2-methyl-phenylamino)-N-(3-piperidin-1-yl-propyl)-benzamide;
N-{2-[Bis-(2-hydroxy-ethyl)-amino]-ethyl}-2-(4-iodo-2-methyl-phenylamino)-5-nitro-benzamide;
5-Chloro-2-(4-iodo-2-methyl-phenylamino)-N-(2-morpholin-4-yl-ethyl)-benzamide;
5-Chloro-N-(3-diethylamino-propyl)-2-(4-iodo-2-methyl-phenylamino)-benzamide;
5-Chloro-N-(2-diisopropylamino-ethyl)-2-(4-iodo-2-methyl-phenylamino)-benzamide;
5-Chloro-2-(4-iodo-2-methyl-phenylamino)-N-(3-piperidin-1-yl-propyl)-benzamide;
2-(4-Iodo-2-methyl-phenylamino)-5-nitro-N-(2-piperidin-1-yl-ethyl)-benzamide;
5-Bromo-2-(4-iodo-2-methyl-phenylamino)-N-(2-piperazin-1-yl-ethyl)-benzamide;
N-(2-Diethylamino-ethyl)-5-fluoro-2-(4-iodo-2-methyl-phenylamino)-benzamide;
5-Bromo-N-(3-dimethylamino-propyl)-2-(4-iodo-2-methyl-phenylamino)-benzamide;
N-(3-Hydroxy-propyl)-2-(4-iodo-2-methyl-phenylamino)-5-nitro-benzamide;
5-Fluoro-N-(3-hydroxy-propyl)-2-(4-iodo-2-methyl-phenylamino)-benzamide;
N-(3-Diethylamino-propyl)-5-fluoro-2-(4-iodo-2-methyl-phenylamino)-benzamide;
N-(3-Diethylamino-propyl)-2-(4-iodo-2-methyl-phenylamino)-5-nitro-benzamide;
5-Bromo-2-(4-iodo-2-methyl-phenylamino)-N-(2-morpholin-4-yl-ethyl)-benzamide;
2-(4-Iodo-2-methyl-phenylamino)-5-nitro-N-(3-piperidin-1-yl-propyl)-benzamide;
[5-Fluoro-2-(4-iodo-2-methyl-phenylamino)-phenyl]-(3-hydroxy-pyrrolidin-1-yl)-methanone
5-Bromo-N-(2-diisopropylamino-ethyl)-2-(4-iodo-2-methyl-phenylamino)-benzamide;
5-Fluoro-2-(4-iodo-2-methyl-phenylamino)-N-(2-morpholin-4-yl-ethyl)-benzamide;
5-Fluoro-2-(4-iodo-2-methyl-phenylamino)-N-(3-piperidin-1-yl-propyl)-benzamide;
[5-Fluoro-2-(4-iodo-2-methyl-phenylamino)-phenyl]-[4-(2-hydroxy-ethyl)-piperazin-1-yl]-methanone;
N-(3-Diethylamino-2-hydroxy-propyl)-5-fluoro-2-(4-iodo-2-methyl-phenylamino)-benzamide;
N-Cyclopropyl-5-fluoro-2-(4-iodo-2-methyl-phenylamino)-benzamide;
5-Chloro-N-(2-hydroxy-ethyl)-2-(4-iodo-2-methyl-phenylamino)-benzamide;
5-Fluoro-N-(2-hydroxy-ethyl)-2-(4-iodo-2-methyl-phenylamino)-benzamnide;
N-Benzyloxy-5-fluoro-2-(4-iodo-2-methyl-phenylamino)-benzamide;
N-Benzyloxy-5-bromo-2-(4-iodo-2-methyl-phenylamino)-benzamide;
2-(4-Iodo-2-methyl-phenylamino)-5-nitro-N-(4-sulfamoyl-benzyl)-benzamide;
5-Bromo-N-(2-hydroxy-ethyl)-2-(4-iodo-2-methyl-phenylamino)-benzamide;
N-(2-Hydroxy-ethyl)-5-iodo-2-(4-iodo-2-methyl-phenylamino)-benzamide;
N-(2-Hydroxy-ethyl)-2-(4-iodo-2-ethyl-phenylamino)-5-nitro-benzamide;
2-(4-Iodo-2-methyl-phenylamino)-N-methyl-5-nitro-N-phenyl-benzamide;
5-Chloro-N-cyclopropyl-2-(4-iodo-2-methyl-phenylamino)-benzamide;
5-Fluoro-2-(4-iodo-2-methyl-phenylamino)-N-methyl-N-phenyl-benzamide;
N-Allyl-5-fluoro-2-(4-iodo-2-methyl-phenylamino)-benzamide;
N-Benzyloxy-5-iodo-2-(4-iodo-2-methyl-phenylamino)-benzamide;
5-Fluoro-2-(4-iodo-2-methyl-phenylamino)-N-(4-sulfamoyl-benzyl)-benzamde;
N-Allyl-5-chloro-2-(4-iodo-2-methyl-phenylamino)-benzamide;
N-Cyclopropyl-2-(4-iodo-2-methyl-phenylamino)-5-nitro-benzamide;
5-Bromo-N-cyclopropyl-2-(4-iodo-2-methyl-phenylamino)-benzamide;
5-Chloro-2-(4-iodo-2-methyl-phenylamino)-N-methyl-N-phenyl-benzamide;
5-Iodo-2-(4-iodo-2-methyl-phenylamino)-N-(4-sulfamoyl-benzyl)-benzamide;
5-Bromo-2-(4-iodo-2-methyl-phenylamino)-N-(4-sulfamoyl-benzyl)-benzamide;
N-Allyl-2-(4-iodo-2-methyl-phenylamino)-5-nitro-benzamide;
2-(4-Iodo-2-methyl-phenylamino)-5-nitro-N-(4-sulfamoyl-benzyl)-benzamide;
N-Allyl-5-bromo-2-(4-iodo-2-methyl-phenylamino)-benzamide;
5-Fluoro-2-(4-iodo-2-methyl-phenylamino)-N-(3-methyl-benzyl)-benzamide;
N-Cyclopropyl-5-iodo-2-(4-iodo-2-methyl-phenylamino)-benzamide;
5-Bromo-2-(4-iodo-2-methyl-phenylamino)-N-methyl-N-phenyl-benzamide;
N-Benzyloxy-2-(4-iodo-2-methyl-phenylamino)-5-nitro-benzamide;
N-Cyclohexyl-5-iodo-2-(4-iodo-2-methyl-phenylamino)-benzamide;
N-Allyl-5-iodo-2-(4-iodo-2-methyl-phenylamino)-benzamide;

5-Iodo-2-(4-iodo-2-methyl-phenylamino)-N-(3-methyl-benzyl)-benzamide;

2-(4-Iodo-2-methyl-phenylamino)-N-(3-methyl-benzyl)-5-nitro-benzamide;

5-Iodo-2-(4-iodo-2-methyl-phenylamino)-N-methyl-N-phenyl-benzamide;

N-Cyclohexyl-5-fluoro-2-(4-iodo-2-methyl-phenylamino)-benzamide;

5-Chloro-N-cyclohexyl-2-(4-iodo-2-methyl-phenylamino)-benzamide;

5-Bromo-2-(4-iodo-2-methyl-phenylamino)-N-(3-methyl-benzyl)-benzamide;

5-Bromo-N-cyclohexyl-2-(4-iodo-2-methyl-phenylamino)-benzamide;

5-Chloro-2-(4-iodo-2-methyl-phenylamino)-N-(3-methyl-benzyl)-benzamide;

N-Cyclohexyl-2-(4-iodo-2-methyl-phenylamino)-5-nitro-benzamide;

N-Benzyloxy-5-bromo-2-(4-iodo-2-methyl-phenylamino)-benzamide;

N-Benzyloxy-5-fluoro-2-(4-iodo-2-methyl-phenylamino)-benzamide;

5-Chloro-N-(2-hydroxy-ethyl)-2-(4-iodo-2-methyl-phenylamino)-benzamide;

5-Bromo-N-(2-hydroxy-ethyl)-2-(4-iodo-2-methyl-phenylamino)-benzamide;

2-(4-Iodo-2-methyl-phenylamino)-N-methyl-5-nitro-N-phenyl-benzamide;

5-Chloro-2-(4-iodo-2-methyl-phenylamino)-N-methyl-N-phenyl-benzamide;

N-(2-Hydroxy-ethyl)-5-iodo-2-(4-iodo-2-methyl-phenylamino)-benzamide;

5-Chloro-N-cyclopropyl-2-(4-iodo-2-methyl-phenylamino)-benzamide;

N-Allyl-5-chloro-2-(4-iodo-2-methyl-phenylanino)-benzamide;

5-Fluoro-2-(4-iodo-2-methyl-phenylamino)-N-methyl-N-phenyl-benzamide;

N-(2-Hydroxy-ethyl)-2-(4-iodo-2-methyl-phenylaniino)-5-nitro-benzamide;

5-Fluoro-N-(2-hydroxy-ethyl)-2-(4-iodo-2-methyl-phenylamino)-benzamide;

5-Bromo-N-cyclopropyl-2-(4-iodo-2-methyl-phenylamino)-benzamide;

N-Cyclopropyl-5-fluoro-2-(4-iodo-2-methyl-phenylamino)-benzamide;

5-Fluoro-2-(4-iodo-2-methyl-phenylamino)-N-(4-sulfamoyl-benzyl)-benzamide;

N-Cyclopropyl-2-(4-iodo-2-methyl-phenylamino)-5-nitro-benzamide;

N-Allyl-5-fluoro-2-(4-iodo-2-methyl-phenylamino)-benzamide;

N-Benzyloxy-5-iodo-2-(4-iodo-2-methyl-phenylamino)-benzamide;

N-Allyl-5-bromo-2-(4-iodo-2-methyl-phenylamino)-benzamide;

5-Bromo-2-(4-iodo-2-methyl-phenylamino)-N-(4-sulfamoyl-benzyl)-benzamide;

5-Bromo-2-(4-iodo-2-methyl-phenylamino)-N-methyl-N-phenyl-benzamide;

N-Allyl-2-(4-iodo-2-methyl-phenylamino)-5-nitro-benzamide;

4-Fluoro-2-(4-iodo-2-methyl-phenylamino)-benzyl alcohol;

[5-Chloro-2-(4-iodo-2-methyl-phenylamino)-phenyl]-methanol;

[2-(4-Iodo-2-methyl-phenylamino)-5-nitro-phenyl]-methanol;

[5-Bromo-2-(4-iodo-2-methyl-phenylamino)-phenyl]-methanol; and

N-Allyl-2-(4-iodo-2-methyl-phenylamino)-5-nitro-benzamide.

5. A method for preventing or treating asthma in patients, said method comprising the step of administering to a patient in need of treatment, or to a patient suspected of developing asthma and in need of prophylactic treatment, an antiasthmatic effective amount of a phenyl amine compound of Formula II:

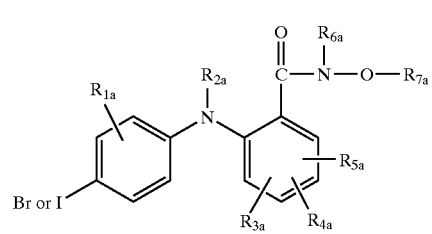

wherein:

$R_{1a}$ is hydrogen, hydroxy, $C_1$–$C_8$ alkyl, $C_1$–$C_8$ alkoxy, halo, trifluoromethyl, or CN;

$R_{2a}$ is hydrogen;

$R_{3a}$, $R_{4a}$ and $R_{5a}$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—$R_9$a, where $R_{9a}$ is hydrogen, hydroxy, CO$_2$H or NR$_{10a}$R$_{11a}$, n is 0–4;

m is 0 or 1;

$R_{10a}$ and $R_{11a}$ independently are hydrogen or $C_1$–$C_8$ alkyl, or taken together with the nitrogen to which they are attached can complete a 3- to 10-member cyclic ring optionally containing one, two, or three additional heteroatoms independently selected from O, S, NH, and N—$C_1$–$C_8$ alkyl;

$R_{6a}$ is hydrogen, $C_1$–$C_8$ alkyl, (CO)—$C_1$–$C_8$ alkyl, aryl, aralkyl, or $C_3$–$C_{10}$ cycloalkyl;

$R_{7a}$ is hydrogen, $C_1$–$C_8$ alkyl, $C_2$–$C_8$ alkenyl, $C_2$–$C_8$ alkynyl, or $C_3$–$C_{10}$ cycloal optionally containing a heteroatom independently selected from O, S and NR$_{9a}$; or R$_6$ and R$_{7a}$ taken together with the N to which they are attached can complete a 5- to 10-membered cyclic ring, optionally containing one, two, or three additional heteroatoms independently selected from O, S, and NR;

and wherein any of the foregoing alkyl, alkenyl, aryl, heteroaryl, heterocyclic, and alkynyl groups can be unsubstituted or substituted by halo, hydroxy, $C_1$–$C_6$ alkoxy, amino, nitro, $C_1$–$C_4$ alkylamino, di($C_1$–$C_4$) alkylamino, $C_3$–$C_6$ cycloalkyl, phenyl, phenoxy, $C_3$–$C_5$ heteroaryl or heterocyclic radical, or $C_3$–$C_5$ heteroaryloxy or heterocyclic radical-oxy; or a pharmaceutically acceptable salt, ester, amide or prodrug thereof.

6. The method of claim 5, wherein the phenyl amine has a structure of Formula (II) wherein $R_{1a}$ is methyl, fluoro, or chloro; $R_{2a}$ is H; $R_{3a}$, $R_{4a}$, and $R_{5a}$ are each H or F; $R_{6a}$ is H; R$_{7a}$ is methyl, ethyl, 2-propenyl, propyl, butyl, pentyl, hexyl, cyclopropylmethyl, cyclobutyl methyl, cyclopropylmethyl, or cyclopropylethyl; and 4' position is I.

7. The method of claim 5, comprising a MEK inhibitor having a structure of Formula (II) wherein: R$_{4a}$ is F at the 4 position, para to the CO—N—R$_{6a}$—OR$_{7a}$ group and meta to the bridging nitrogen; at least one of R$_{3a}$ and R$_{5a}$ is F or Cl; and R$_{1a}$ is methyl or chloro.

8. The method of claim 5, wherein the phenyl amine has a structure selected from:

4-Fluoro-N-hydroxy-2-(4-iodo-2-methyl-phenylamino)-benzamide;
   4-Fluoro-2-(4-iodo-2-methyl-phenylamino)-N-(methoxy)-benzamide;
   4-Fluoro-2-(4-iodo-2-methyl-phenylamino)-N-(prop-2-ynyloxy)-benzamide;
   4-Fluoro-2-(4-iodo-2-methyl-phenylamino)-N-(2-phenoxyethoxy)-benzamide;
   4-Fluoro-2-(4-iodo-2-methyl-phenylamino)-N-(2-thienylmethoxy)-benzamide;
   4-Fluoro-2-(4-iodo-2-methyl-phenylamino)-N-(prop-2-enyloxy)-benzamide;
   4-Fluoro-2-(4-iodo-2-methyl-phenylamino)-N-(cyclopropylmethoxy)-benzamide;
   4-Fluoro-2-(4-iodo-2-methyl-phenylamino)-N-(cyclopentoxy)-benzamide;
   3,4-Difluoro-2-(4-iodo-2-methyl-phenylamino)-N-(3-furylmethoxy)-benzamide;
   3,4-Difluoro-2-(4-iodo-2-methyl-phenylamino)-N-ethoxy-benzamide;
   3,4-Difluoro-2-(4-iodo-2-methyl-phenylamino)-N-(but-2-enyloxy)-benzamide;
   3,4-Difluoro-2-(4-iodo-2-methyl-phenylamino)-N-(cyclopropylmethoxy)-benzamide;
   3,4-Difluoro-2-(4-iodo-2-methyl-phenylamino)-N-(1-methylprop-2-ynyloxy)-benzamide;
   3,4-Difluoro-2-(4-iodo-2-methyl-phenylamino)-N-(3-phenylprop-2-ynyloxy)-benzamide;
   3,4-Difluoro-2-(4-iodo-2-methyl-phenylamino)-N-(prop-2-ynyloxy)-benzamide;
   3,4-Difluoro-2-(4-iodo-2-methyl-phenylamino)-N-(propoxy)-benzamide;
   3,4-Difluoro-2-(4-iodo-2-methyl-phenylamino)-N-(cyclobutyloxy)-benzamide;
   3,4-Difluoro-2-(4-iodo-2-methyl-phenylamino)-N-(2-thienylmethoxy)-benzamide;
   3,4-Difluoro-2-(4-iodo-2-methyl-phenylamino)-N-(2-methyl-prop-2-enyloxy)-benzamide;
   3,4-Difluoro-2-(4-iodo-2-methyl-phenylamino)-N-(2-phenoxyethoxy)-benzamide;
   3,4-Difluoro-2-(4-iodo-2-methyl-phenylamino)-N-(but-2-enyloxy)-benzamide;
   3,4-Difluoro-2-(4-iodo-2-methyl-phenylamino)-N-(but-3-ynyloxy)-benzamide;
   3,4-Difluoro-2-(4-iodo-2-methyl-phenylamino)-N-(cyclopentyloxy)-benzamide;
   3,4-Difluoro-2-(4-iodo-2-methyl-phenylamino)-N-(3-(2-fluorophenyl)-prop-2-ynyloxy)-benzamnide;
   5-Bromo-3,4-difluoro-N-hydroxy-2-(4-iodo-2-methyl-phenylamino)-benzamide;
   5-Bromo-3,4-difluoro-2-(4-iodo-2-methyl-phenylamino)-N-(n-propoxy)-benzamide;
   5-Bromo-3,4-difluoro-N-(furan-3-ylmethoxy)-2-(4-iodo-2-methyl-phenylamino)-benzamide;
   5-Bromo-N-(but-2-enyloxy)-3,4-difluoro-2-(4-iodo-2-methyl-phenylamino)-benzamide
   5-Bromo-N-butoxy-3,4-difluoro-2-(4-iodo-2-methyl-phenylamino)-benzamide;
   5-Bromo-3,4-difluoro-2-(4-iodo-2-methyl-phenylamino)-N-(3-methyl-but-2-enyloxy)-benzamide;
   5-Bromo-3,4-difluoro-2-(4-iodo-2-methyl-phenylamino)-N-(prop-2-ynyloxy)-benzamide;
   5-Bromo-3,4-difluoro-2-(4-iodo-2-methyl-phenylamino)-N-[3-(3-methoxy-phenyl)-prop-2-ynyloxy]-benzamide;
   5-Bromo-3,4-difluoro-2-(4-iodo-2-methyl-phenylamino)-N-(thiophen-2-ylmethoxy)-benzamide;
   5-Bromo-3,4-difluoro-2-(4-iodo-2-methyl-phenylamino)-N-(pyridin-3-ylmethoxy)-benzamide;
   5-Bromo-3-4-difluoro-2-(4-iodo-2-methyl-phenylamino)-N-(3-(2-fluorophenyl)-prop-2-ynyloxy)-benzamide;
   5-Bromo-3,4-difluoro-2-(4-iodo-2-methyl-phenylamino)-N-(ethoxy)-benzamide;
   5-Bromo-3,4-difluoro-2-(4-iodo-2-methyl-phenylamino)-N-(cyclopropylmethoxy)-benzamide;
   5-Bromo-3,4-difluoro-2-(4-iodo-2-methyl-phenylamino)-N-(isopropoxy)-benzamide;
   5-Bromo-3,4-difluoro-2-(4-iodo-2-methyl-phenylamino)-N-(but-3-ynyloxy)-benzamide;
   5-Chloro-N-hydroxy-2-(4-iodo-2-methyl-phenylamino)-benzamide;
   5-Chloro-2-(4-iodo-2-methyl-phenylamino)-N-(tetrahydro-pyran-2-yloxy)-benzamide;
   5-Chloro-2-(4-iodo-2-methyl-phenylamino)-N-methoxy-benzamide;
   4-Bromo-2-(4-iodo-2-methyl-phenylamino)-N-phenylmethoxy-benzamide;
   4-Fluoro-2-(4-iodo-2-methyl-phenylamino)-N-phenylmethoxy-benzamide;
   5-Fluoro-N-hydroxy-2-(4-iodo-2-methyl-phenylamino)-benzamide;
   5-Iodo-2-(4-iodo-2-methyl-phenylamino)-N-phenylmethoxy-benzamide;
   5-Fluoro-2-(4-iodo-2-methyl-phenylamino)-N-(tetrahydropyran-2-yloxy)-benzamide;
   3,4-Difluoro-2-(4-bromo-2-methyl-phenylamino)-N-(3-phenylprop-2-ynyloxy)-benzamide;
   3,4-Difluoro-2-(4-bromo-2-methyl-phenylamino)-N-(3-furylmethoxy)-benzamide;
   3,4-Difluoro-2-(4-bromo-2-methyl-phenylamino)-N-(2-thienylmethoxy)-benzamide;
   3,4-Difluoro-2-(4-bromo-2-methyl-phenylamnino)-N-(but-3-ynyloxy)-benzamide;
   3,4-Difluoro-2-(4-bromo-2-methyl-phenylamino)-N-(2-methyl-prop-2-enyloxy)-benzamide;
   3,4-Difluoro-2-(4-bromo-2-methyl-phenylamino)-N-(but-2-enyloxy)-benzamide;
   3,4-Difluoro-2-(4-bromo-2-methyl-phenylamino)-N-(methoxy)-benzamide;
   3,4-Difluoro-2-(4-bromo-2-methyl-phenylamino)-N-(ethoxy)-benzamide;
   3,4-Difluoro-2-(4-bromo-2-methyl-phenylamino)-N-(cyclobutoxy)-benzamide;

3,4-Difluoro-2-(4-bromo-2-methyl-phenylamino)-N-(isopropoxy)-benzamide;
3,4-Difluoro-2-(4-bromo-2-methyl-phenylamino)-N-(2-phenoxyethoxy)-benzamide;
3,4-Difluoro-2-(4-bromo-2-methyl-phenylamino)-N-(cyclopropylmethoxy)-benzamnide;
3,4-Difluoro-2-(4-bromo-2-methyl-phenylamino)-N-(n-propoxy)-benzamnide;
3,4-Difluoro-2-(4-bromo-2-methyl-phenylamino)-N-(1-methyl-prop-2-ynyloxy)-benzamide;
3,4-Difluoro-2-(4-bromo-2-methyl-phenylamino)-N-(3-(3-fluorophenyl)-prop-2-ynyloxy)-benzamide;
3,4-Difluoro-2-(4-bromo-2-methyl-phenylamino)-N-(4,4-dimethylpent-2-ynyloxy)-benzamide;
3,4-Difluoro-2-(4-bromo-2-methyl-phenylamino)-N-(cyclopentoxy)-benzamide;
3,4,5-Trifluoro-N-hydroxy-2-(4-iodo-2-methyl-phenylamino)-benzamide;
5-Chloro-3,4-difluoro-N-hydroxy-2-(4-iodo-2-methyl-phenylamno)-benzamide;
5-Bromo-3,4-difluoro-2-(2-fluoro-4-iodo-phenylamino)-N-hydroxy-benzamide;
N-Hydroxy-2-(4-iodo-2-methyl-phenylamino)-4-nitro-benzamide;
3,4,5-Trifluoro-2-(2-fluoro-4-iodo-phenylamino)-N-hydroxy-benzamide;
5-Chloro-3,4-difluoro-2-(2-fluoro-4-iodo-phenylamino)-N-hydroxy-benzamde;
5-Bromo-2-(2-chloro-4-iodo-phenylamino)-3,4-difluoro-N-hydroxy-benzamide;
2-(2-Fluoro-4-iodo-phenylamino)-N-hydroxy-4-nitro-benzamide;
2-(2-Chloro-4-iodo-phenylamino)-3,4,5-trifluoro-N-hydroxy-benzamide;
5-Chloro-2-(2-chloro-4-iodo-phenylamino)-3,4-difluoro-N-hydroxy-benzamide;
5-Bromo-2-(2-bromo-4-iodo-phenylamino)-3,4-difluoro-N-hydroxy-benzamide;
2-(2-Chloro-4-iodo-phenylam ino)-N-hydroxy-4-methyl-benzamide;
2-(2-Bromo-4-iodo-phenylamino)-3,4,5-trifluoro-N-hydroxy-benzamide;
2-(2-Bromo-4-iodo-phenylamino)-5-chloro-3,4-difluoro-N-hydroxy-benzamide;
2-(2-Bromo-4-iodo-phenylamino)-N-hydroxy-4-nitro-benzamide;
4-Fluoro-2-(2-fluoro-4-iodo-phenylamino)-N-hydroxy-benzamide;
3,4-Difluoro-2-(2-fluoro-4-iodo-phenylamino)-N-hydroxy-benzamide;
2-(2-Chloro-4-iodo-phenylamino)-4-fluoro-N-hydroxy-benzamide;
2-(2-Chloro-4-iodo-phenylamino)-3,4-difluoro-N-hydroxy-benzamide;
2-(2-Bromo-4-iodo-phenylamino)-4-fluoro-N-hydroxy-benzamide;
2-(2-Bromo-4-iodo-phenylamino)-3,4-dfluoro-N-hydroxy-benzamide;
N-Cyclopropylmethoxy-3,4,5-trifluoro-2-(4-iodo-2-methyl-phenylaniino)-benzamide;
5-Chloro-N-cyclopropylmethoxy-3,4-difluoro-2-(4-iodo-2-methyl-phenylamino)-benzamide;
5-Bromo-N-cyclopropylmethoxy-3,4-difluoro-2-(2-fluoro-4-iodo-phenylamino)-benzamide;
N-Cyclopropylmethoxy-2-(4-iodo-2-methyl-phenylamino)-4-nitro-benzamide;
N-Cyclopropylmethoxy-3,4,5-trifluoro-2-(2-fluoro-4-iodo-phenylamino)-benzamide;
5-Chloro-N-cyclopropylmethoxy-3,4-difluoro-2-(2-fluoro-4-iodo-phenylamino)-benzamide;
5-Bromo-2-(2-chloro-4-iodo-phenylamino)-N-cyclopropylmethoxy-3,4-difluoro-benzamide;
N-Cyclopropylmethoxy-2-(2-fluoro-4-iodo-phenylamino)-4-nitro-benzamide;
2-(2-Chloro-4-iodo-phenylamino)-N-cyclopropylmethoxy-3,4,5-trifluoro-benzamide;
5-Chloro-2-(2-chloro-4-iodo-phenylamino)-N-cyclopropylmethoxy-3,4-difluoro-benzamide;
5-Bromo-2-(2-bromo-4-iodo-phenylamno)-N-ethoxy-3,4-difluoro-benzamide;
2-(2-Chloro-4-iodo-phenylamino)-N-ethoxy-4-nitro-benzamide;
2-(2-Bromo-4-iodo-phenylamino)-N-cyclopropylmethoxy-3,4,5-trifluoro-benzamide;
2-(2-Bromo-4-iodo-phenylamino)-5-chloro-N-cyclopropylmethoxy-3,4-difluoro-benzamide
2-(2-Bromo-4-iodo-phenylamino)-N-cyclopropylmethoxy-4-nitro-benzamide;
N-Cyclopropylmethoxy-4-fluoro-2-(2-fluoro-4-iodo-phenylamino)-benzmide;
N-Cyclopropylmethoxy-3,4-difluoro-2-(2-fluoro-4-iodo-phenylamino)-benzamide;
2-(2-Chloro-4-iodo-phenylamino)-N-cyclopropylmethoxy-4-fluoro-benzamide;
2-(2-Chloro-4-iodo-phenylamino)-N-cyclopropylmethoxy-3,4-difluoro-benzamide;
2-(2-Bromo-4-iodo-phenylamino)-N-cyclopropylmethoxy-4-fluoro-benzamide; and
2-(2-Bromo-4-iodo-phenylamino)-N-cyclopropylmethoxy-3,4-difluoro-benzamide.

9. A method of preventing or treating asthma in a mammal comprising administering to a in need of treatment or suspected of developing asthma and in need of prophylactic treatment an antiasthmatic effective dose of the MEK inhibitor 2-(2-chloro-4-iodophenylamino)-N-cyclopropylmethoxy-3,4-difluorobenzamide.

10. A method of preventing or treating asthma in a mammal comprising administering to a patiemammal in need of treatment or suspected of developing asthma and in need of prophylactic treatment an antiasthmatic effective dose of the MEK inhibitor 2-(2-methyl-4-iodophenylamino)-N-hydroxy-3,4-difluoro-5-bromobenzamide.

11. The method of preventing or treating asthma in a mammal comprising administering to a patietmammal in need of treatment or suspected of developing asthma and in need of prophylactic treatment an antiasthmatic effective dose of a compound selected from:
2-(2-Chloro-4-iodophenylamino)-N-cyclopropylmethoxy-3,4-difluorobenzamide;
2-(2-Methyl-4-iodophenylamino)-N-hydroxy-4-fluorobenzamide;
2-(2-Methyl-4-iodophenylamino)-N-hydroxy-3,4-difluoro-5-bromobenzamide;
2-(2-Methyl-4-iodophenylamino)-N-cyclopropylmethoxy-3,4-difluoro-5-bromobenzamide;

2-(2-Methyl-4-iodophenylamino)-N-cyclobutylmethoxy-3,4-difluoro-5-bromobenzamide;

2-(2-Chloro-4-iodophenylamino)-N-cyclopropylmethoxy-3,4-difluoro-5-bromobenzamide;

2-(2-Chloro-4-iodophenylamino)-N-hydroxy-3,4-difluoro-5-bromobenzamide;

2-(2-Chloro-4-iodophenylamino)-N-cyclobutylmethoxy-3,4-difluorobenzamide;

2-(2-Chloro-4-iodophenylamino)-N-hydroxy-4-fluorobenzamide;

2-(2-Methyl-4-iodophenylamino)-N-hydroxy-3,4-difluorobenzamide;

2-(2-Methyl-4-iodophenylamino)-N-cyclopropylmethoxy-3,4,5-trifluorobenzamide; and 2-(2-Chloro-4-iodophenylamino)-N-cyclopropylmethoxy-4-fluorobenzamide.

12. A method of preventing or treating asthma in a mammal comprising administering to a mammal in need of treatment or suspected of developing asthma and in need of prophylactic treatment an antiasthmatic effective dose of a compound:

2-(2-chloro-4-iodophenylamino)-5-chloro-N-cyclopropylmethoxy -3,4-difluorobenzamide, 2-(4-iodophenylamino)-N-cyclopropylmethoxy-5-chloro-3,4-difluorobenzamide, 2-(4-iodophenylamino)-5-chloro-3,4-difluorobenzoic acid, 2-(2-chloro-4-iodophenylamino)-5-chloro-3,4-difluorobenzoic acid, 5-chloro-3,4-difluoro-2-(4-iodo-2-methylphenylamino)-benzoic acid; and 5-chloro-N-cyclopropylmethoxy -3,4-difluoro-2-(4-iodo-2-methylphenylamino)-benzamide.

13. A method of preventing or treating asthma in a mammal comprising administering to a mammal in need of treatment or suspected of developing asthma and in need of prophylactic treatment an antiasthmatic effective dose of a compound which is 2-(2-amino-3-methoxyphenyl)-4-oxo-4H-benzopyran or 2-(2-Methyl-4-iodophenylamino)-N-hydroxy-3,4-difluoro-5-bromobenzamide.

* * * * *